US012751720B2

(12) United States Patent
Orphanos et al.

(10) Patent No.: US 12,751,720 B2
(45) Date of Patent: Oct. 6, 2026

(54) HUMERAL RESECTION GUIDES, AND RELATED METHODS, FOR USE IN TISSUE SPARING SHOULDER ARTHROPLASTIES

(71) Applicant: DePuy Synthes Products, Inc., Raynham, MA (US)

(72) Inventors: Stephen J. Orphanos, Bridgewater, MA (US); Mollie Waters, Boston, MA (US); Robert Ciocca, Woonsocket, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 18/823,212

(22) Filed: Sep. 3, 2024

(65) Prior Publication Data

US 2025/0072905 A1 Mar. 6, 2025

Related U.S. Application Data

(60) Provisional application No. 63/579,942, filed on Aug. 31, 2023.

(51) Int. Cl.
*A61B 17/15* (2006.01)

(52) U.S. Cl.
CPC .................................. *A61B 17/151* (2013.01)

(58) Field of Classification Search
CPC ... A61B 17/151; A61B 17/15; A61B 17/1684; A61B 17/1778
See application file for complete search history.

(56) References Cited

U.S. PATENT DOCUMENTS 6,589,281 B2 7/2003 Hyde, Jr.
7,901,408 B2 3/2011 Ek et al.
8,157,866 B2 4/2012 Winslow et al.
8,936,645 B1 1/2015 Masson
(Continued)

FOREIGN PATENT DOCUMENTS

CN 103006298 B 3/2016
CN 109561900 B 2/2022
(Continued)

OTHER PUBLICATIONS

International Search Report and Written Opinion for Application No. PCT/US2024/044991, mailed Dec. 9, 2024 (10 pages).
(Continued)

*Primary Examiner* — Matthew J Lawson
(74) *Attorney, Agent, or Firm* — Barnes & Thornburg LLP

(57) ABSTRACT

Devices and methods for performing a humeral cut, the humeral cut being performed to prepare a surgical site to receive a prosthesis. In at least some embodiments, a humeral resection guide is provided that includes a plurality of arms that can be selectively coupled and decoupled from each other, thus enabling the arms to be individually delivered to a surgical site and then subsequently coupled together. This type of configuration allows for less trauma to the tissue in and/or surrounding the shoulder joint because the components being delivered to the surgical site are smaller during delivery than when in use. Additional features are provided that help create a preferred fit with respect to the humeral head to set a desired resecting plane, as well as to insure cutting tools do not harm surrounding tissue.

20 Claims, 22 Drawing Sheets

(56) References Cited

U.S. PATENT DOCUMENTS

| | | | |
|---|---|---|---|
| 9,078,673 B2 | 7/2015 | Fitzpatrick | |
| 9,119,643 B2 | 9/2015 | Winslow et al. | |
| 9,132,016 B2 | 9/2015 | Flaherty et al. | |
| 9,370,428 B2 | 6/2016 | Winslow et al. | |
| 9,414,847 B2 | 8/2016 | Kurtz | |
| 9,445,910 B2 | 9/2016 | Chudik | |
| 9,968,459 B2 | 5/2018 | Chudik | |
| 10,022,237 B2 | 7/2018 | Linares | |
| 10,786,265 B2 | 9/2020 | Gunther | |
| 11,058,544 B2 | 7/2021 | Sanchez-Sotelo et al. | |
| 11,103,258 B2 | 8/2021 | Bahk | |
| 11,298,245 B2 | 4/2022 | Paterson et al. | |
| 11,369,479 B2 | 6/2022 | Greiwe | |
| 11,395,742 B2 | 7/2022 | Birmingham | |
| 2001/0047210 A1 | 11/2001 | Wolf | |
| 2005/0043805 A1 | 2/2005 | Chudik | |
| 2006/0004373 A1* | 1/2006 | Ondrla | A61B 17/15 606/87 |
| 2007/0038302 A1 | 2/2007 | Shultz et al. | |
| 2009/0287217 A1* | 11/2009 | Ammann | A61B 17/1675 606/88 |
| 2010/0145345 A1* | 6/2010 | Ammann | A61B 17/8095 606/88 |
| 2012/0143267 A1* | 6/2012 | Iannotti | A61B 17/1746 606/86 R |
| 2015/0223941 A1 | 8/2015 | Lang | |
| 2015/0320430 A1* | 11/2015 | Kehres | A61B 17/15 606/87 |
| 2016/0089164 A1 | 3/2016 | Winslow et al. | |
| 2017/0079803 A1 | 3/2017 | Lang | |
| 2019/0015113 A1* | 1/2019 | Morvan | A61B 17/15 |
| 2020/0368033 A1 | 11/2020 | Britton et al. | |
| 2021/0145462 A1* | 5/2021 | Stchur | A61B 17/1684 |
| 2021/0212706 A1 | 7/2021 | Kehres et al. | |
| 2021/0386561 A1 | 12/2021 | Termanini | |
| 2024/0108433 A1 | 4/2024 | Orphanos et al. | |
| 2024/0180567 A1* | 6/2024 | Dye, Jr. | A61B 17/15 |
| 2025/0072910 A1 | 3/2025 | Orphanos et al. | |
| 2025/0072911 A1 | 3/2025 | Orphanos et al. | |

FOREIGN PATENT DOCUMENTS

| | | |
|---|---|---|
| WO | 2022203921 A1 | 9/2022 |
| WO | 2024118308 A1 | 6/2024 |

OTHER PUBLICATIONS

DePuy Synthes, Global Unite Platform Shoulder System Anatomic and Reverse Surgical Technique Guide, 2020 (64 pages).

* cited by examiner

HUMERAL RESECTION GUIDES, AND RELATED METHODS, FOR USE IN TISSUE SPARING SHOULDER ARTHROPLASTIES

CROSS REFERENCE TO RELATED APPLICATION

The present disclosure claims priority to and the benefit of U.S. Provisional Patent Application No. 63/579,942, entitled "Humeral Cut Guides, and Related Methods, for Use in Tissue Sparing Shoulder Arthroplasties," filed Aug. 31, 2023, the disclosure of which is incorporated by reference herein in its entirety.

FIELD

The present disclosure relates to devices and methods used in shoulder repair procedures, such as shoulder arthroplasties, and more particularly relates to devices, and associated methods, used to guide the resection of a humeral head in a limited space, such as through the rotator interval, while allowing surrounding tendons such as the subscapularis tendon to remain intact.

BACKGROUND

During the lifetime of a patient, it may be necessary to perform a shoulder arthroplasty due to, for example, disease or trauma. Various forms of this type of surgery exist, with the overarching purpose being to remove and/or replace damaged or missing portions of the anatomy with prosthetic components. For example, as shown in FIG. 1A, in an anatomic total shoulder arthroplasty, a humeral prosthesis 10 can be used to replace the natural head of a patient's humerus. The humeral prosthesis 10 typically includes an elongated post component 12 that is implanted into an intramedullary canal of the patient's humerus and a hemispherical-shaped prosthetic head component 14 that is secured to the post component 12. Additionally, the natural glenoid surface of the scapula can be resurfaced or otherwise replaced with an anatomic glenoid implant 20. An anatomic glenoid implant 20 typically includes a concave bearing surface 24 upon which the prosthetic head component 14 of the humeral prosthesis 10 articulates. A peg or keel 22 can project from the distal end of the implant 20 and can be secured (e.g., cemented) into the glenoid cavity of the patient's scapula.

While FIG. 1A provides for an anatomic total shoulder arthroplasty, in other instances, the arthroplasty may be a partial shoulder arthroplasty, meaning only a portion of the shoulder anatomy may be replaced with an implant. This may include, for example, only providing for a humeral prosthesis without a glenoid implant, or a glenoid implant without a humeral prosthesis, among other variations appreciated by those skilled in the art. Further, while FIG. 1A provides for an anatomic procedure, reverse procedures are also known procedures for repairing shoulders. They can be helpful, for example, when a patient's natural shoulder has degenerated to a severe degree of joint instability and pain. In a reverse procedure, the mechanics of the shoulder can be changed, reversing the anatomy, or structure, of the healthy shoulder. For example, as shown in FIG. 1B, in a reverse total shoulder arthroplasty, a humeral prosthesis 50 can be used to replace the natural head of the patient's humerus. The humeral prosthesis 50 typically includes an elongated post component 52 that is implanted into an intramedullary canal of the patient's humerus and a concave-shaped prosthetic head component 54, known as a humeral cup, is secured to the post component 52. Additionally, a reverse glenoid implant, e.g., a hemispherical-shaped glenosphere 60, can be secured to the glenoid bone of the patient's scapula. Such a reverse configuration allows the patient's deltoid muscle, which is one of the larger and stronger shoulder muscles, to raise the arm.

During various types of shoulder arthroplasty surgeries, there is soft tissue impeding access to the surgical arthroplasty site. This tissue typically includes a patient's subscapularis tendon. In many traditional surgical approaches, the subscapularis tendon is detached from a humeral attachment point on the humerus to provide better access to the surgical site. In at least some arthroplasty procedures, the humerus is subsequently externally rotated to allow access to the joint space, essentially dislocating the humeral head. This provides a surgeon full visibility to the humeral head. In an anatomical procedure in which the humeral head is being replaced, once the humeral head is exposed, the convex portion of the bone is resected to a flat plane (referred to herein as the "humeral resection surface") and prepared to receive a humeral prosthesis. In a reverse procedure, the location where the humeral head is typically located can be prepared to receive a prosthetic head component (e.g., a humeral cup) after the humeral head is externally rotated.

Upon gaining sufficient access to the surgical site, surgeons often employ guides, referred to herein as humeral resection guides or humeral cut guides (sometimes "guide" for short), among other names, in conjunction with resecting or cutting the humeral head at the appropriate location. The guides grasp the humerus and/or humeral head and/or surrounding bone, helping to define and/or set a location at which the humeral cut is to occur. One or more resection or cutting tools can then be used to perform the cut, typically with the guide still in place. These guides can be referred to as humeral resection guides, among other terminology known to those skilled in the art (e.g., humeral cut guide). For at least an anatomical procedure, the location at which resection or cutting occurs is generally at an articular margin where the convex head meets the neck (see articular margin 1009 illustrated in FIG. 2, and related description below). Existing humeral resection guides are designed for use in procedures in which the subscapularis tendon has been detached from its humeral attachment point to allow a full 360° view of the humeral head anatomy, for instance while placing resection guides. The size, shape, and function of such resection guides is based on having access and visualization to the joint space that is not inhibited by the subscapularis tendon and/or other tissue that may impede access to the surgical site. Following surgery, the subscapularis tendon is reattached. Repair and healing of the tendon are critical to the proper function of the joint and incomplete healing results in complications, pain, and instability. These actions are all necessary because existing anatomic humeral resection guides typically rely on visualizing the humeral articular margin (e.g., the articular margin 1009 in FIG. 2), and so current procedures fully expose the humeral head so all aspects of the articular margin can be visualized and palpated to fine tune resection guide position before securement to the bone for cutting. Additionally, resection guide securement pin entry and exit points are visualized for confirmation before bone resection.

Alternatively, the procedure can be performed leaving the subscapularis tendon attached—referred to as tissue sparing—such that the surgeon(s) works only within the limited joint space superior and inferior to the tissue borders of the subscapularis. In such instances, a surgeon typically uses existing resection and/or cutting tools to help manipulate the subscapularis tendon during their insertion to allow the tools for resecting and/or cutting to get to the surgical site for subsequent use. Tools like traditional humeral resection guides, however, are not suitable for use in such a tissue sparing procedure. Traditional humeral resection guides are not capable of operating within the limited joint space superior and inferior to the tissue borders. Further, traditional humeral resection guides are not being used during transhumeral procedures at least because, prior to the present disclosure, transhumeral approaches for shoulder arthroplasty were not being performed. At least because existing humeral resection guides are designed for use when the subscapularis tendon has been detached, they are too bulky and cumbersome to use in a tissue sparing procedure. Existing humeral resection guides do not have the versatility in movement and function to allow the guide to be positioned accurately to properly grasp the humeral head and/or surrounding bone and help guide the cutting or resection of the humeral head. Further, existing anatomic humeral resection guides typically rely on visualizing the humeral articular margin. However, because current procedures fully expose the humeral head, all aspects of the articular margin can be visualized and palpated to fine tune resection guide position before securement to the bone for cutting.

Accordingly, there is a need for humeral resection guides, and related methods, for use in tissue sparing arthroplasty procedures where access is limited while also minimizing damage to surrounding soft tissue, and adjacent neurovascular and boney structures.

SUMMARY

The present disclosure is generally directed to various embodiments of surgical guides, referred to as humeral resection or cut guides, that can be disposed at a humeral head of a humerus and used to define a flat plane along which a cutting tool can be passed to resect a portion of the humeral head, thus creating a flat, resected surface (referred to herein as the "humeral resection surface") for receiving an implant and/or prosthesis. The size and configuration of the guide enables the guide to be placed at the surgical site while minimizing any damage to soft tissue in a glenohumeral joint space during insertion, use, and removal of the resection guide. The guide includes various features that help to define the flat plane, also referred to as a cutting plane, the flat plane being able to have different angles depending on the desired configuration of the humeral resection surface. The features include an extender that can be coupled to the resection guide to achieve a "patient specific anatomic" resection, a version handle that can be used for version and humeral shaft alignment, and a guide pin or rod that can help confirm placement of the resection guide with respect to the humerus and can also be used in manipulating a location of the resection guide with respect to the humeral head and humerus. The humeral resection guides disclosed herein provide a number of advantages as compared to traditional humeral resection guides, including the ability to mark and/or guide the resection of a humeral head while the subscapularis tendon remains intact with a humeral attachment point for the duration of the surgical procedure. The designs of the humeral resection guides disclosed are tailored towards allowing for access through smaller areas than traditional humeral guides access due to the subscapularis tendon not being detached, such as through a rotator interval, while providing for versatility in movement to allow for precision and still operating in the small, confined surgical space.

Additional versatility can be achieved by various adjustable mechanisms associated with at least some of the disclosed humeral resection guides. At least some embodiments of the guides can have various degrees of freedom, enabling for virtually any positioning of the guide to be achieved to define a cutting or resecting plane at a desired position and/or accommodate resecting from any approach. These degrees can include inferior movement, superior movement, a vertical movement, a swinging movement, and/or a rotational movement. More particularly, with respect to use in a shoulder procedure, the humeral resection guides of the present disclosure allow a surgeon to adjust and take into consideration the following aspects: (1) positioning vertically on an inferior articular margin; (2) positioning superiorly against a superior articular margin at the attachment of the supraspinatus and greater tuberosity; (3) version alignment with patient anatomy; (4) alignment with the humeral long bone to achieve a specific cut plane angle; and/or (5) adjustment of the resection guide to closely approximate peripheral anatomy, for example for securing and/or pinning to the bone before resection of a boney anatomy. These degrees can be achieved, for example, by various designs of the guides themselves, as well as with the use of other components, such as bone pins, that can be used in conjunction with the same.

A person skilled in the art will appreciate the glenohumeral joint has six degrees of freedom, axial and rotational movement along three axes. The versatility of the disclosed resection guides account for these degrees of freedom when defining the cutting plane. More specifically, features are present to place the guide at a correct angle of inclination and version angle to mimic patient anatomy. The angle of inclination can be defined as the angle the head of the humerus projects from the longitudinal axis of the humeral shaft, and the version angle can be defined by the angle of rotation of the humeral head in the transverse plane. The various mechanisms and features that enable this versatility of movement and function are described in greater detail below. By way of non-limiting examples, a vertical alignment plate can extend from a surface of a resection guide that defines the cutting plane, and can be engaged by a version handle capable of moving the resection guide to align with a humeral shaft, putting a plane created by the guide at an appropriate flexion/extension angle or tilt (e.g., a humeral cut plane angle of about 135° for an anatomic procedure) to mimic the natural angle of the humeral head with respect to the humeral shaft. By way of further non-limiting example, vertical alignment rods can couple to the version handle or the vertical alignment plate, and can extend from one or both of superior and inferior directions to lengthen the aforementioned vertical alignment plate outside of the joint space and/or visually align the resection guide at a desired angle.

Still further, various "ease of use" features are also provided in the various designs disclosed. These can include features that enable for a surgeon to easily identify where any resection or cut should be performed, features that enable for various tools used during the course of the procedure to be easily guided to the desired location(s) by such features, and/or features designed to make the use of such surgical tools easier to use than would otherwise be the case without such features. Various mechanisms and features that enable ease of use of the various surgical instruments during a repair procedure are described in greater detail below. By way of non-limiting examples, various grooves and openings can be formed in at least some designs of the disclosed humeral resection guides to allow for bone or guide pins to fix the guide to the bone, proximate to and/or at the surgical site, and/or resecting and/or cutting tools to be guided to the proper location at which such tools will be operated to perform the desired resection and/or cut. As described herein, use of features to position bone pins or the like in bone can be in a manner that avoids passing through tissue, though in some embodiments, it can be acceptable to pass a bone pin through tissue.

One embodiment of a resection guide includes a superior radial arm and a guide slot. A proximal portion of the superior radial arm includes at least one bone pin receiving opening formed in the arm and a superior surface, while a distal portion of the superior radial arm is configured to engage a humeral head of a humerus. The superior surface defines a resecting plane of the resection guide. The guide slot is formed on the superior radial arm. The guide slot is defined by a ledge of the distal portion of the superior radial arm extending over the superior surface of the proximal portion of the superior radial arm. Further, the guide slot is configured to receive a cutting instrument through the guide slot and guide the cutting instrument along the resecting plane while cutting the humeral head, keeping the cutting instrument one of parallel or substantially parallel to the resecting plane.

The resection guide can include a vertical alignment plate. The vertical alignment plate can extend distally from the superior radial arm. A length of the vertical alignment plate and the superior surface of the proximal portion of the superior radial arm can form an angle between the two, with the angle defining a resecting angle of the resection guide, and thus an angle of the resecting plane of the resection guide. In at least some such embodiments, the angle formed by the length of the vertical alignment plate and the superior surface of the proximal portion of the superior radial arm can be congruent with the resecting angle of the resection guide, and thus the angle of the resecting plane of the resection guide.

The resection guide can also include at least one handle-receiving opening formed in the vertical alignment plate. The opening can be configured to receive a version handle for manipulating a location of the superior radial arm with respect to the humerus and/or checking for version alignment between the resection guide and the humerus.

In at least some embodiments, the resection guide can further include a version handle. The version handle can be configured to be coupled to the vertical alignment plate and can be configured to manipulate a location of the superior radial arm with respect to the humerus and/or check for version alignment between the resection guide and the humerus. In at least some such embodiments, the version handle can include a locking mechanism configured to selectively unlock and lock a location of the version handle with respect to the vertical alignment plate. The locking mechanism can include, for example, a latch. A distal portion of the version handle can form an angle with the proximal portion of the version handle to define a retroversion angle. The retroversion angle can be, for example, approximately 30°. The version handle can further include at least one opening formed in it, the opening(s) for receiving a vertical guide rod. The opening(s) can be configured to receive a vertical guide rod such that the vertical guide rod can extend substantially along a length or axis defined by a shaft of the humerus. In at least some such embodiments, the opening(s) can include both a first opening and a second opening. The first opening can be configured to receive a vertical guide rod such that the vertical guide rod can extend distally, proximate to the shaft of the humerus, while the second opening can be configured to receive a vertical guide rod such that the vertical guide rod can extend proximally, away from the shaft of the humerus. In at least some embodiments, the resection guide can further include at least one vertical guide rod configured to be coupled to the vertical alignment plate by way of the opening(s). The vertical guide rod can be configured to extend substantially along a length or axis defined by the shaft of the humerus.

The at least one bone pin receiving opening can include a longitudinal axis that can extend through a length of the bone pin receiving opening(s) and that is substantially parallel to the resecting plane. In at least some embodiments, the at least one bone pin opening can include a plurality of bone pin receiving openings formed in the proximal portion of the superior radial arm. At least two such openings can be non-parallel. In at least some embodiments, an inner surface of the distal portion of the superior radial arm can include one or more gripping protrusions configured to help secure the superior radial arm to the humerus.

The resection guide can also include a removable extender. The removable extender can be coupled to the proximal portion of the superior radial arm and can be configured to extend the resecting plane inferiorly. The removable extender can include at least one inferior bone pin receiving opening. In at least some such embodiments, the removable extender can also include a lever configured to selectively lock and unlock the removable extender from the superior radial arm.

One embodiment of a method for resecting a humeral head includes coupling a superior arm of a resection guide to at least one of a humeral head or a humerus such that the superior arm engages the humeral head, and passing at least one bone pin through a portion of the resection guide and into at least one of the humeral head or the humerus. The method further includes resecting the humeral head using the resection guide to guide a cutting instrument and create a humeral resection surface.

In at least some embodiments, resecting the humeral head using the resection guide can include passing the cutting instrument through a guide slot formed on the superior arm, with the guide slot serving to guide the cutting instrument. Engaging the humeral head with a superior arm of a resection guide can include engaging the humeral head at a location that is at least one of at or proximate to a supraspinatus attachment point on the humeral head. The method can include aligning the guide slot to a bicipital groove of the humerus.

The method can also include aligning a vertical alignment plate of the resection guide with an elongate shaft of the humerus to set a location of the superior arm. In at least some such embodiments, a vertical guide rod can be coupled to at least one of the vertical alignment plate or a handle coupled to the vertical alignment plate, and the vertical guide rod can extend along the elongate shaft of the humerus in conjunction with aligning the vertical alignment plate of the resection guide with the elongate shaft of the humerus. The method can also include moving the vertical alignment plate to change an angle of inclination of a resecting plane defined by the resection guide.

The action of passing at least one bone pin through a portion of the resection guide and into at least one of the humeral head or the humerus can occur such that the at least one bone pin does not pass through soft tissue in the glenohumeral joint space. In other embodiments, the at least one pin can pass through soft tissue in the glenohumeral joint space.

In at least some embodiments, the method can include mating a handle to the resection guide and checking angular alignment with a forearm using the handle. The method can further include manipulating the handle to adjust a location of the superior arm of the resection guide.

In any of the embodiments provided for herein, a subscapularis tendon proximate to the humeral head can be intact during each of the coupling, passing, and resecting actions. The action of coupling a superior arm of a resection guide to at least one of a humeral head or a humerus such that the superior arm engages the humeral head further can include passing the superior arm through a rotator interval proximate to the humeral head.

The method can also include mating an extender to the superior arm and passing at least one inferior bone pin through a portion of the extender and into the humeral head such that the at least one inferior bone pin does not pass through soft tissue in the glenohumeral joint space. In at least some such embodiments, the method can further include passing the extender inferior to a subscapularis tendon proximate to the humeral head.

Another embodiment of a resection guide can include a first arm, a second arm, and a connection pivot. The first and second arms can each have a proximal portion and a distal portion, with the distal portion of the first arm being configured to engage a first portion of a bone to be cut and the distal portion of the second arm being configured to engage a second portion of the bone to be cut. Further, the first and second arms are configured to define a resecting plane for the resection guide. The connection pivot is disposed at the proximal portions of both the first and second arms such that the first arm pivots with respect to the second arm. Still further, the connection pivot is configured to selectively, pivotally couple the proximal portion of the first arm to the proximal portion of the second arm. The resection guide is configured to permit movement of one or both of the first or second arms across at least two degrees of freedom.

In at least some embodiments, the resection guide can be configured to permit each of the first arm and the second arm to be separately delivered to a surgical site and be subsequently coupled by way of the connection pivot while the first and second arms are located at the surgical site. The first and second arms can be configured to form a grasping perimeter that extends around at least a majority of a cross-sectional area of a perimeter of the bone to be cut. The grasping perimeter can extend around at least a majority, but not an entirety, of the cross-sectional area of the perimeter of the bone to be cut. For example, the grasping perimeter can be approximately in the range of about 50% to about 95% of the cross-sectional area of the perimeter of the bone to be cut.

The resection guide can be configured for use in a shoulder region such that the resecting plane defined by the first and second arms can be defined in a rotator interval of the shoulder region. In at least some embodiments, the resection guide can be configured for use in a shoulder region such the first arm can define a height of a resection plane when it is placed against a supraspinatus attachment.

The resection can include a horizontal slot. The horizontal slot can be formed in the proximal portion of the first arm. In at least some such embodiments, the connection pivot can be disposed in the horizontal slot when the proximal portions of the first and second arms are pivotally coupled by the connection pivot, and the first arm can be configured to move relative to the connection pivot such that a location of the connection pivot with respect to the horizontal slot changes, in turn changing a location of the first arm with respect to the second arm. The horizontal slot can include an open terminal end, and further, the first arm can be configured to be detached from the second arm by moving the first arm relative to the connection pivot such that the connection pivot passes out of the slot through the open terminal end.

In at least some embodiments the resection guide can further include at least one slot formed in a surface of at least one of the first and second arms. The at least one slot can be configured to receive a pin in the slot for setting a position of the resection guide with respect to the bone to be cut. In at least some such embodiments, the at least one slot can include both a first slot formed in a surface of the first arm and a second slot formed in a surface of the second arm. The at least one slot can be disposed at an angle with respect to the respective first or second arm such that it can be aligned with the resecting plane defined by the first and second arms. In at least some embodiments, the at least one slot can be configured to receive a bone pin in the slot and position the bone pin such that it is tangent to a superior portion of the resecting plane to extend a resecting surface of the resection guide, the resecting surface being a surface along which a cutting tool is configured to pass to perform a cut.

The second arm can include an elevated ridge on the distal portion of the second arm. The elevated ridge can extend above a defined resecting plane by the first and second arms. The resection guide can be configured for resecting to be performed with the first arm disconnected from the second arm such that the second arm remains at a surgical site while the first arm is removed from the surgical site.

The resection guide can also include a vertical alignment plate coupled to the second arm and configured to be aligned with an elongate shaft of the bone to be cut. An angle formed between the vertical alignment plate and a bottom surface of the second arm can be configured to help define a location of the defined resecting plane. In at least some such embodiments, the angle formed between the vertical alignment plate and the bottom surface of the second arm can be adjustable by moving a location of the vertical alignment plate with respect to the second arm.

In at least some embodiments, the resection guide can include a locking mechanism configured to engage the connection pivot to selectively place the connection pivot, and thus the first and second arms coupled to the connection pivot, in each of an unlocked configuration and a locked configuration. The locking mechanism can be configured to be moved between the unlocked configuration and the locked configuration with a single digit.

The resection guide can also include a vertical slot formed in the proximal portion of the second arm. In at least some such embodiments, the connection pivot can be disposed in the vertical slot when the proximal portions of the first and second arms are pivotally coupled by the connection pivot. Further, the connection pivot can be configured to move through the vertical slot to change a location of the first arm with respect to the second arm.

The resection guide can be configured to permit movement of one or both of the first or second arms, and thus the resecting plane defined by the first and second arms, across at least three degrees of freedom. In at least some embodiments, the at least three degrees of freedom can be at least four degrees of freedom or at least five degrees of freedom.

The bone to be cut can include a humeral head, and the resection guide can be configured such that the connection pivot allows for movement of the first arm with respect to the second arm to accommodate at least one of different humeral head sizes or different humeral head shapes. In other embodiments, the bone to be cut can include a humeral head, and the resection guide can be configured to be used to cut the humeral head while a subscapularis tendon proximate to the humeral head is intact. In at least some such embodiments, the resection guide can be configured to be inserted to a surgical site that includes the humeral head at least one of superior to the intact subscapularis tendon or inferior to the intact subscapularis tendon.

Another embodiment of a method for resecting a humeral head includes disposing a first arm of a resection guide proximate to a first portion of a perimeter of a humeral head of a humerus and disposing a second arm of the resection guide proximate to a second portion of the perimeter of the humeral head. After the first and second arms are proximate to the humeral head, the method can further include pivotally coupling the first arm to the second arm, engaging at least one of the humeral head or the humerus with first and second arms of the resection guide, the first and second arms defining a resecting plane, and resecting the humeral head.

In at least some embodiments, the action of disposing a first arm of a resection guide proximate to a first portion of a perimeter of a humeral head can include passing the first arm though a rotator interval and to a posterior portion of a humeral articular margin of the humeral head. The action of disposing a second arm of the resection guide proximate to a second portion of the perimeter of the humeral head can include passing the second arm through an inferior access point to an inferior articular margin of the humeral head. The action of pivotally coupling the first arm to the second arm can include disposing a pivot through proximal portions of each of the first and second arms to permit movement of one or both of the first or second arms across at least two degrees of freedom.

Engaging at least one of the humeral head or the humerus with the first and second arms of the resection guide can include rotating the first arm with respect to at least one of the pivot and the second arm. Resecting the humeral head can include resecting the humeral head along the resecting plane, using at least one of the first or second arms as a guide. In at least some embodiments, resecting the humeral head can include engaging an elevated ridge formed on at least one of the first and second arms with a cutting tool performing the resecting the humeral head, the elevated ridge preventing the cutting tool from extending beyond a desired surgical site.

A combination of the first portion of the perimeter of the humeral head and the second portion of the humeral head can be engaged by the first and second arms at a cross-section thereof such that at least a majority of a perimeter of the humeral head as defined at the cross-section is engaged by the first and second arms. In at least some such embodiments, the perimeter of the humeral head as defined at the cross-section that is engaged by the first and second arms is not an entirety of the perimeter of the humeral head as defined at the cross-section. For example, the perimeter that can be defined at the cross-section that is engaged by the first and second arms can be approximately in the range of about 50% to about 95% of the cross-sectional area of the perimeter of the humeral head.

The resecting plane defined by the first and second arms can be defined in a rotator interval proximate to the humeral head. The first arm can define a height of a resecting plane when it is placed against a supraspinatus attachment. The method can further include sliding the first arm with respect to the second arm approximately along an X-axis of the resecting plane to adjust a distance between a distal tip of the first arm and a proximal portion of the second arm. In at least some embodiments, the method can include sliding the first arm with respect to the second arm approximately along a Y-axis of the resecting plane to adjust a distance between a proximal portion of the first arm and at least one of a proximal portion, an intermediate portion, or a distal portion of the second arm.

The method can include rotating the resecting plane with respect to a vertical alignment plate that is one of coupled to or part of the second arm. In at least some embodiments, the method can include rotating a vertical alignment plate that is one of coupled to or part of the second arm. The method can include coupling at least one vertical extension rod to at least one of the first arm, the second arm, or, when provided, a vertical alignment plate that is one of coupled to or part of the second arm. In at least some such embodiments, the method can further include aligning the at least one vertical extension rod with an anatomical location to place the resection guide at a desired position.

In at least some embodiments, the method can include sliding the first arm with respect to the second arm to decouple the first arm from the second arm. The method can disengaging the first arm from the humeral head and decoupling the first arm from the second arm. Further, the action of resecting the humeral head can be performed with the second arm engaged with at least one of the humeral head or the humerus while the first arm is not engaged with either of the humeral head or humerus and is decoupled from the second arm.

The method can include locking movement of the first arm with respect to the second arm to place the first and second arms in a locked configuration in which the first and second arms are engaged with the humeral head. The method can also include unlocking the first arm with respect to the second arm to permit adjustment of a position of the first arm with respect to the second arm, thus placing at least one of the first or second arms in an unlocked configuration. The actions of locking and/or unlocking can be performed with a single digit.

The method can also include inserting at least one bone pin into at least one of the humeral head or the humerus to help fixate a location of the resection guide with respect to the humeral head. In at least some such embodiments, inserting at least one bone pin into at least one of the humeral head or the humerus can include inserting an inferior bone pin below a subscapularis tendon proximate to the humeral head and through a slot formed in the second arm. The action of inserting at least one bone pin into at least one of the humeral head or humerus can include inserting a superior bone pin through a rotator interval proximate to the humeral head and through a slot formed in the first arm. The superior bone pin can be tangent to a superior portion of the resecting plane to extend a resecting surface along which a cutting tool performing the resecting the humeral head passes to an opposite side of the bone being resected.

Any of the methods provided for above or otherwise herein can be performed with a subscapularis tendon being intact during an entirety of the method. In at least some such embodiments, each of the first arm and the second arm can be inserted to the perimeter of the humeral head at least one of superior to the intact subscapularis tendon or inferior to the intact subscapularis tendon. The method can also include manipulating the subscapularis tendon to increase visibility by moving it away from its natural location while keeping it intact.

Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF DRAWINGS

This disclosure will be more fully understood from the following detailed description taken in conjunction with the accompanying drawings, in which.

DETAILED DESCRIPTION

Figure 1A:
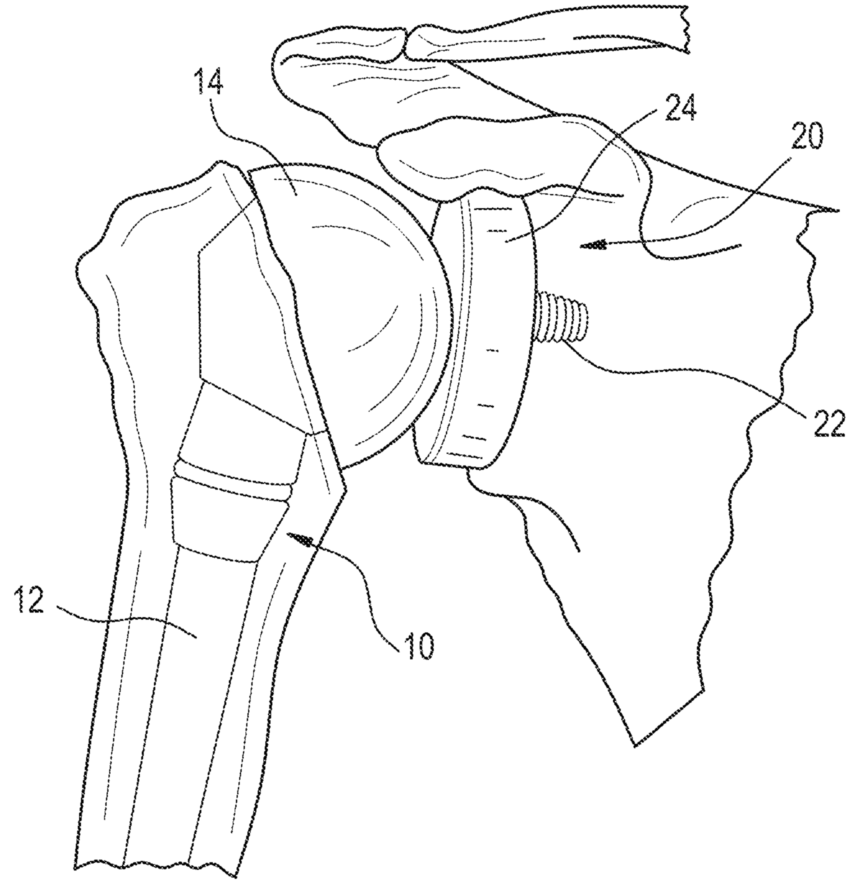
FIG. 1A PRIOR ART
FIG. 1A is a side, partially translucent view of one example of an anatomic shoulder joint reconstruction, including an anatomic glenoid implant of the prior art coupled to a scapula.

Certain embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting embodiments and that the scope of the present disclosure is defined solely by the claims. The features illustrated or described in connection with one embodiment may be combined with the features of other embodiments. Such modifications and variations are intended to be included within the scope of the present disclosure. Accordingly, aspects and features of every embodiment may not be described with respect to each embodiment, but those aspects and features are applicable to the various embodiments unless statements or understandings are to the contrary. Further, to the extent portions of a human anatomy are illustrated, but other portions of the anatomy in that same region are not explicitly illustrated, a person skilled in the art will appreciate the location of the omitted anatomies. In at least some instances the omitted anatomies are not included to improve visualization for the provided explanations and illustrations. A person skilled in the art will still understand how the devices and methods provided for herein can interact with such omitted anatomies without requiring specific illustration of the same.

While in some embodiments movement of one component and/or portion of the body is described with respect to another, a person skilled in the art will recognize that other movements are possible. Additionally, a number of terms may be used throughout the disclosure interchangeably but will be understood by a person skilled in the art. By way of non-limiting example, the terms subscapularis, subscapularis tissue, subscapularis tendon, subscapularis muscle, and other variations of the same, may be used interchangeably with one another, and to the extent some such terms do not appear, they are encompassed by use of the others. By way of further non-limiting examples, the terms "prosthesis" and "implant" may be used interchangeably with one another, and the terms "cut" and "resect" (and other forms thereof, e.g., cutting and resecting) may be used interchangeably with one another.

To the extent the present disclosure describes "coupling," "mating," or uses other similar terms as it relates to having an instrument or tool contact part of a patient's anatomy, such as bone, the term includes engagement or contact between the instrument or tool and the part of the patient's anatomy, and does not necessarily require any securing or attaching relationship between the two unless otherwise indicated or understood by a person skilled in the art to inherently create a secured/attached relationship and/or for such securement/attachment to be required for proper performance. Further, to the extent that linear or circular dimensions are used in the description of the disclosed devices, components, systems, and methods, such dimensions are not intended to limit the types of shapes or sizes of such devices, components, and systems, etc. A person skilled in the art will recognize that an equivalent to such linear and circular dimensions can be easily determined for any geometric shape (e.g., references to widths and diameters being easily adaptable for circular and linear dimensions, respectively, by a person skilled in the art). To that end, to the extent the term "circumference" is used, a person skilled in the art will appreciate a "perimeter" or "edge" is an equally acceptable term to use to the extent an equivalent of what is being described is not circular.

Sizes and shapes of the components of the humeral resection guides and related components can depend, at least in part, on the sizes and shapes of the other components with which the guides and related components are being used, the anatomy of the subject being operated on, and the type of procedure being performed. Still further, to the extent features, sides, or steps are described as being "first" or "second," such numerical ordering is generally arbitrary, and thus such numbering can be interchangeable. Similarly, the order in which actions are presented in claims is by no means limiting. While terms like "proximal" and "distal" as used herein, they are primarily used as a point of reference for describing two portions or ends of an instrument, tool, component, device, system, location in a body, etc. Accordingly, no meaning should be attributed to a specific location with respect to "proximal" or "distal" beyond distinguishing one side from another unless explicitly indicated. For example, what is referred to herein as a proximal portion or end may be considered distal in operation, and thus, likewise, what is referred to herein as a distal portion or end may be considered proximal in operation.

In the present disclosure, like-numbered components of various embodiments generally have similar features when those components are of a similar nature and/or serve a similar purpose, unless otherwise noted or otherwise understood by a person skilled in the art. To the extent terms like "approximately," "about," and "substantially" are used herein, a person skilled in the art will appreciate the scope those words convey in the context of their usage. During a surgical procedure, obtaining a certain degree of placement, a certain distance, and/or a certain alignment, among other positioning and the like may be difficult, and thus use of terms like "approximately," "about," and "substantially" is intended to address this difficulty. A person skilled in the art will understand what constitutes how close a particular dimension or placement should be to still fall within the spirit of the quantification and description provided for herein. Even in instances where such terminology is not used, and a dimension or placement just includes the number or placement term (e.g., "parallel" is used instead of "substantially parallel"), a person skilled in the art will appreciate that, unless explicitly indicated otherwise, terms like "approximately," "about," and "substantially" are applicable to those dimensions and placements as well. The foregoing notwithstanding, a person skilled in the art will appreciate that terms like "approximately," "about," and "substantially" at least encompass dimensions that are ±10%, 10°, etc. of the provided amount, or encompass dimensions that are ±5%, 5°, etc. of the provided amount, unless indicated otherwise or otherwise known to those skilled in the art. The present disclosure appreciates that a person skilled in the art, in view of the present disclosure, understands suitable placements for various features of the disclosed systems, devices, instrumentation, and/or implants, and related components of any of the same, and thus to the extent a particular placement or location is described, unless it is explicitly indicated that placement or location is required, a person skilled in the art will appreciate other placements or locations that are possible without impacting the overall procedure(s).

Relevant Anatomy for Humeral Resecting Procedures

Figure 1B:
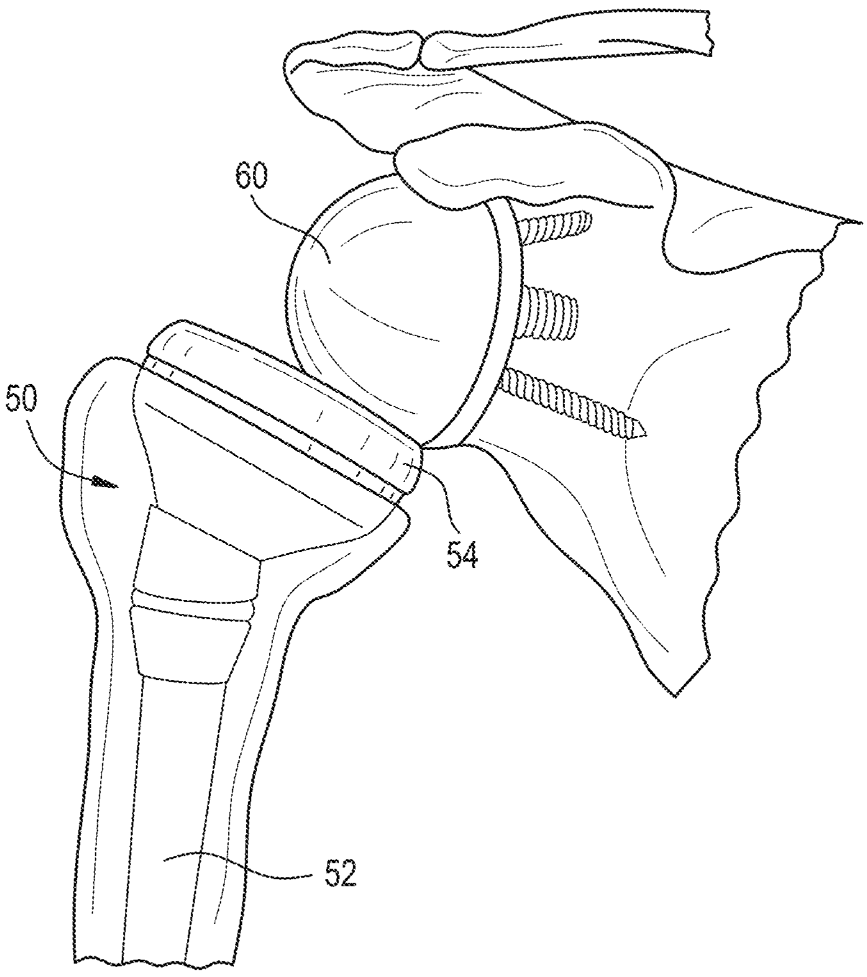
FIG. 1B PRIOR ART
FIG. 1B is a side, partially translucent view of one example of reverse shoulder joint reconstruction, including a reverse glenoid implant of the prior art coupled to a scapula.

The present disclosure relates to devices and methods for preparing a humeral head to receive a prosthesis, and more particularly devices for assisting in cutting or resecting the humeral head, such as an entire humeral head or at least a portion of the humeral head, so that it can receive the prosthesis. Embodiments of a surgical guide, described as a humeral resection guide or a humeral cut guide, are disclosed herein that can be used to resect a humeral head prior to replacing the resected portion with an implant and/or prosthetic, also referred to as a prosthetic implant. The humeral prosthesis and/or implant can be, for example, a humeral head prosthesis, like the prosthesis 10 of FIG. 1A that includes a convex humeral head 14, which is intended to mimic an anatomically correct humeral head in an anatomic shoulder arthroplasty procedure. The prosthetic convex humeral head 14 is then received by a concave receiver prosthesis, like the prosthesis 24 of FIG. 1A. Alternatively, the humeral implant or prosthesis can be, by way of further example, a concave receiver humeral prosthesis, like the prosthesis 50 of FIG. 1B that includes a concave receiver surface 54, which is intended to mimic a glenoid surface formed on the humerus to receive a prosthetic head component associated with the glenoid, like the convex prosthetic head 60 of FIG. 1B, as used in a reverse shoulder arthroplasty procedure. Although the prosthesis 10 of FIG. 1A includes a stem, as provided for herein, in other instances the equivalent implant or prosthesis to the prosthesis 10 can be stemless.

Whether installing an implant(s) and/or prosthesis(es) for an anatomic or reverse shoulder procedure, an accurate cut of the bone to prepare it to receive the implant(s) and/or prosthesis(es) is important. The humeral resection guides of the present disclosure enable accurate cuts. Further, the guides include various features that allow the guides to be used in smaller spaces, such as procedures performed using tissue sparing techniques that do not detach the subscapularis tendon from its natural attachment points. In other words, the subscapularis remains intact during the procedure. The foregoing notwithstanding, the instrumentation and techniques provided for herein can be used for training and/or with more traditional procedures in which the subscapularis is detached. More generally, the disclosed humeral resection guides are attached to a humerus, such as at a humeral head and/or to bone proximate to the humeral head, and set a desired path for cutting. The desired path is designed to create a surface onto which the implant(s) and/or prosthesis(es) can be secured. The humeral resection guide defines a cutting or resecting plane across which a cutting tool (e.g., a sagittal saw) is designed to run through, cutting away the humeral head and leaving behind an attachment surface (referred to herein as a "humeral resection surface") to which the implant(s) and/or prosthesis(es) is coupled The present disclosure provides for tissue sparing procedures to be performed in which the subscapularis tendon remains intact throughout the procedure. Maintaining attachment of the subscapularis tendon means there is more limited space to perform procedures, and the devices, tools, and systems disclosed herein allow for the same types of procedures to be performed (e.g., shoulder arthroplasty) while causing less harm and damage to tissue and the surrounding anatomy. In some embodiments, such as when a tight joint is involved, a portion of the subscapularis tendon may be cut or sacrificed to increase access to the joint. This may entail, for example, cutting a top of the subscapularis tendon a few millimeters, with it being able to be sutured back after having gained sufficient access to perform the procedure(s). By way of further example, about 10% or less of the subscapularis may be sacrificed while about 90% or more of the subscapularis can remain intact. Instances where a portion of the subscapularis tendon, and/or other tendons, are cut or sacrificed can still be considered tissue sparing with respect to the present disclosures, and are still considered to involve the subscapularis being intact. In other words, "intact" does not have to mean fully intact, it can include anything less than fully intact and/or can encompass the subscapularis tendon being "substantially intact," where "substantially intact" can include any instance when 20% or less of the subscapularis is scarified, or when 15% or less of the subscapularis is scarified, or when 10% or less of the subscapularis is scarified.

Figure 2:
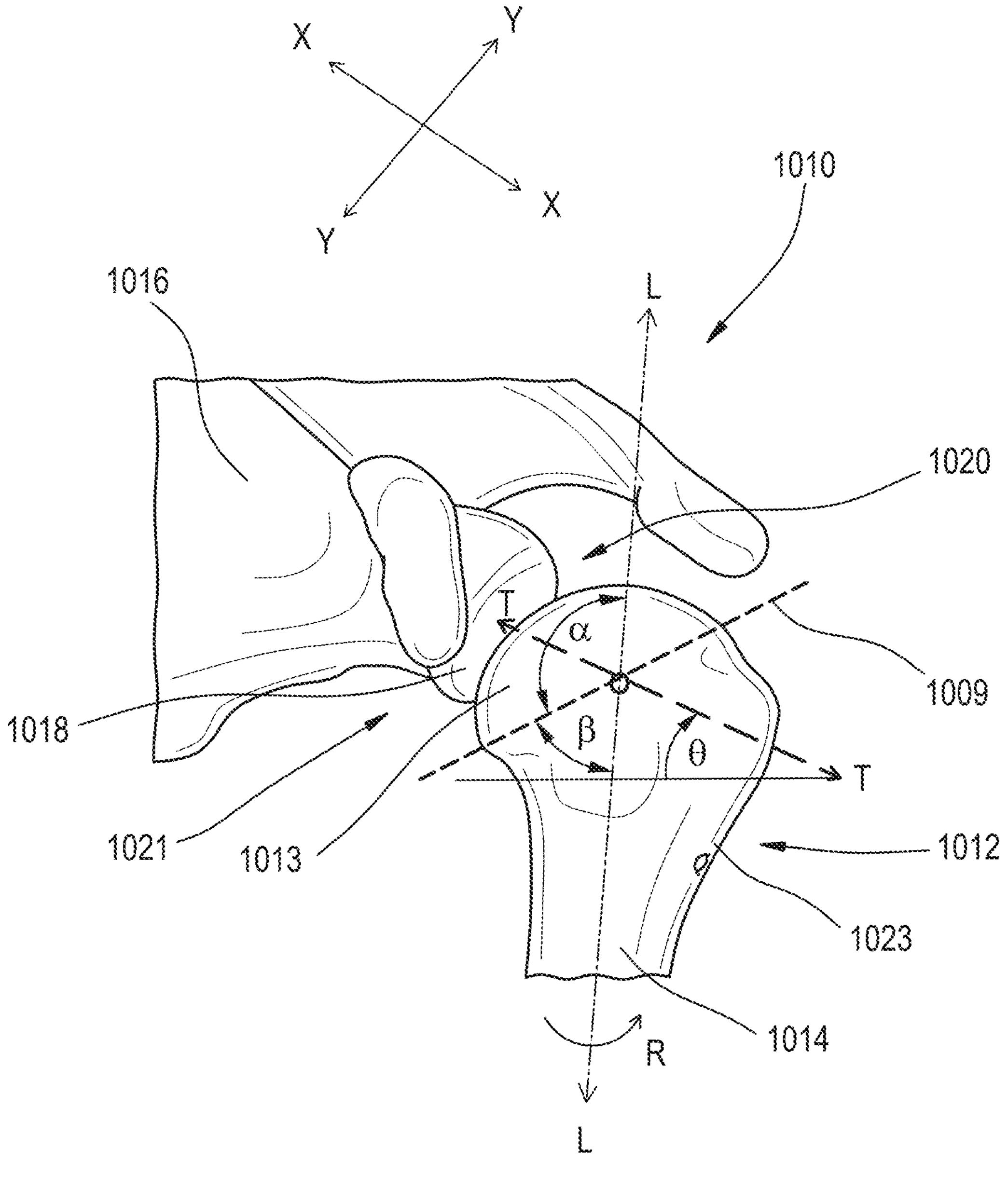
FIG. 2 is a perspective view of a human glenohumeral shoulder joint, and associated joint space, including a humerus having a humeral head and an elongate shaft.

A patient's glenohumeral joint 1010, which is part of a shoulder region of a patient, is illustrated in FIG. 2. The glenohumeral joint 1010 is also referred to herein as the joint space 1010 or shoulder joint 1010, among other names. The natural shoulder joint 1010 includes a humerus 1012 and a scapula 1016. The humerus 1012 includes a generally convex head 1013, referred to herein as the humeral head, an elongate shaft 1014, and a lateral cortex 1023, also referred to as a lateral surface in some instances. As shown the humeral head 1013 has a generally circular cross-sectional area, although in other instances it can be considered elliptical or other shapes. The natural angle α of inclination of the humeral head 1013 relative to the shaft 1014 in most humans is approximately in the range of about 125° to about 145°, and in some instances can be about 135°, the angle α being defined by a longitudinal axis L of the shaft 1014 and an articular margin 1009 where the humeral head 1013 meets the elongate shaft 1014 of the humerus 1012. The angle R is approximately in the range of about 350 to about 550 and forms a linear pair with the natural angle of inclination α, which defines the longitudinal axis L of the shaft 1014. The humeral head 1013 can also have an angle of retroversion 0, which is defined as the angle of rotation in the transverse plane or the Z plane as illustrated. The natural retroversion angle θ in most humans is approximately in the range of about 0° to about 30°. The scapula 1016 includes a concave surface or glenoid 1018. During movement of the shoulder joint 1010, the humeral head 1013 articulates within the glenoid 1018 of the scapula 1016. If the natural shoulder joint 1010 suffers a traumatic injury or degenerative changes, a surgeon may replace either or both the naturally convex humeral head 1013 and the glenoid 1018 with prosthetic components, using either an anatomic or reverse procedure, as detailed above.

Although not illustrated, a person skilled in the art will understand that a subscapularis tendon extends from the scapula 1016 to the humerus 1012, and that in a tissue sparing procedure in which the subscapularis tendon is not detached from the humerus (i.e., the subscapularis tendon remains intact), the subscapularis tendon can be manipulated to improve visibility to a surgical site, such as by using displacement wrap that is disposed around at least a portion of the subscapularis tendon and is tensioned in a manner that causes the tendon to be moved inferiorly or superiorly. Non-limiting examples of such a wrap are disclosed in U.S. Patent Application Publication No. 2024/0108433, entitled "Devices and Methods for Minimizing Damage to Soft Tissue during a Surgical Procedure," the content of which is incorporated by reference herein in its entirety.

Additional tools, such as a double bent Hohmann retractor (s), posterior cuff retractor(s) (e.g., twisted Hohmann retractor(s)), anterior subscapularis retractor(s) (e.g., right angle Hohmann retractor(s)), inferior subscapularis retractor(s) (e.g., subscap Hohmanns retractor(s)), and/or other types of retractor(s) (e.g., double bent Hohmann retractor(s)), including retractors designed for use from a right side and/or a left side of a patient, can be used to further manipulate surrounding soft tissues. Even when a displacement wrap and/or other tools are utilized, however, the amount of space created is typically insufficient for traditional bone preparation instruments and/or tools, such as humeral resection guides, to be used to perform various bone preparation actions, such as cutting. In such instances, typically a rotator interval 1020, which can be defined between the superior border of the subscapularis and the anterior border of the supraspinatus, provides a first, superior entry point for accessing the humeral head 1013, and an inferior border 1021 of the subscapularis, which can be defined as the lower inferior border of the subscapularis at the lever of the anterior circumflex vessels (i.e., the "Three Sisters"), provides a second, inferior entry point for accessing the humeral head 1013.

In addition to the disclosed procedures being able to be performed while keeping the subscapularis intact and/or without resecting the subscapularis, and the present devices and systems allowing for the same, the present disclosure also allows for the disclosed procedures to be performed without having to externally rotate the humerus to allow access to the joint space. To the contrary, the present procedures, devices, and systems enable the humerus to not be distracted from its joint during the surgical techniques provided for herein.

During surgery to replace the humeral head 1013 in an anatomic arthroplasty procedure, or remove the humeral head 1013 so that a humeral prosthesis that mimics a receiving surface of the glenoid in a reverse arthroplasty procedure, an initial, or at least early, step in the procedure is to resect the humeral head 1013. This is typically done in a manner that leaves a flat planar surface onto which the prosthesis is eventually secured for use as an implant. The resection or cut is generally made at the articular margin 1009. Thus, a cutting or resecting plane (also referred to as a cut plane, among other terms) for the procedure is typically aligned with the articular margin 1009 such that illustration of the articular margin 1009 can double as an illustration of the cutting plane. As shown, the articular margin 1009 is substantially aligned with the natural angle $\alpha$ of inclination such that the cutting plane will be at the natural angle $\alpha$ of inclination, allowing the anatomy to be properly mimicked. A person skilled in the art will appreciate that to the extent the implant(s) used alters what would otherwise be the natural angle $\alpha$ of inclination, the resection or cut, and thus the resulting humeral resection surface and cutting plane, can be made at a different angle than what is illustrated as the articular margin 1009. This different angle along which the cutting plane is formed can be one that is planned to account for impact caused by the implant(s) such that, when the implant(s) are secured to the resulting humeral resection surface, the resulting angle formed mimics the natural angle $\alpha$ of inclination.

Although the present disclosure is often described herein as being applicable to tissue sparing procedures in which the subscapularis tendon remains intact, a person skilled in the art will appreciate that the devices, systems, and techniques described herein can also be used in conjunction with procedures in which the subscapularis tendon is detached from the humerus.

Traditional resection guides used to create a cutting or resecting plane as part of a shoulder arthroplasty procedure rely on the adequate visibility of the articular margin and access to the joint space provided by removing the subscapularis tendon and externally rotating the convex humeral head 1013 out of the glenoid surface 1018 to perform this cut. Thus, for tissue-sparing procedures, as well as other types of procedures performed in more limited space and/or with more limited displacement of tissue and the like, humeral resection guides of the nature provided for herein are necessary.

First Embodiment of a Humeral Resection Guide and Related Components

FIGS. 3A-3C and 4-6 illustrate an embodiment of a humeral resection guide 100, also referred to as a humeral cut guide, a resection guide, or a cut guide. Generally, the guide 100 is designed in a manner that it can securely grasp the humeral head, set a cutting or resecting plane, and help guide a cutting tool along the cutting plane to resect the humeral head and form a planar surface on the proximal portion of the humerus (referred to herein as the "humeral resection surface") onto which an implant and/or prosthesis can be coupled. These actions of the guide 100 can be performed in the narrow glenohumeral joint space while the subscapularis tendon is still attached to the humerus. The illustrated embodiment, as with at least some other embodiments provided for herein, is for use in a left shoulder procedure, the "left" typically referring to the operative side of the patient. A person skilled in the art, in view of the present disclosures, will understand how a resection guide for a right shoulder procedure would be configured in view of the present disclosures.

The resection guide 100 can include a superior radial arm 110 and an optional resection guide extender 120, the superior radial arm 110 being the portion of the guide 100 designed to enter a joint space and engage a humeral head, and/or anatomy adjacent or proximate to the humeral head (e.g., other portions of the humerus), to set a desired cutting or resecting plane or angle. The superior radial arm 110 can be configured (e.g., sized, shaped, and have particular features illustrated and/or described herein) to enter the narrow joint space known as the rotator interval, which is superior to the subscapularis and inferior to the supraspinatus. Further, the guide extender 120, also referred to as an inferior extender or inferior arm, can be configured (e.g., sized, shaped, and have particular features illustrated and/or described herein) to extend the resecting or cutting plane defined by the superior radial arm 110 inferior to the subscapularis tendon to achieve a "patient specific anatomic" resection. The arm 110 and the guide extender 120 in the illustrated embodiment are two distinct and separate components. The guide extender 120 can be optionally coupled to a proximal portion **110*p* of the superior arm 110. More particularly, a slot 130 formed in the proximal end of the superior radial arm 110*p* can receive protrusion 132 formed on the guide extender 120. The slot 130 and protrusion 132 are merely one example of a coupling mechanism that can be used to mate the guide extender 120 to the superior radial arm 110, and other components known to those skilled in the art can be used to removably mate the superior radial arm 110 and extender 120**.

The resection guide 100 can also include a vertical alignment plate 140, which can be integrally formed with or coupled to the superior radial arm 110, for example by a weldment or a press fit, between the two components. As shown, the vertical alignment plate 140 extends distally from the superior radial arm 110. A length of the vertical alignment plate 140 forms an angle α' with the superior radial arm 110, and more particularly a top or superior surface 110*s* of the superior radial arm 110. By aligning the vertical alignment plate 140 with the longitudinal axis L of the elongate shaft 1014 of the humerus 1012, and having the angle α' match the natural angle α of inclination, a resecting plane defined by the X-Y plane of the superior radial arm 110 can be aligned with the cutting plane illustrated by the articular margin 1009 in FIG. 2. Accordingly, a cutting or resecting plane defined by the resection guide 100 (see cutting plane CP in FIGS. 5B and 6) can likewise have an angle α' approximately in the range of about 125° to about 145°, for example 135°, a cutting or resecting plane angle ω (see FIGS. 5B and 6) being defined by the angle α' formed by the vertical alignment plate 140 and the superior radial arm 110 as shown. Accordingly, the angle α' defined by the length of the alignment plate 140 and the superior surface 110*s* of the superior radial arm 110 defines the resecting plane angle ω, and in the illustrated embodiment, the angle α' is congruent with the resecting plane angle ω. A person skilled in the art will appreciate that in other configurations it may be possible for the angle α' to define the resecting plane angle ω without the angles being congruent.

A counterpart angle β', as shown, can likewise have similar values as the counterpart angle R described above. In the illustrated embodiment, the angle R is not adjustable, although in other embodiments, including modification of the illustrated embodiment, it can be. By aligning the vertical alignment plate 140 with the long humeral bone, that sets the desired the location of the superior radial arm 110 and guide extender 120. That is, rotating or otherwise moving the vertical alignment plate 140 can effectively change the angle of inclination of the resecting plane with respect to the humerus because it changes the positioning of the superior radial arm 110 and a coupled inferior extender 120 with respect to the humeral head. In some instances, the vertical alignment plate 140 can be considered its own component that can be selectively attached and detached to the guide 100, while allowing angular rotation to optimize the cut angle α' in at least some instances, while in other instances it can be considered as part of the guide 100 and/or as part of the superior radial arm 110. Any known technique for coupling two components can be utilized to couple the vertical alignment plate 140 with the superior radial arm 110.

As shown, an opening 142 can be formed through an outer, planar surface of the vertical alignment plate 140 and extend to an opposing planar surface of the vertical alignment plate 140. The opening 142 can be used, for example, to receive a version handle 150, also referred to as a handle, for use in checking and/or adjusting a version alignment of the resection guide 100, and thus the opening can be considered a handle-receiving opening. An embodiment of the handle 150 that can be coupled to the alignment plate is discussed herein with respect to FIG. 5A. The version handle 150 can assist with providing both version alignment and humeral shaft alignment. Version alignment takes into account retroversion and/or anteversion, as understood by those skilled in the art in view of the present disclosures. More particularly, the version alignment capabilities of the present disclosure allows a surgeon to rotate the guide 100 and check angular alignment with a foreman of the patient using the handle 150 coupled to the alignment plate 140. The surgeon can either match exact patient anatomy as desired, or use this version angular alignment check to set the version to a desired value based on other patient factors, such as existing range of motion with the contralateral arm. The illustrated version handle 150 can be considered a 30° version handle because it can be used to set an approximately 30° of retroversion angle. This angle allows a surgeon to visually approximate and set the desired retroversion angle, which can sometimes be approximately in the range of about 20° to about 40°, with the illustrated embodiment providing for a 30° angle. A person skilled in the art will appreciate other features besides an opening 142 can be used to removably couple the handle 150 (or other configuration (s) of a handle) or other tool to the alignment plate 140.

Figure 3A:
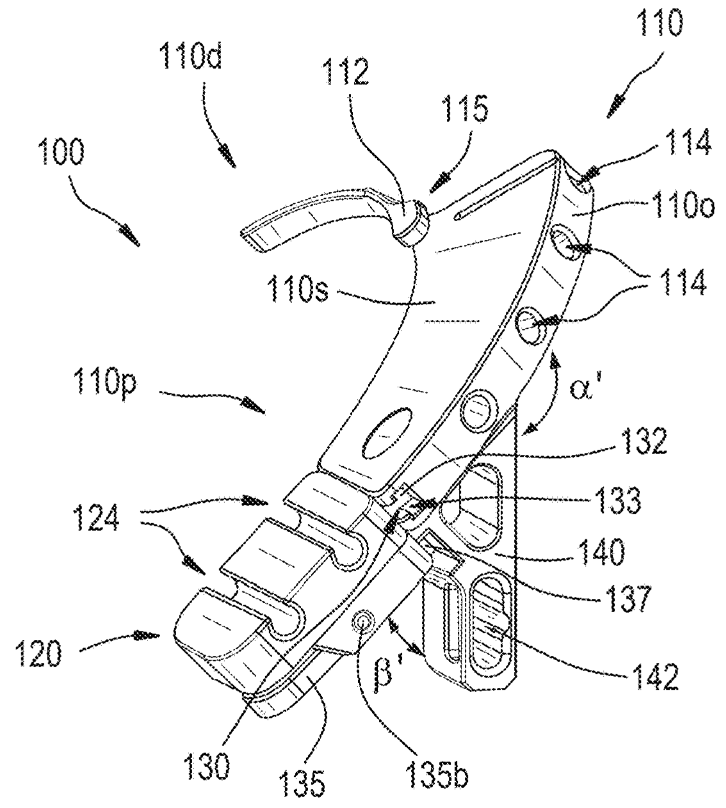
FIG. 3A is a side perspective view of one embodiment of a humeral resection guide having a guide extender coupled thereto.
Figure 3B:
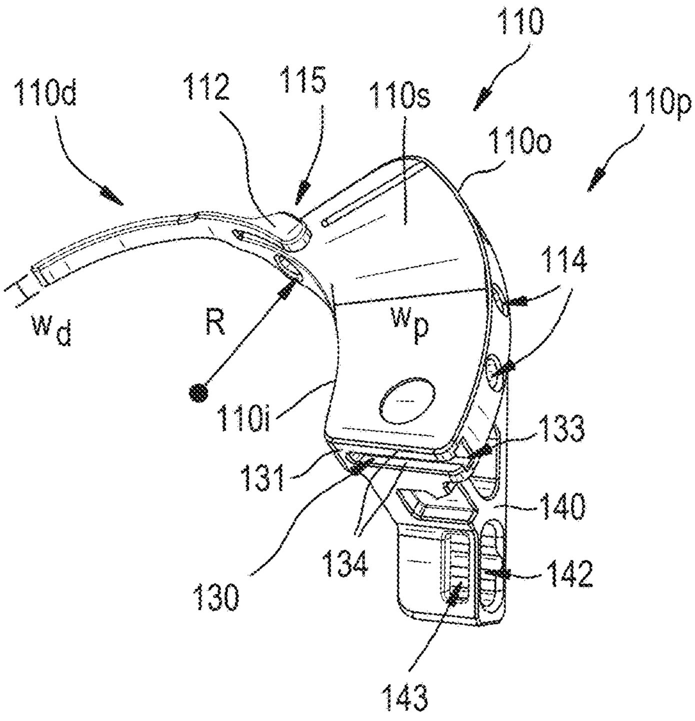
FIG. 3B is a front perspective view of the humeral resection guide of FIG. 3A.
Figure 3C:
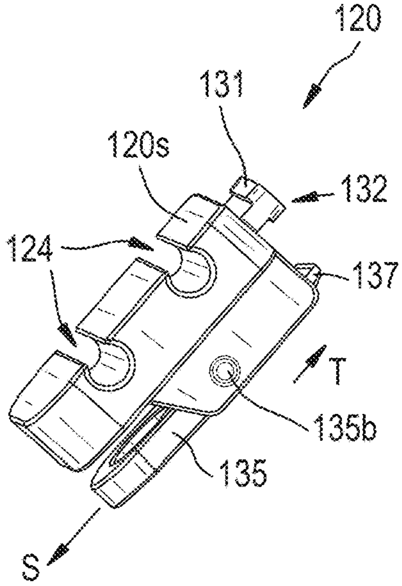
FIG. 3C is a side perspective view of the guide extender of FIG. 3A.

FIGS. 3B and 3C illustrate the superior radial arm 110 and the guide extender 120 of the humeral resection guide. The superior radial arm 110, shown in FIG. 3B, includes a proximal portion 110*p* and an elongated distal portion 110*d*, sometimes referred to as a distal member. As noted above, in use, what is referred to herein as the proximal portion 110*p* may be considered distal in operation, and thus, likewise, what is referred to herein as the distal portion 110*d* may be considered proximal in operation. The proximal portion 110*p* is configured for receiving one or more bone pins, and, in at least some instances, for coupling to or otherwise mating with the guide extender 120. As shown, a connection feature 130 is formed as part of the proximal portion 110*p* to aid in the mating. The connection feature 130 in the illustrated embodiment is a slot 130 that extends from a closed terminal end 131 proximal to an inner surface 110*i* of the arm to an opposed opening 133 formed in an outer surface 110*o* of the superior radial arm 110. The slot 130 includes two opposed ledges 134 that define sidewalls of the slot 130 between the closed terminal end 131 and the opening 133. The ledges 134 and the slot 130 are able to receive the protrusion 132 of the guide extender 120 through the opening 133.

Also formed in the proximal portion 110*p* can be one or more bone or guide pin receiving holes or openings 114. The openings 114 can be formed in the proximal portion 110*p* extending from the outer surface 110*o* of the proximal portion 110*p* to an inner surface 110*i* of the proximal portion 110*p* for the purpose of receiving one or more bone pins, drill bits, or other similar structures that can engage the humeral head, and/or bone surrounding the humeral head, to help hold the arm 110, and thus the guide 100, at a location or position with respect to the humeral head. The location of the openings 114 can be non-parallel, and further can be such that pin placement occurs above or below the subscapularis tendon (within a bicipital groove location), thus preventing any pin(s) disposed therein from passing through the tendon. More particularly, one or more of the openings 114 can be disposed in a manner such that a drill bit or bone pin that passes therethrough can be below the resecting plane defined by the arm 110 to prevent interference with the cutting surface or cutting tool (e.g., cutting tool 102, discussed below) that is used to cut and/or resect the humeral head. As shown in FIG. 3B, the plurality of openings 114 are disposed along the curvature of the proximal portion 110*p* at various angular positions, meaning the openings 114 are non-parallel. Any number of openings 114, including one or more than two, can be used to secure the arm 110 to the humeral head. The foregoing notwithstanding, it can be beneficial for the openings 114 to align with the resecting plane such that longitudinal axes extending through a length of the openings 114, and a length of pins disposed therein, can be parallel or substantially parallel to, the resecting plane.

The distal portion 110*d* of the superior radial arm 110 can be configured to engage the humeral head, and/or bone proximate to the humeral head, to help set a location of the resection guide 100 with respect to the humeral head in conjunction with defining the resecting plane. More particularly, the distal portion 110*d* can have a generally arcuate shape with an inner, contoured surface 110*i*' configured to help grip or otherwise engage bone. The distal 110*d* and proximal portions 110*p* together can have a general radius of curvature R designed to fit a natural (or considered normal amongst a designated population for that particular arm 110) curvature around the humeral head.

As shown, this same radius of curvature R can also be formed with proximal portion 110*p* of the arm 110, while in other embodiments a different radius of curvature can exist for the distal portion 110*p* and the proximal portion 110*p*. In some embodiments, the distal portion 110*d* can include one or more gripping protrusions or teeth disposed on the inner surface 110*i*, which can help to better grasp and hold the surface of the humeral head and/or bone proximate to the humeral head. Gripping protrusions or teeth can likewise be placed along any portion of the inner surface 110*i* of the superior radial arm 110.

The superior surface 110*s* of the superior arm 110 can be substantially flat, thus allowing a cutting tool to pass smoothly along the cutting or resecting plane/surface defined by the resection guide 100. The substantially flat planar surface defined across the superior surface 110*s* of the superior arm 110 also helps reduce possible trauma to soft tissue as the arm 110 is inserted to a surgical site. As shown, a width $w_d$ of the distal portion 110*d* of the arm 110 is typically substantially smaller than a width $w_p$ of the proximal portion 110*p* of the arm 110 at least because it is the distal portion 110*d* that is primarily inserted into the surgical site and is the portion that has to extend furthest into the body, thus likely having to navigate through the most tissue. As shown in FIGS. 3A-3B, and as also shown at least in FIG. 4, a portion (as shown, a proximal portion) of the distal portion 110*d* can extend over the superior surface 110*s* of the proximal portion 110*p* to form a ledge 112 defining a guide slot 115, also referred to as a mini mail slot, between the ledge 112 and superior surface 110*s*. The guide slot 115 is configured to guide a cutting blade used to resect the humeral head. More particularly, the guide slot 115 can receive a blade or cutting instrument while the ledge 112 maintains the cutting instrument parallel to the superior surface 110*s* or intended cutting surface. The guide slot guides the cutting instrument along the resecting plane while cutting the humeral head, and keeps the cutting instrument parallel, or substantially parallel, to the resecting plane.

The guide extender 120, shown in FIGS. 3A and 3C, includes a proximal end 120*p*, and distal end 120*d*. The proximal end 120*p* is configured for coupling to or otherwise mating with the superior radial arm 110 as shown in FIG. 3A. The extender 120 can be used to extend the cutting or resecting plane inferiorly to assist in achieving a "patient specific anatomic" resection. A person skilled in the art appreciates what an anatomic resection is, and thus a further explanation of the same is unnecessary. A connection feature 132 is formed as part of the proximal portion 120*p* to aid in the mating, the connection feature 132 including a protrusion with a ridge 131. The protrusion 132 and ridge 131 are configured to pass through the opening 133 and into the slot 130 formed in the proximal end of superior radial arm 110*p* such that the ledges 134 of the slot 130 capture the ridge 131 within the slot 130. Further, a ball plunger or lever 135 can be provided to assist in selectively locking and unlocking the extender 120 from the superior arm. For example, in the illustrated embodiment, the lever 135 can be biased, for example by a spring bias, in a direction T, which is towards the superior radial arm 110 in FIG. 3A. As a result, in use with the superior radial arm 110 and the vertical alignment plate 140, the extender 120 is biased into a locked position in which a tip 137 of the lever 135 can engage a surface of the alignment plate 140. In use, the lever 135 can be depressed or otherwise moved in a direction S, opposite to the direction T, by applying a force in the direction S, causing the tip 137 to move away from the vertical alignment plate 140 such that the extender 120 is in an unlocked position with respect to the vertical alignment plate 140, and thus the superior radial arm 110, and the connection feature 132 can slide with respect to the slot 130. In at least some embodiments, the button 135*b* can be depressed to assist in unlocking the lever 135. When the extender 120 is mounted at a desired location with respect to the vertical alignment plate 140, and thus the superior radial arm 110, the force applied in the direction S can be released, thus causing the lever 135 to be biased in the direction T and the tip 137 to engage the vertical alignment plate 140. When the tip 137 engages the vertical alignment plate 140, an audible click or the like can be heard to notify the user that the extender 120 is properly mated to the vertical alignment plate 140, and thus the superior arm. As shown, a button 135*b* can also be included as part of the lever 135, the button being configured to assist in selectively locking and unlocking movement of the lever 135. For example, pressing the button 135*b* inwards, towards the extender 120, can help unlock the lever 135 to allow movement thereof, and releasing the button 135*b* can cause the button 135*b* to be biased away from the extender to return the lever 135 to a locked configuration.

One or more bone or guide pin receiving grooves or openings 124, which can be referred to as inferior grooves or openings among other names, can be formed in the superior surface 120*s* of the extender 120. The openings 124 can be for the purpose of receiving one or more bone pins, drill bits, or other similar structures that can engage the humeral head, and/or bone surrounding the humeral head, to help hold the extender 120, and thus the guide 100, at a location or position with respect to the humeral head. The location of the grooves 124 can be such that pin placement occurs above or below the subscapularis tendon, thus preventing any pin(s) disposed therein from passing through the tendon. In some embodiments, depending on patient anatomy, the pin(s) may be passed through the tendon or soft tissue to achieve a desired pin(s) angle for adequate fixation of the extender 120. As shown the two grooves 124 are parallel, or substantially parallel, to each other, and are also disposed approximately along or parallel to the X axis (although other configurations, including fewer slots, e.g., one slot, are possible). Further, any number of grooves 124, including one or more than two, can be used, and when multiple grooves 124 are used, they do not have to be parallel, or substantially parallel, to each other. The foregoing notwithstanding, it can be beneficial for the grooves 124 to align with the resecting plane such that longitudinal axes extending through a length of the grooves 124, and a length of pins disposed therein, can be aligned or substantially aligned with, or parallel or substantially parallel to, the resecting plane.

Similar to the superior radial arm 110, a superior surface 120*s* of the guide extender 120 can be substantially flat, thus allowing a cutting tool to pass smoothly along a cutting or resecting plane/surface defined by the resection guide 100. A width of the extender 120 can the same or substantially similar to the width $w_p$ of the proximal portion 110*p* of the superior radial arm 110. In the illustrated embodiment when the inferior extender 120 is coupled to the superior radial arm 110, the surface 120*s* of the extender can align with the surface of the superior arm to create a substantially flat, continuous planar surface.

The shapes and sizes of the superior radial arm 110 and guide extender 120 can vary on a variety of factors, including but not limited to the anatomy of the patient, the size and shape of the components with which the arm 110 and extender 120, and the guide 100 more generally, are being used, the type of procedure being performed, and/or the preferences of the surgeon, among other factors. For example, the extender 120 can be optionally coupled to the superior radial arm 110 to extend the resecting plane in the inferior direction. This extension can be beneficial, for example, if a "patient specific anatomic" resection angle approximately in the range of about 135° to about 155° is desired. Further, different sized arms and extenders, and other components of a guide(s) and/or used in conjunction with the guides of the present disclosure, can be provided together as a kit. While most of the components disclosed herein for the humeral resection guide 100, and the components used in conjunction with the same, can be introduced through the rotator interval 1020, in at least some embodiments the extender 120 can be introduced to the surgical site inferior to the subscapularis 1017.

Figure 3D:
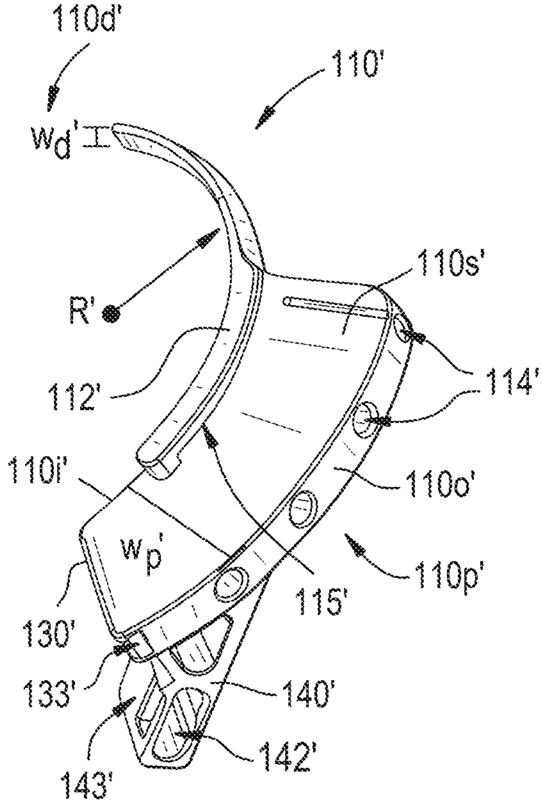
FIG. 3D is a side perspective view of another embodiment of a humeral resection guide.
Figure 3E:
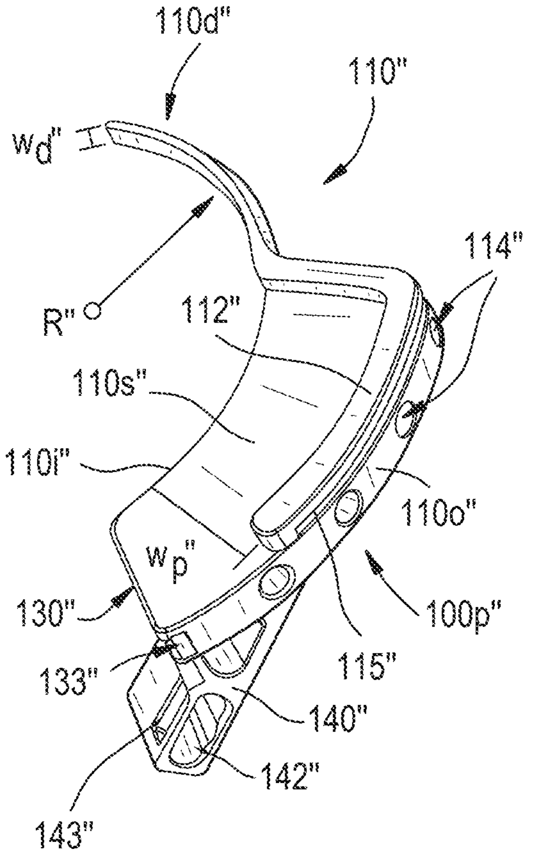
FIG. 3E is a side perspective view of still another embodiment of a humeral resection guide.
Figure 3F:
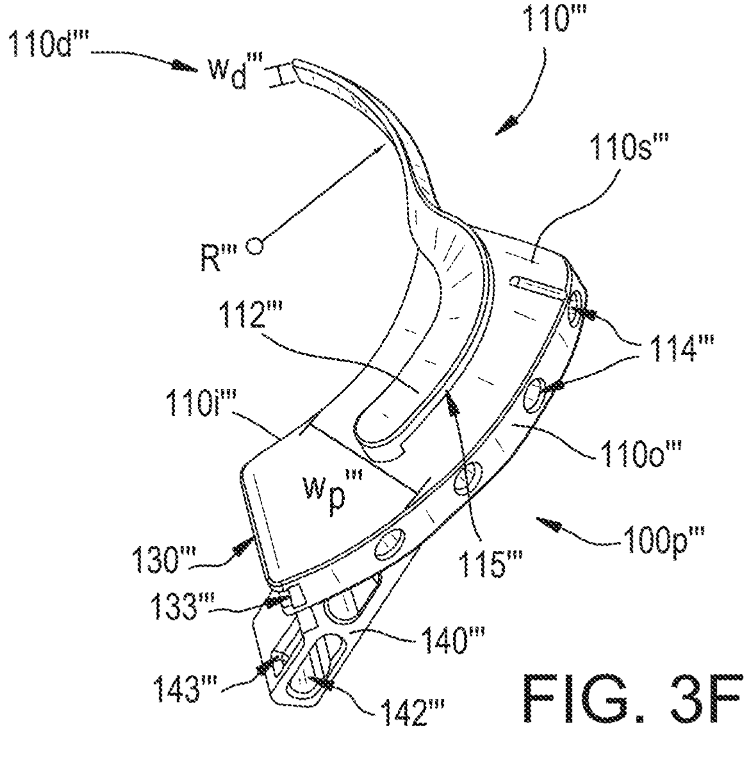
FIG. 3F is a side perspective view of another embodiment of a humeral resection guide.

FIGS. 3D-3F illustrate three alternative embodiments of superior radial arms 110', 110'', and 110''' that can be used as, or as part of, a resection guide like the guide 100. These embodiments of the radial arms 110', 110'', and 110''' are similar to the radial arm 110, and thus many of the labeled features do not require additional explanation, nor does each reference numeral illustrated need to be named explicitly herein as those skilled in the art, in view of the present disclosures, can map the reference numerals in view of the descriptions herein related to the superior radial arm 110 and associated components. For example, features like distal portions 110*d*', 110*d*'', and 110*d*''', proximal portions 110*p*', 110*p*'', and 110*p*''', and associated components thereof, can be similar unless otherwise discussed herein or visibly different in the illustrated embodiments. The same holds true for vertical plates 140', 140'', and 140''', and associated components.

A primary difference between the superior radial arms 110', 110'', and 110''' and the superior radial arm 110 is the configuration of ledges 112', 112'', and 112''', and thus the resulting configuration of guide slots 115', 115'', 115''' as compared to the ledge 112 and the guide slot 115. In each of the embodiments of FIGS. 3D-3F, the ledges 112', 112'', and 112''' are more elongate, and thus a size—at least length and volume—of the guide slots 115', 115'', and 115''' is larger as compared to the ledge 112 and the guide slot 115. This additional length and volume can provide for more ability to reach portions of the bone to be resected while still protecting surrounding tissue. As shown in FIG. 3D, the ledge 112' extends along an inner surface 110*i*' of the arm 110', the extending being radial, substantially radial, or somewhat radial in at least some instances, and thus the resulting guide slot 115' is disposed proximate to where a bone anatomy will be located when in use. In the illustrated embodiment, the ledge 112' extends over halfway along a length of the inner surface 110*i*' that is part of the superior surface 110*s*'. As shown in FIG. 3E, the ledge 112'' extends along an outer surface 110*o*'' of the arm 110'', the extending being radial, substantially radial, or somewhat radial in at least some instances, and thus the resulting guide slot 115'' is disposed proximate to a point of entry for a cutting tool with respect to the superior arm 110'', and thus the resection guide. In the illustrated embodiment, the ledge 112'' extends over halfway along a length of the outer surface 110*o*'' that is part of the superior surface 110*s*''. As shown in FIG. 3F, the ledge 112''' extends more centrally over the superior surface 110*s*'' as compared to the ledges 112' and 112''. As a result, the guide slot 115''' is more centrally located, making it closer to a location where a cutting tool is received as compared to the guide slot 115', and closer to a location where a bone anatomy to be resected will be located when in use as compared to the guide slot 115''. Similar to the ledges 112' and 112'', the ledge 112''' extends over halfway along a length of the superior surface 110*s*''' over which it is disposed.

Figure 4:
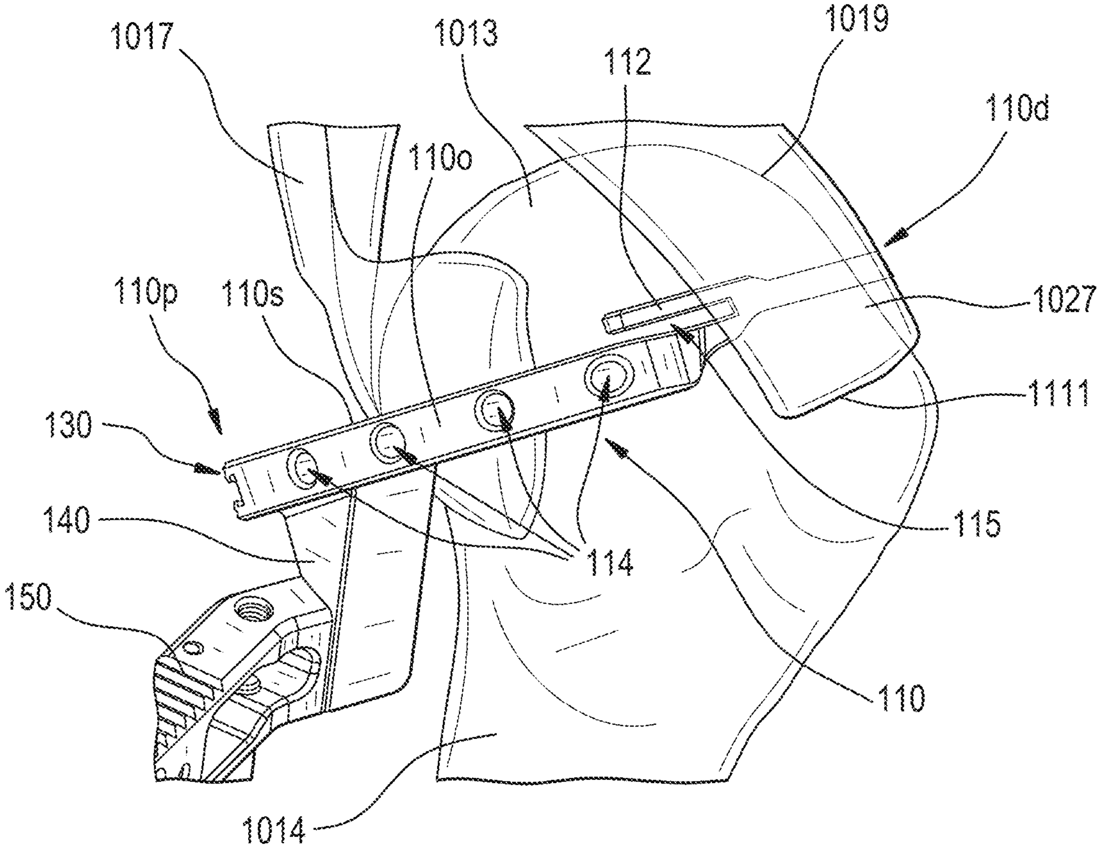
FIG. 4 is a side perspective view of the humeral resection guide of FIG. 3A disposed at the human glenohumeral shoulder joint of FIG. 2, the humeral resection guide being coupled to the humerus and having a handle coupled thereto, the subscapularis and the supraspinatus illustrated translucently.

FIG. 4 illustrates the resection guide 100 inserted into a joint space and surrounding a humeral head 1013. As shown, the distal portion 110*d* can be joined with the proximal portion 110*p* such that the distal portion 110*d* extends at a height above the superior surface 110*s* of the proximal portion 110*p* or the intended resecting plane. More particularly, the distal portion 110*d* of the superior arm 110 wraps around, or can be described as being proximate to, a substantial portion of the humeral head 1013.

Figure 5A:
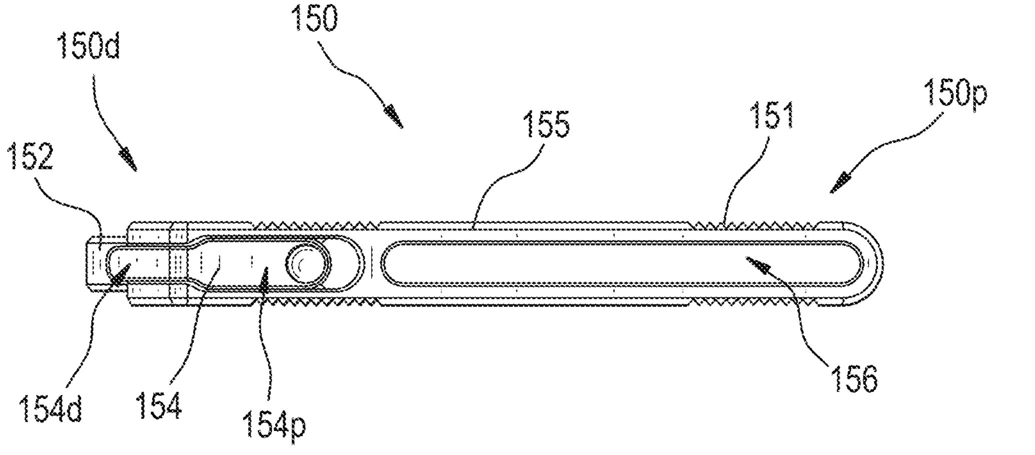
FIG. 5A is a side view of the handle of FIG. 4.

FIG. 5A illustrates an embodiment of a handle 150, also referred to as a version handle, that can be coupled to the alignment plate 140 of the superior radial arm 110. The handle 150 can be used in checking and adjusting the version alignment, and/or can be used to manipulate the resection guide 100, and thus can sometimes be referred to as a manipulation tool. The handle 150 in the illustrated embodiment includes a distal end or portion 150*d* configured to engage with the opening 142 formed in the vertical alignment plate 140 and a proximal portion 150*p* or body. The proximal portion 150*p* and distal portion 150*d* can be joined at an angle γ matching the natural angle of retroversion, which can be approximately in the range of about 0° to about 30°. In the illustrated embodiment, the angle 7 is 30°, and as such the handle can be considered a 30° version handle.

The distal end 150*d* includes block 152 sized and shaped to pass into the opening 142 and a latch 154 configured to enter the side opening 143 and contact a portion of the block 152 within the opening 142 to secure the handle 150 to the vertical alignment plate 140. The latch 154 can include a distal securing portion 154*d* and a proximal handle portion 154*p*. In the illustrated embodiment, the latch 154 is coupled to the handle 150 with a pin and slot such that the latch 154 can pivot with respect to the handle 150. In at least some embodiments, a spring and/or other biasing mechanism(s) can be disposed within a latch coupling to bias the latch 154 in a closed or secured position illustrated in FIG. 5B. In the secured position, the proximal handle portion 154*p* of the latch 154 can be disposed within an opening 156 formed in the body 150*p* of the handle and the distal securing portion 154*d* can contact the block 152. In some embodiments, the proximal handle portion 154*p* can protrude slightly from the body opening 156. To secure the handle 150 to the resection guide 100, the proximal handle portion 154*p* of the latch can be pressed in a direction that is into or through the opening 156 to pivot the latch to an open position. When the latch 154 is pivoted to the open position, the distal securing portion 154*d* can move in a direction away from the block 152 such that the block can be inserted into the opening 142. When the block 152 is seated within the opening 142, the proximal handle portion 154*p* can be released and a biasing mechanism can pivot the latch 154 back to the secured position. As shown, a depression can be formed in the proximal handle portion 154*p*, which can be configured, for example, to be complimentary to a fingertip of a user. A tactile click or other audible side can be made when the latch

154 is pivoted into the secured, locked position so the user knows that the handle 150 is secured and stationary with respect to the superior radial arm 110. The distal securing portion 154*d* of the latch can be shaped and sized to enter the side opening 143 until it contacts the block 152 within the opening 142 thereby securing the version handle 150 to the vertical alignment plate 140. A person with skill in the art will appreciate that various other biased pivoting coupling components can be used to couple the latch 154 to the handle 150 in lieu of the pin and slot coupling illustrated in FIG. 5B. Further, a person skilled in the art will appreciate that the latch 154 is one form of a locking mechanism that can be used in conjunction with the version handle 150 to secure a location of the version handle 150 with respect to the vertical plate 140, and that other mechanisms and techniques known to those skilled in the art can be used to lock a location of the version handle 150 with respect to the vertical plate 140.

The handle 150 can be operated to adjust the position of the superior radial arm 110 relative to the humeral head (e.g., location along the X or Y axis, angle of inclination, retroversion, and/or anteversion). More generally, a person skilled in the art, in view of the present disclosures, will appreciate that the handle 150 can be easily and quickly inserted into and removed from the vertical alignment plate 140, providing for a quick and easy way to manipulate the humeral resection guide 100 while adjusting it to set the desired resecting plane, among other features of the guide 100. In fact, the version handle is designed to be a quick-release tool for efficient manipulation of the guide 100 with only one hand during use.

Figure 5B:
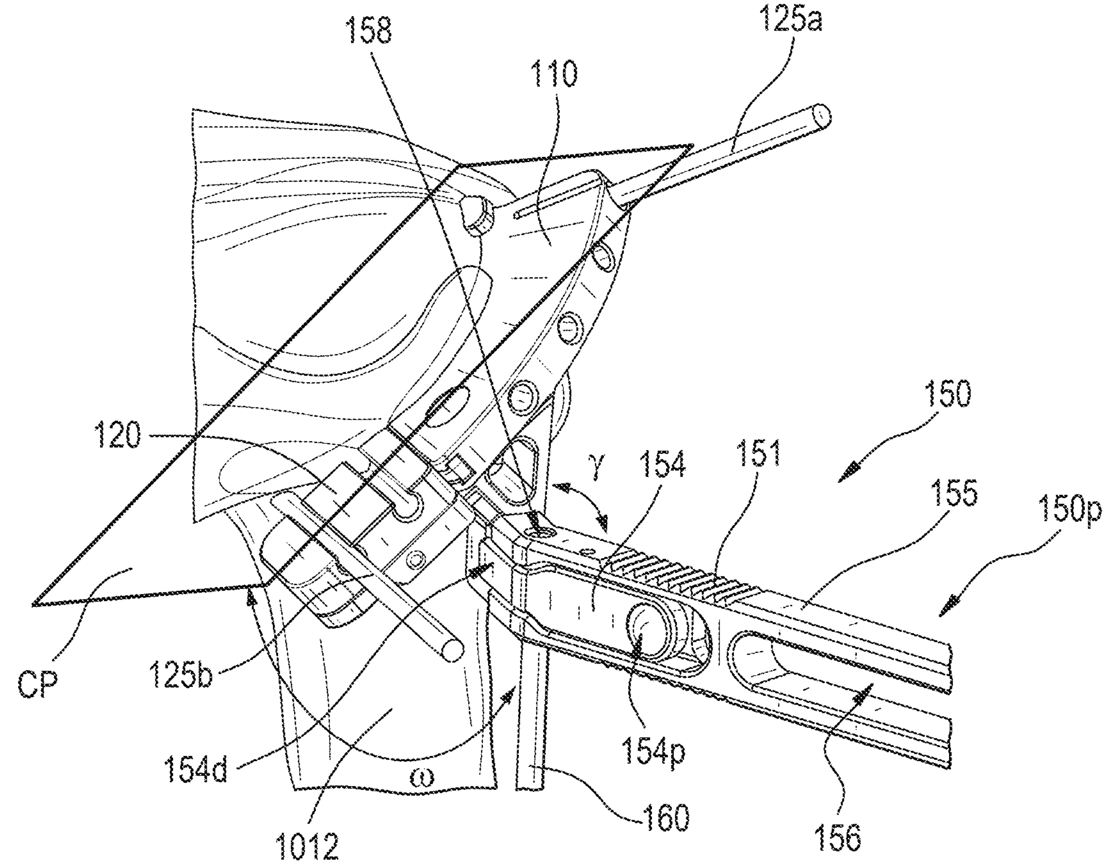
FIG. 5B is a top perspective view of the elongate shaft of the humerus and the humeral resection guide and handle of FIG. 4 with a vertical guide rod coupled to the handle, extending substantially parallel to the elongate shaft of the humerus, and with the subscapularis and the supraspinatus illustrated translucently.
Figure 6:
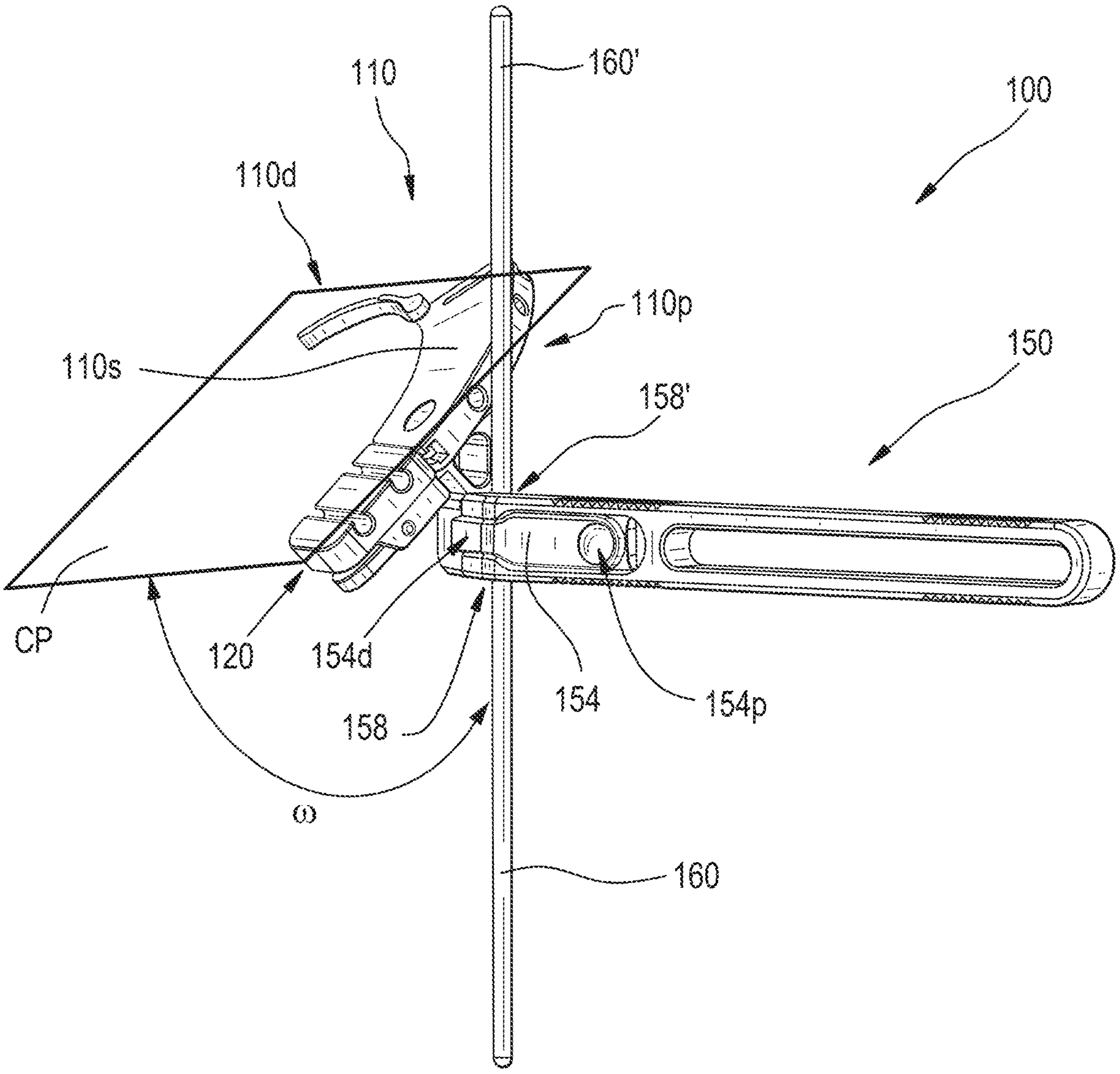
FIG. 6 is a front perspective view of the humeral resection guide, the handle, and the vertical guide rod of FIG. 5B, with a second vertical guide rod illustrated in phantom.

The version handle can further include a threaded slot or opening 158 configured to receive a vertical guide rod 160, also referred to as a silhouette resection guide pin or a vertical extension rod, among other names, as shown in FIGS. 5B and 6. In at least some embodiments, the vertical guide rod 160 can be optionally coupled to or otherwise associated with the humeral resection guide 100. This can occur prior to securing the guide 100 to the humerus 1012, although it is possible such coupling or otherwise association can occur after securing the guide 100 to the humerus 1012. In the illustrated embodiment, the vertical guide rod 160 is coupled to the handle 150. More specifically, a threaded terminal end of the guide rod 160 is disposed within the threaded slot 158 of the handle 150 such that the guide rod 160 extends distally, along the humerus 1012 as shown in FIG. 5B. The vertical guide rod 160 can assist in providing visualization of the orientation of various features of the resection guide 100 when the guide 100 is disposed at the surgical site, as well as providing a way to manipulate aspects of the guide 100 from a location remote of the surgical site, including outside of a patient's body. For example, the guide rod 160 coupled to the handle 150 can be aligned along the same axis as the vertical alignment plate 140 such that the guide rod 160 extends the length of the plate 140 to help make it easier to align the same with, for example, the elongate shaft 1014 of the humerus 1012. The guide rod 160 can also be used to help manipulate vertical alignment plate 140 and superior radial arm 110 from a location a distance away from the surgical site, including outside of the body. In alternative embodiments, the guide rod 160 can extend in the opposite direction, as illustrated by a phantom guide rod 160' extending proximally in FIG. 6, and still provide alignment guidance. In such alternative embodiments, the guide rod 160' can be threaded into a threaded slot 158' formed opposed to the slot 158, or alternatively, the slot 158 can extend through the body of the handle 150. The ability for a guide rod to be disposed in either direction allows the version handle 150, and the associated guide rod 160, 160', to be used in an inferior position and/or a superior position. Further, while the slots 158 are described as being threaded, in other embodiments, they are not and/or other mating features can be used to couple a guide rod to the version handle 150 and/or the vertical alignment plate 140.

FIG. 5B also illustrates a pin 125*a* passed through one of the receiving openings 114 formed in the guide 100 to help secure the guide 100 to the humerus 1012. Thus, as shown, the pins 125*a* and 125*b* are used to help secure the guide 100 to the humerus 1012.

Different sized arms for use with different patient and patient anatomies, and other components of a guide(s) and/or used in conjunction with the guides of the present disclosure, can be provided together as a kit. This humeral resection guide kit can include, for example, any combination of superior arms 110, guide extenders 120, vertical alignment plates 140, handles 150, and/or vertical guide rods 160, 160' of various sizes, among other components and features provided for herein. A person skilled in the art will appreciate that such kits are not limited to only the embodiments disclosed and explicitly illustrated herein, but rather, includes various configuration and iterations accounted for in the text and/or otherwise understood to achieve similar purposes as provided for herein. The various components can be sized and/or shaped for different patient anatomies (e.g., adult, child, patient having certain bone formations due to various ailments or diseases, etc.). Further, a humeral resection guide kit, and/or components thereof, can be more generally be part of a shoulder arthroplasty surgery kit, or surgical kit more generally.

Use of the First Embodiment of the Humeral Resection Guide and Related Components to Resect a Humeral Head Traditional resection guides used to create a cutting or resecting plane as part of a shoulder arthroplasty procedure rely on the adequate visibility of the articular margin and access to the joint space provided by removing the subscapularis tendon and externally rotating the convex humeral head out of the glenoid surface to perform this cut. Thus, for tissue-sparing procedures, and other types of procedures performed in more limited space and/or with more limited displacement of tissue and the like, humeral resection guides of the nature provided for herein are necessary.

As described herein, and as shown in FIG. 6, the humeral resection guide 100 can be a single piece guide including a superior radial arm 110 and a vertical alignment plate 140. Features like the guide extender 120 and handle 150 can be considered separate components that can be used in conjunction with the arm 110, or alternatively, one or more of these components can be considered portions of the guide 100, thus making the guide 100 having more than one piece. In some other embodiments, the vertical alignment plate 140 can also be a separate component from the superior radial arm 110 and/or other combinations of these various components can be included or not included as part of the humeral resection guide 100 integrally formed, removable and replaceably attached, etc.

Because the superior arm can be separately disposed, the arm 110 can be introduced into the patient's glenohumeral joint 1010 separately and additional components can be coupled to the arm, or alternatively, the additional components can be coupled to the superior radial arm 110 prior to insertion into the glenohumeral joint 1010. In the illustrated embodiment of FIG. 4, the handle 150 is coupled to the superior radial arm 110 as described above and a vertical guide rod 160 is threaded into the thread slot 144 of the handle 150 prior to insertion. The handle 150 and vertical guide rod 160 can assist in positioning the guide 100 in the joint space by extending out of the body or surgical site and providing space for the surgeon to grip and manipulate the guide 100 from a distance outside of the surgical site.

As shown in FIG. 4, the superior radial arm 110, including the distal member or portion 110*d* thereof, respectively, can be inserted into the joint space through the rotator interval 1020 and towards a posterior portion of the humeral articular margin while aligning against a supraspinatus insertion or attachment point 1111. This placement can set a height of the resection guide 100 at the surgical site. In the joint space, the superior radial arm 110 can be positioned between a supraspinatus 1019 and a humeral head attachment point 1111 to define the articular margin 1009 (see FIG. 2). The arm 110 can sit against an upper surface of the humeral head 1013, for instance at the articular margin 1009 or other desired resection location. During insertion, a surgeon can palpate along the superior radial arm 110 to ensure the arm 110 is tight against the supraspinatus insertion at a greater tuberosity 1027 of the humeral head 1013, as well as positioned to follow the articular margin 1009 posteriorly. This creates a tight attachment of the guide 100 against the supraspinatus attachment point. The blade slot 115 of the superior radial arm 110 can be aligned to an anatomical landmark, such as the bicipital groove of the humerus 1012 or the rotator interval, to accurately define an entry point for a cutting tool. The rotator interval alignment can be used, for example, for an anatomical procedure or area. This positioning can also help ensure any soft tissue is retracted away from a cutting blade that passes through the blade slot 115. The superior radial arm 110 can be considered proximate to the humeral head when it is passed through the rotator interval 1020 and within approximately three centimeters of the humeral head 1013. For most anatomies, when properly positioned, approximately 1 millimeter of bone can remain at the insertion after the resection. Any posterior cuff and/or deltoid retractor(s) can be removed and the arm can be slightly abducted to help ensure optimal placement of the superior radial arm 110.

Figure 7:
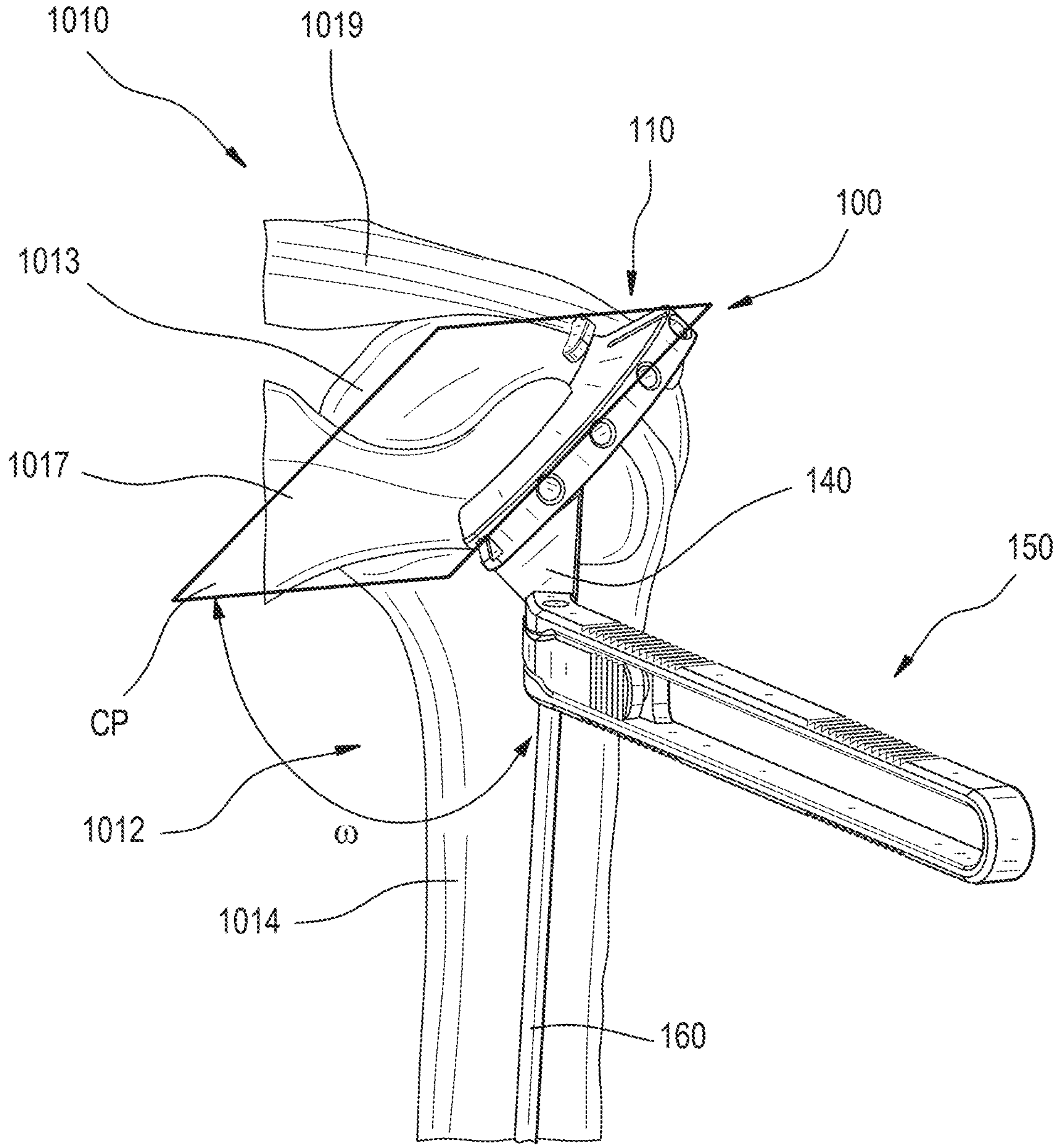
FIG. 7 is a side perspective view of the humeral resection guide disposed at the human glenohumeral shoulder joint of FIG. 4, the humeral resection guide being coupled to the humerus and having the handle coupled thereto, and the handle having the vertical guide rod of FIG. 6 coupled thereto.

In place at the surgical site, the resection guide 100 can define the cutting plane CP. More particularly, in at least some embodiments, the resection guide can approximate a 135° angle (or, more generally, approximately in a range of about 125° to about 145° as indicated earlier), as shown the cutting plane angle ω, that serves as the humeral resection angle. The approximate 135° angle can be defined, for example, when the vertical guide rod 160 is aligned with the shaft 1014 of the humerus 1012, as shown in FIG. 7. Before, during, and/or after introduction of the arm 110 to the glenohumeral joint 1010, a displacement wrap(s), retractor (s), and/or other component(s) useful in manipulating a location of a subscapularis tendon can be used to move the subscapularis tendon out of the way to improve visualization.

As illustrated in FIG. 7, the version handle 150 can be coupled to the vertical alignment plate 140 associated with the superior radial arm 110. The latch 154 can be operated to secure the version handle 150 to the alignment plate 140. The vertical guide rod 160 can be threaded into the thread slot 144 of the handle 150 and extend distally along the humerus 1012 to help better align the vertical alignment plate 140, and thus the guide 100, with the elongate shaft 1014 of the humerus 1012. As shown, the vertical guide rod 160 can be aligned, i.e., parallel or substantially parallel to, the elongate shaft 1014 of the humerus 1012. The rod 160 can typically be maintained in this parallel or substantially parallel configuration with respect to the shaft 1014 at least until one or more bone pins, such as the bone pins 125*a*, 125*b*, 125*c*, are used to couple the guide 100 to the humeral head 1013 and/or the humerus 1012. The rod 160 can be secured in this parallel or substantially parallel manner before and/or after it is secured to the version handle 150. More particularly, in conjunction with positioning the guide 100 at the anatomic neck, the vertical guide rod 160 can be used to align the flexion/extension angle of the humeral head, i.e., aligning the angles α' and β' to form a linear pair long the longitudinal axis L (see, e.g., FIGS. 2 and 3A). When the vertical guide rod 160 is aligned with the elongate shaft 1014 of the humerus 1012, the humeral resection angle, i.e., the cutting plane angle ω, can be approximately 135° (or, more generally, approximately in a range of about 125° to about 145° as indicated earlier). Further, when attached, the handle 150 can be set at about approximately 30° of retroversion and can be aligned with the forearm. Alternatively, the handle 150 can be manually set to an alternate version. Movement of guide 100 to achieve the desired alignment can be accomplished, for example, by manipulating the vertical guide rod 160 and/or handle 150 to adjust the angle of inclination or retroversion of the superior radial arm 110 with respect to the humerus 1012.

Figure 8A:
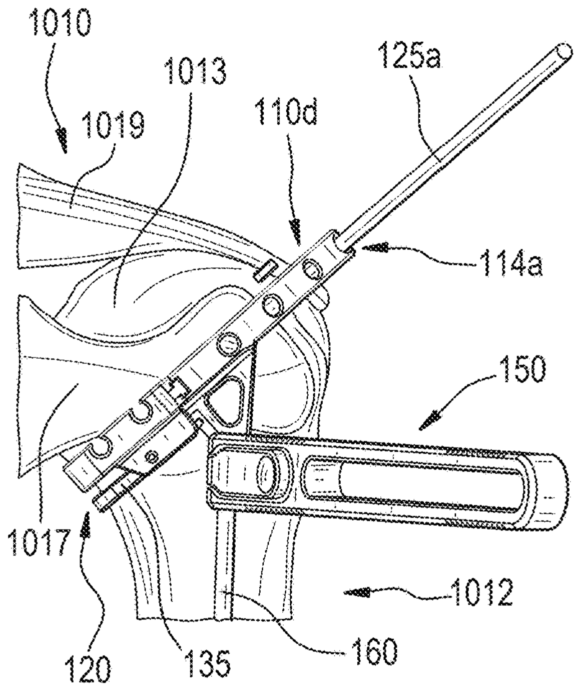
FIG. 8A is a side perspective view of the humeral resection guide of FIG. 7 having the guide extender of FIG. 3C coupled thereto, the handle and vertical guide rod of FIG. 7, and a superior bone pin passing through the humeral resection guide to couple the humeral resection guide to the humerus.

After a position of the guide 100 with respect to the humeral head 1013 has been set, one or more pins can be introduced to maintain the guide 100 at the desired location with respect to the humeral head 1013 to couple the guide 100 to the humeral head 1013, and thus the humerus 1012. As shown in FIGS. 8A and 8C, a pin 125*a* can be placed bi-cortically into the humeral head 1013, in the bicipital groove area, without pinning through soft tissue. More particularly, one pin 125*a*, which can be considered a superior pin based on its illustrated placement, can be positioned in an opening or hole 114*a* formed in the superior radial arm 110 and into the humeral head 1013 at a location between the supraspinatus 1019 and subscapularis 1017 tendons such that the pin 125*a* does not violate the supraspinatus 1019. The pin 125*a* can be inserted into any one of the openings 114 of the superior radial arm 110 to avoid passing the pin 125*a* through the supraspinatus 1019 and subscapularis 1017 tendons or other soft tissue surrounding the joint area.

The guide extender 120 can be optionally coupled to the proximal end of the superior radial arm 110 to extend the resecting plane beyond the inferior border 1021 of the subscapularis tendon as shown in FIG. 8A. The use of the guide extender 120 can provide a more "patient specific anatomic" humeral resection, which may not be an approximately 135° resection angle. The resection angle that can result from using the extender 120 is approximately in the range of about 135° to about 155°. When using the guide extender 120, the vertical guide rod 160 can still be used to reference bone alignment, but it may be ignored for purposes of defining the inclination angle.

Figure 8B:
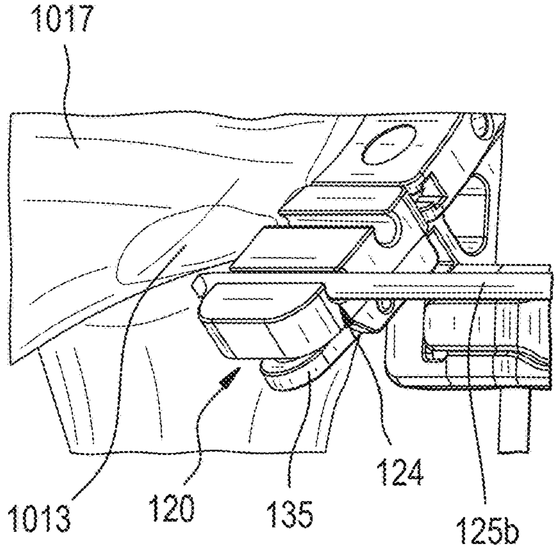
FIG. 8B is a detailed perspective view of the guide extender of FIG. 8A having an inferior bone pin passing therethrough to couple the guide extender, and thus the humeral resection guide, to the humerus, with the subscapularis illustrated translucently.
Figure 8C:
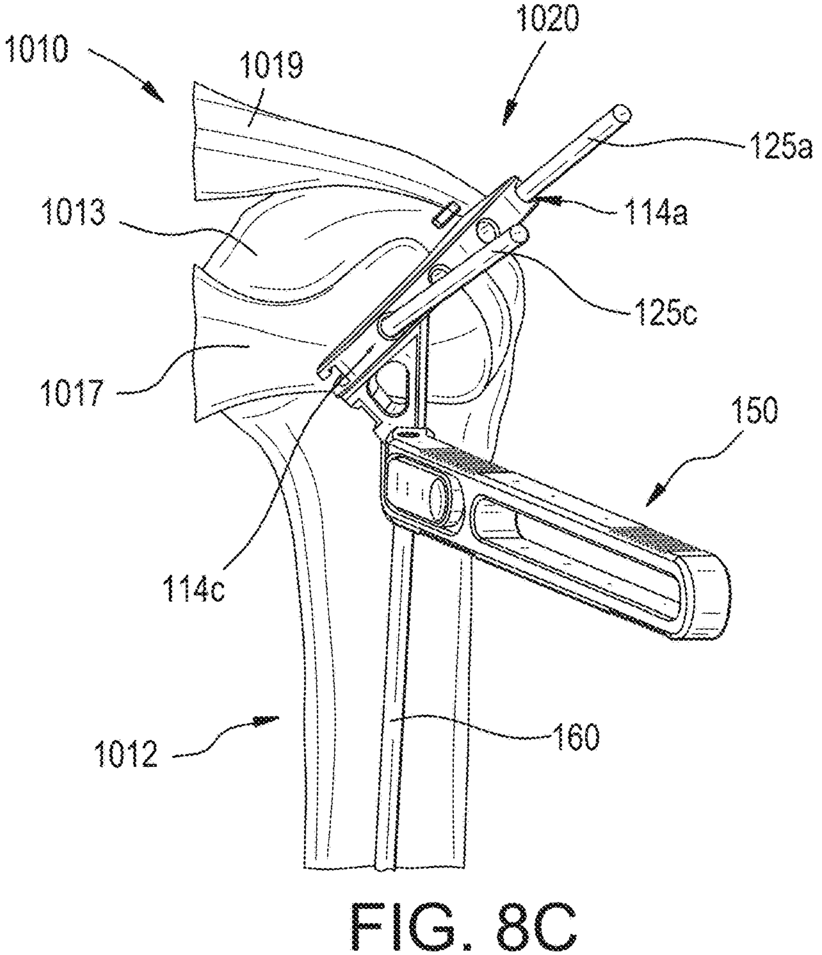
FIG. 8C is a side perspective view of the humeral resection guide, handle, vertical guide rod, and superior bone pin of FIG. 8A, and a second bone pin, inferior to the superior bone pin, passing through the humeral resection guide to further couple the humeral resection guide to the humerus, and the guide extender of FIG. 8B now detached from the humeral resection guide.

To introduce the extender 120 to the surgical site, a retractor(s), such as an inferior subscapularis retractor(s), a small Hohmann retractor(s), and/or a Senn retractor(s), can be used to gently lift the subscapularis to visualize and palpate the inferior articular margin using a pin 125*b*, as shown in FIG. 8B. The resection guide 100 can be adjusted as necessary until a desired "patient specific anatomic" inclination is achieved, i.e., the angle ranges provided in the preceding paragraph.

A top surface of the extender 120 represents the intended humeral resection plane, i.e., the equivalent of the cutting plane CP. Each of the grooves 124 formed in the extender 120 can be positioned tangent to the resection plane. When positioning the guide 100, a top surface of the pin can be referenced, which in turn becomes the bottom of the extended cutting tool that performs the resection (e.g., the tool 102 as shown in FIG. 9B)

If the guide extender 120 is used, another guide pin, for example the pin 125*b*, which can be considered an inferior pin based on its illustrated placement, can be positioned in the grooves 124 formed in the inferior extender 120. The pin 125*b* can inserted into the humerus at a location below the subscapularis 1017. Use of the guide extender 120 helps prevent passing a pin through the subscapularis 1017, while also achieving a "patient specific anatomic" resection. The illustrated positioning of the pins 125*a*, 125*b* helps ensure that the pins do not pass through or otherwise violate supraspinatus 1019 tissue and/or subscapularis 1017 tissue. In embodiments where the guide extender 120 is not used to achieve a "patient specific anatomic" resection, such as the embodiment illustrated in FIG. 8C, an inferior pin 125*c* can be passed through an opening or hole 114*c* of the superior radial arm 110 at a location inferior to the superior pin 125*a* to further secure the guide 100. In such instances, the extender 120 can be used to provide a visual confirmation inferiorly. In some cases, the inferior pin can pass through the subscapularis tendon 1017 and into the humeral head 1013. A person skilled in the art will appreciate any combination of the openings or grooves 114, 124 can be used to have pins disposed therein for positioning the guide 100 with respect to the humeral head 1013 and/or the humerus 1012. The position of the guide 100 can typically be maintained while placing the pins (e.g., the pins 125*a*, 125*b*, 125*c*). While a variety of pin configurations can be used, in at least some embodiments, one pin, as shown the pin 125*a*, can often be disposed at a most superior position within the rotator interval to ensure that none of the pins violate the supraspinatus tissue 1019, and a second pin, as shown the pin 125*c*, can be in an inferior location positioned below or through the subscapularis 1017. As shown in FIG. 8C, the pin 125*a* is in the most superior position and the pin 125*c* is at the inferior location, disposed through the subscapularis 1017. The 1350 angle can sometimes be preferred when there is a high potential for poor bone quality as it can allow for easy conversion to a shoulder system anatomic surgical technique.

Figure 9A:
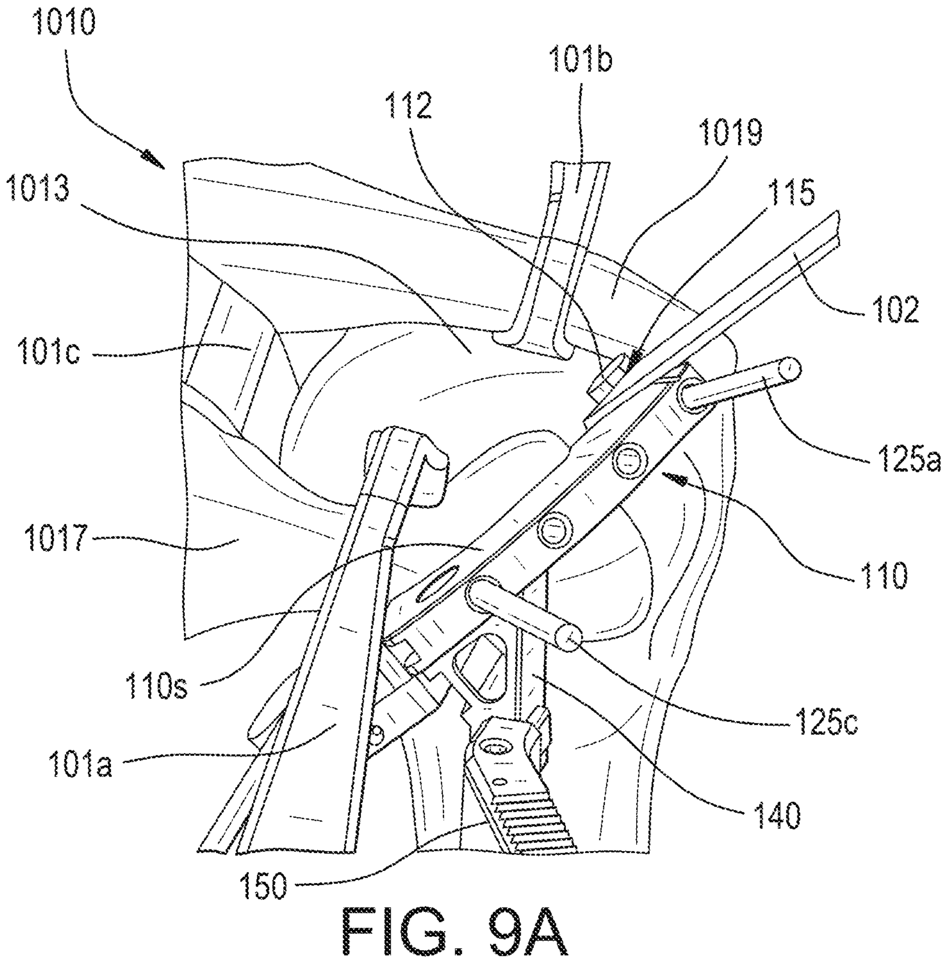
FIG. 9A is a side perspective view of the humeral resection guide and associated components and anatomy of FIG. 8C having the guide extender of FIG. 3C coupled thereto with retractors and a cutting tool introduced into the human glenohumeral joint space.
Figure 9B:
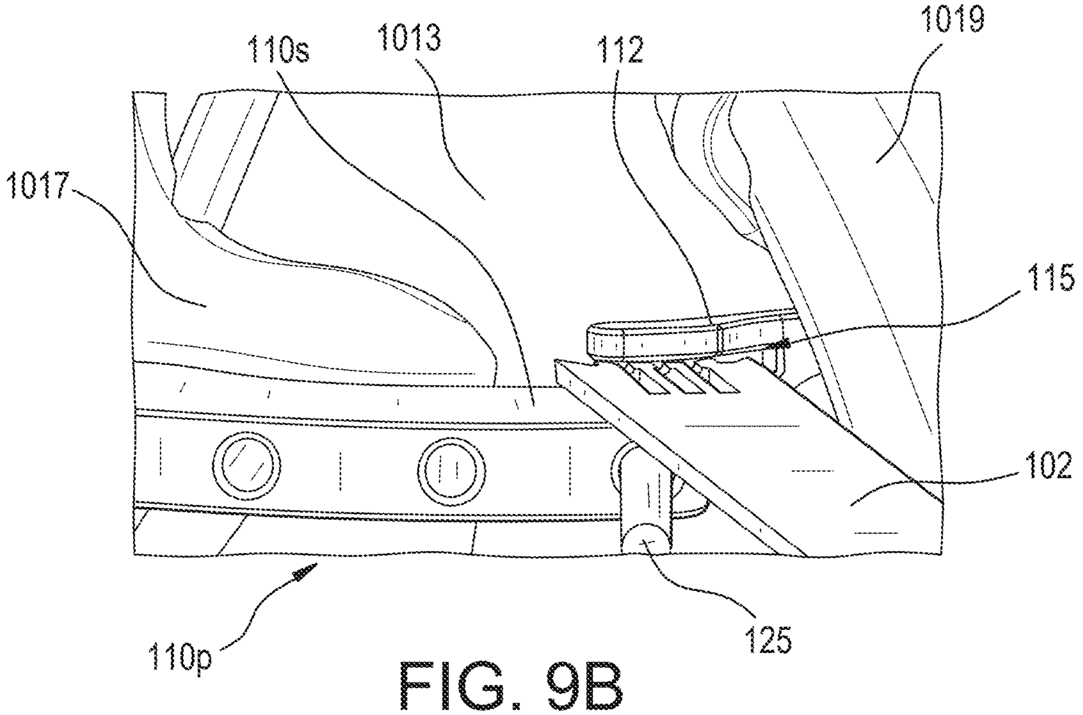
FIG. 9B is a detailed view of the cutting tool of FIG. 9A entering the humerus and guided by the humeral resection guide.

FIGS. 9A and 9B illustrate the cutting or resection action performed to complete the procedure. A cutting tool 102 for use in performing the resection can be a saw, such as a narrow rigid saw (e.g., a sagittal saw). In some embodiments, the saw can have a width of approximately 13 millimeters. One or more retractors, such as anterior subscapularis retractor(s) and/or posterior cuff retractor(s) (e.g., angled or double bent Hohmann retractors) 101*a*, 101*b*, or other soft tissue retractors known in the art, can be used to move surrounding soft tissue to help protect the subscapularis tendon 1017 and the supraspinatus tendon 1019 during the humeral cut and/or to provide additional visualization. One or more retractor(s) 101*c*, such as a Darrach retractor(s) or a curved Hohmann retractor(s), can be positioned over the humeral head 1013 and against the glenoid 1018 for protection during resection.

As noted above, a blade slot 115 formed over the superior arm surface 110*s* can be used to align the cutting tool 102 planar with the superior arm surface 110*s* while also ensuring an entry position for the tool 102 is between soft tissue humeral attachment points, specifically at the bicipital groove as denoted by the line 1011. A first blade plunge of the tool 102 can follow the blade slot 115 and into the humeral head 1013. The tool 102 can then be retracted, pivoted, and a second plunge can occur, again keeping the blade flat on the superior planar surface 110*s* and within the blade slot 115. This cutting technique can continue to be repeated until the humeral head has been resected and/or cut as desired, all the while being able to avoid damaging the subscapularis tendon 1017 and the supraspinatus tendon 1019 because of the configuration of the device and surgical procedures performed in view of the same. For example as discussed above with respect to FIG. 4, the distal portion 110*d* of the superior arm can act as a shield to protect the far side anatomical structures from the saw blade, particularly if care is taken to ensure the cutting tool 102 follows the cutting plane defined by the blade slot 115 and superior surface 110*s*. When performing the plunging cut actions and reaching completion medial and posteromedial, care should be taken to avoid injury to the axillary nerve. In some patients, minimal release of the upper border of the subscapularis 1017 can provide additional clearance for the cutting tool 102.

After a series of plunge cuts are performed to resect the humeral head 1013 as desired, thus completing the humeral osteotomy, the pins, as shown the pins 125*a*, 125*c*, can be removed, as can the guide 100. Removal of at least some of the components, such as the guide 100, can occur through the rotator interval 1020. In at least some instances, the final portion of the humeral cut can be performed with an osteotome or other suitable instrument(s). If appropriate and/or desired, the guide 100 can be repositioned for one or more additional cuts to be performed. After the pins 125*a*, 125*c* and guide 100 have been removed, the resection plane can be palpated, and a rongeur, osteotome, and/or other instrument(s) can be used to remove any residual bone above the resection plane and/or residual osteophytes.

After the humeral head 1013 has been resected, the bone quality can be evaluated, for example by applying thumb pressure to the resulting humeral resection surface. If a thumb can be depressed into the humerus without much resistance, the bone may not be sufficient to support a stemless implant with the approach provided for herein and a stemmed implant may provide better fixation. A person skilled in the art, in view of the present disclosures, will understand how to use a stemmed implant in conjunction with disclosed procedures.

Second Embodiment of a Humeral Resection Guide and Related Components

Figure 10:
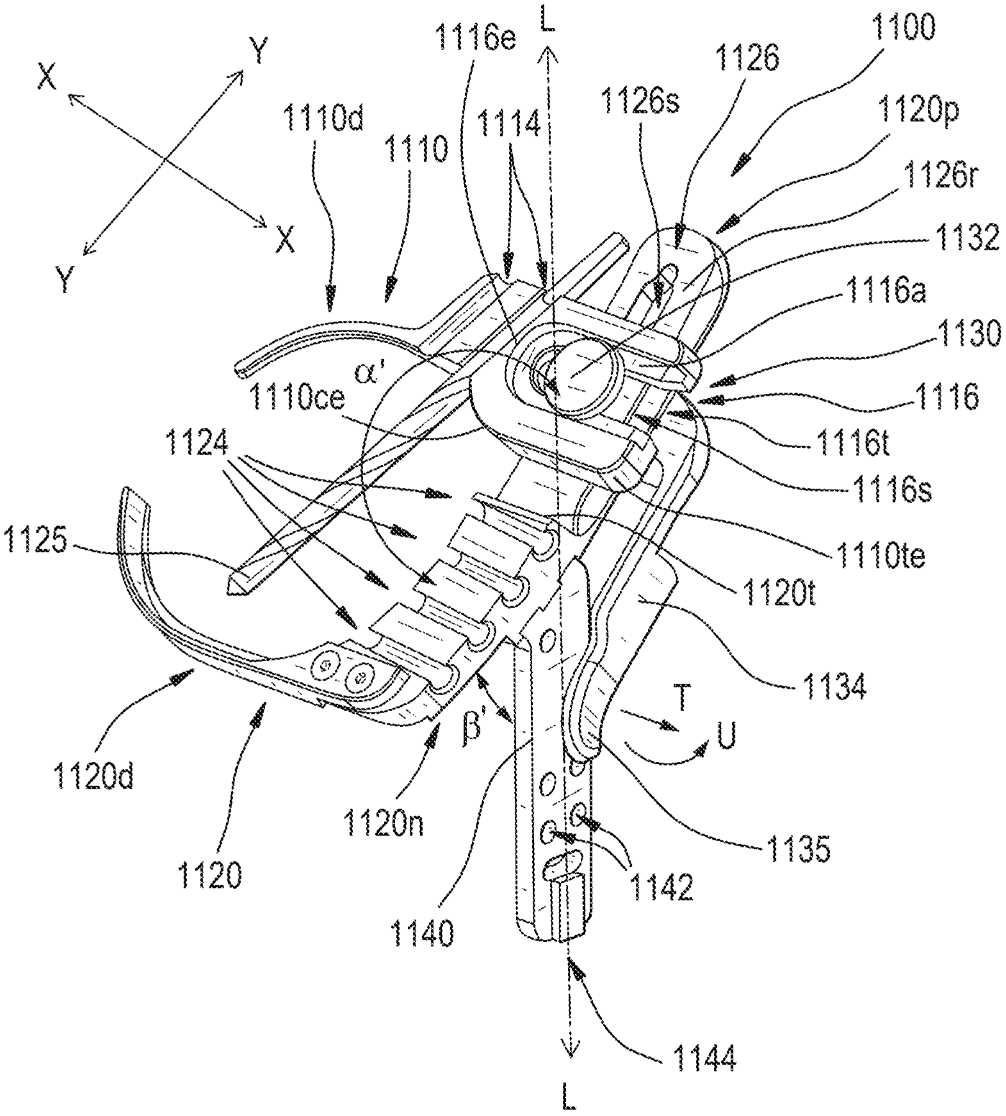
FIG. 10 is a front perspective view of yet another embodiment of a humeral resection guide that includes both a first arm and a second arm, the humeral resection guide having a drill bit associated therewith.

FIG. 10 illustrates another embodiment of a humeral resection guide 1100. The guide 1100 serves a general similar purpose as the guide 100 in that it secured to the humerus to set a cutting or resecting plane and help guide a cutting tool along the cutting plane to form a planar surface on the humerus onto which an implant and/or prosthesis can be coupled. The design is such that it can be disposed in the narrow glenohumeral joint space while the subscapularis tendon is still attached to the humerus.

The resection guide 1100 can include a first, superior arm 1110 and a second, inferior arm 1120, the arms 1110, 1120 being the portion of the guide 1100 designed to enter a joint space and engage a humeral head and/or a humerus to set a desired cutting plane or angle. The superior arm 1110 can be configured (e.g., sized, shaped, and have particular features illustrated and/or described herein) to enter the narrow joint space superior to the subscapularis tendon and the inferior arm 1120 can be configured (e.g., sized, shaped, and have particular features illustrated and/or described herein) to enter the narrow joint space inferior to the subscapularis tendon. The arms 1110, 1120 in the illustrated embodiment are two distinct and separate arms, able to be adjusted or otherwise moved with respect to each other. More particularly, an adjustable control or connection mechanism 1130, also referred to as a connection pivot, can be used to selectively mate the arms 1110, 1120 together, and can also permit the arms 1110, 1120 to have at least three degrees of freedom: (a) sliding in an X direction commensurate with an illustrated X axis; (b) sliding in a Y direction commensurate with an illustrated Y axis; and (c) rotating about a screw 1132 of the adjustable connection mechanism 1130 of an X-Y plane defined by the X and Y axes. As provided for herein, the screw 1132 is merely one example of a connection pivot, and that other components can be used in lieu of a screw, such as a post, boss, or other structures known to those skilled in the art that allow for attachment of the arms and pivoting around the same. These three degrees of freedom allows the arms 1110, 1120 to be adjusted to accommodate various sizes and shapes of humeral heads, thus being able to account for different humeral head diameters and shapes that comes with patient variability.

Movement of the arms 1110, 1120 with respect to each other can occur when the adjustable control or connection mechanism is in an unlocked configuration, with such movement being able to include de-coupling the first arm 1110 from the second arm 1120 by sliding the first arm 1110 away from the second arm 1120 in the X direction, which is commensurate with the illustrated X axis. Movement of the arms 1110, 1120 with respect to each other can be prevented by placing the adjustable connection mechanism 1130 in a locked configuration. As shown, a latch 1134 can be used to move the adjustable connection mechanism 1130 between the unlocked and locked configurations. The latch 1134 may be considered as part of the adjustable connection mechanism 1130, or alternatively, it can be considered its own separate component that helps operate the adjustable connection mechanism 1130. The latch 1134 can be operable by a single digit (i.e., finger, thumb), sometimes referred to as one-digit or one-finger actuation, moving the resection guide 1100 between an unlocked configuration and a locked configuration by pushing or pulling on the latch 1134 with the single digit.

The resection guide 1100 can also include a vertical alignment plate 1140, which as shown can be coupled to the second arm 1120 by a weldment or a press fit, for example, between the two components. The vertical alignment plate 1140 forms an angle α' with the second arm 1120, and more particularly a top surface of the second arm 1120. By aligning the vertical alignment plate 140 with the longitudinal axis L of the elongate shaft 1014 of the humerus 1012, and having the angle α' match the natural angle α of inclination, a cutting plane defined by the X-Y plane of the superior and inferior arms 110, 120 can be aligned with the cutting plane illustrated by the articular margin 1009. Accordingly, the cutting plane can likewise have an angle α' approximately in the range of about 125° to about 145°, for example 135°, the cutting plane angle being defined by the angle α' formed by the vertical alignment plate 1140 and the second arm 1120 as shown.

A counterpart angle β', as shown, can likewise have similar values as the counterpart angle R described above. In the illustrated embodiment, the angle R is not adjustable, although in other embodiments, including modification of the illustrated embodiment and other embodiments disclosed herein, it can be. As shown, the vertical alignment plate 1140 and the second arm 1120 are welded or otherwise fixed as a unit. By aligning the vertical alignment plate 1140 with the long humeral bone, that sets the desired the location of the second arm 1120. That is, rotating or otherwise moving the vertical alignment plate 1140 can effectively change the angle of the cut to the humerus because it changes the positioning of the second arm with respect to the humeral head. This serves as another degree of freedom of the resection guide 1100.

As shown, a plurality of openings or holes 1142 can be formed through an outer, planar surface of the vertical alignment plate 1140. These openings 1142 can be used, for example, to receive a tool for use in checking and/or adjusting the version alignment of the resection guide 1100, such as the version handle 1150, a tool 1150 illustrated in FIG. 12, and/or a tool 2150 illustrated in FIG. 16, similar to the opening 142 for receiving the version handle 150. Version alignment takes into account retroversion and/or anteversion, as understood by those skilled in the art in view of the present disclosures. More particularly, the version alignment capabilities of the present disclosure allows a surgeon to rotate the guide 1100 and check angular alignment with a foreman of the patient using the openings 1142 in the vertical alignment plate 1140. The surgeon can either match exact patient anatomy as desired, or use this version angular alignment check to set the version to a desired value based on other patient factors, such as existing range of motion with the contralateral arm. A person skilled in the art will appreciate other features besides openings 1142, such as protrusions or other distinguishing features, can be used to achieve similar results.

Figure 13:
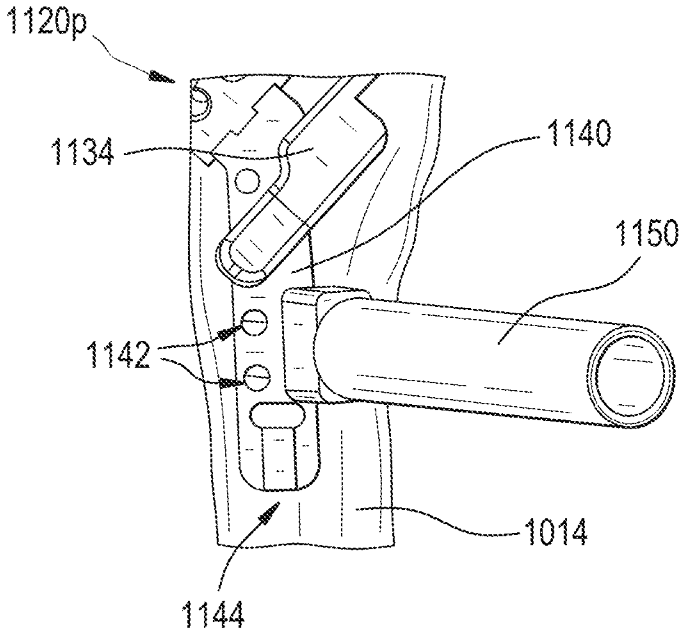
FIG. 13 is a side perspective view of the second arm, locking mechanism, and vertical alignment plate of FIG. 11B, the vertical alignment plate being disposed proximate to the elongate shaft of the humerus of FIG. 2 and associated with a version handle.

These tools used in checking and adjusting the version alignment can also be used to manipulate the resection guide and can sometimes be referred to as manipulation tools. The plurality of openings 1142 can be formed through the vertical alignment plate at an angle 300 from the surface of the vertical alignment plate to place an inserted manipulator tool 1150 at an angle matching the natural angle of retroversion, which is approximately in the range of about 0° to about 30°, as shown in FIG. 13. The tool 1150 can include a distal end having one or more posts (not visible) configured to sit within the openings 1142 to allow for subsequent manipulation of the vertical alignment plate 1140. Additional details about such a tool 1150 are at least described above with respect to the tool 150 and/or below with respect to the tool 2150 in FIG. 16, and thus a further description of the tool 1150 is unnecessary. The features described with respect to one of the tools 150, 1150, and 2150 can be applicable to the other of the tools 150, 1150, and 2150, even to the extent certain features are not labeled or otherwise identified in writing herein for the tool 1150. Still further, a threaded slot 1158 can be provided at a distal end of the vertical alignment plate 1140, the slot 1158 being configured to receive a vertical alignment rod, like the rod 160 described above or a rod **2160*a* provided for in FIG. 16**.

Figure 16:
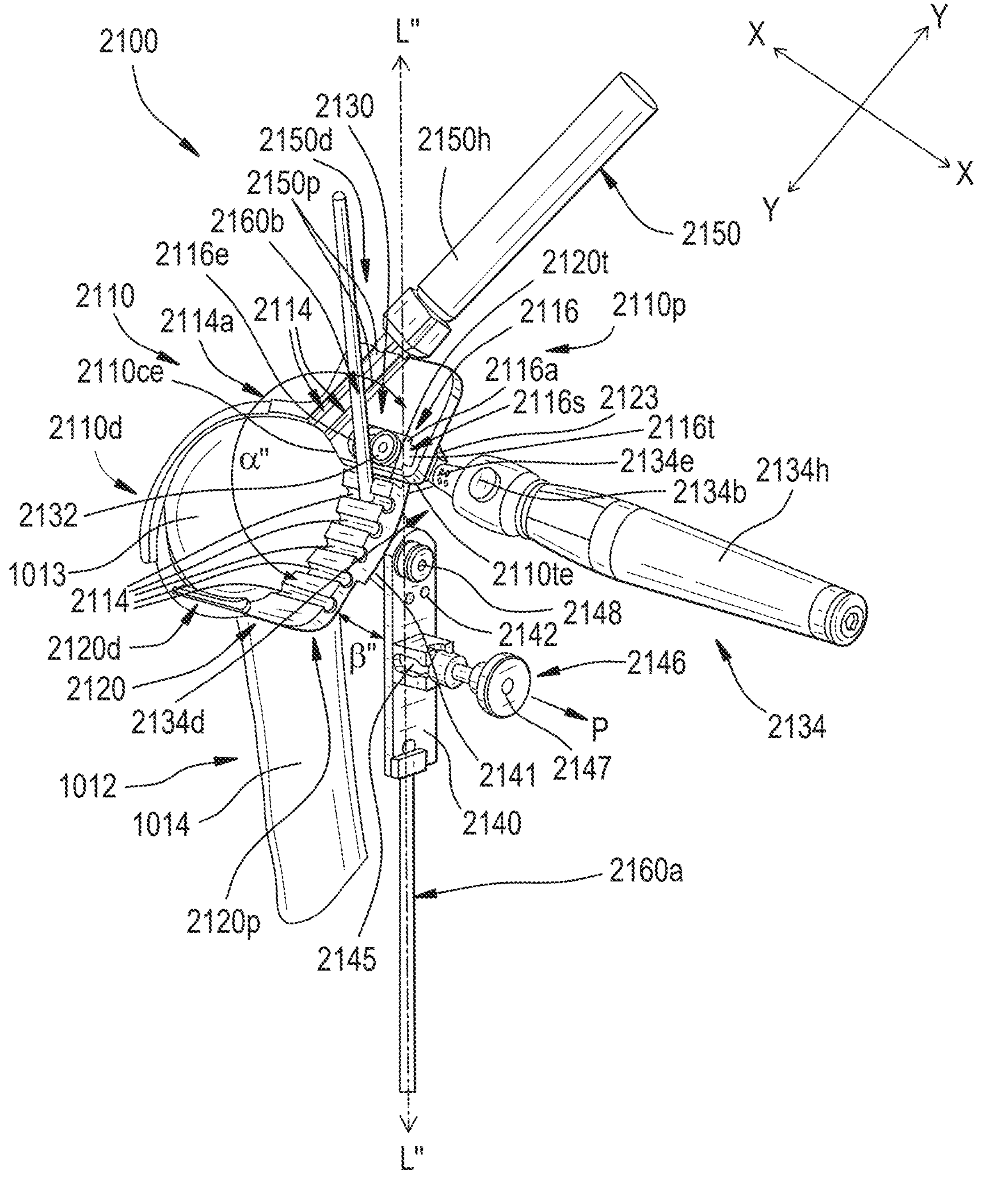
FIG. 16 is a front perspective view of another embodiment of a humeral resection guide, the humeral resection guide being secured to the humerus of FIG. 2 and having various complementary components associated therewith.

A non-limiting example of an adjustable vertical alignment plate 2140 is illustrated and described with respect to FIG. 16, and like other features provided across various embodiments provided for herein, can be adapted for use with guide 1100, as well as other embodiments of humeral resection guides provided for herein or otherwise derivable from the present disclosures. In some instances, the vertical alignment plate 1140 can be considered its own component that can be selectively attached and detached to the guide 1100, while allowing angular rotation to optimize the cut angle α' in at least some instances, while in other instances it can be considered as part of the guide 1100 and/or as part of the second arm 1120. Any known technique for coupling two components can be utilized to couple the vertical alignment plate 1140 with the second arm 1120.

Figure 11A:
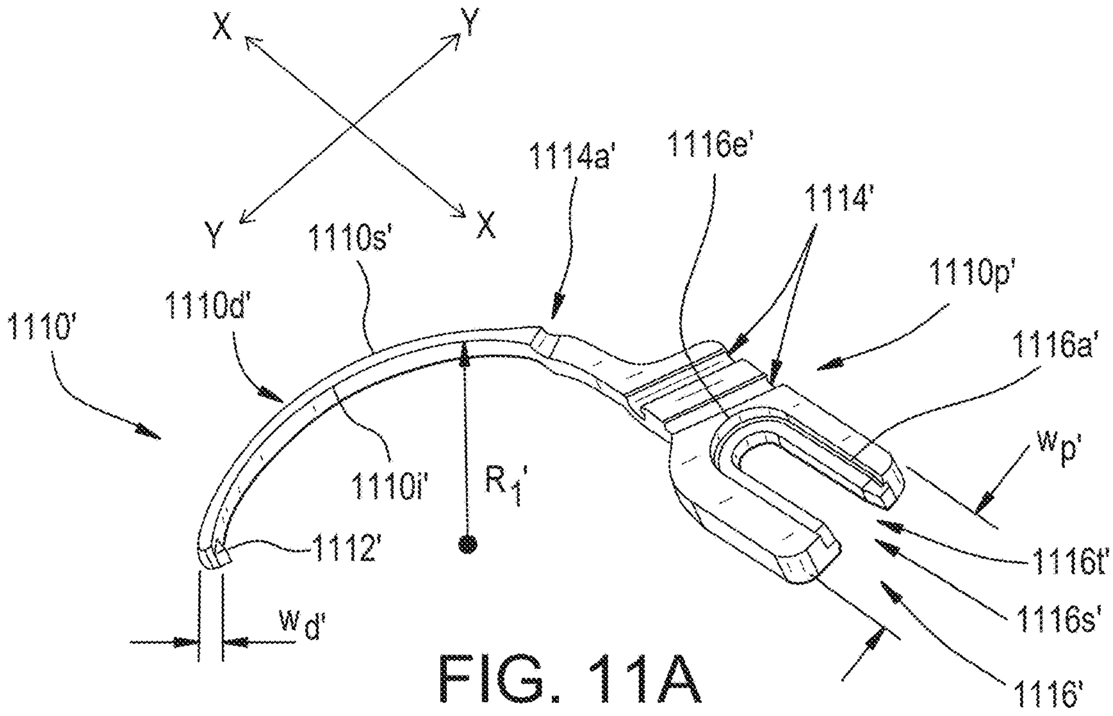
FIG. 11A is a front perspective view of an alternative first arm that can be used in place of the first arm of the humeral resection guide of FIG. 10.
Figure 11B:
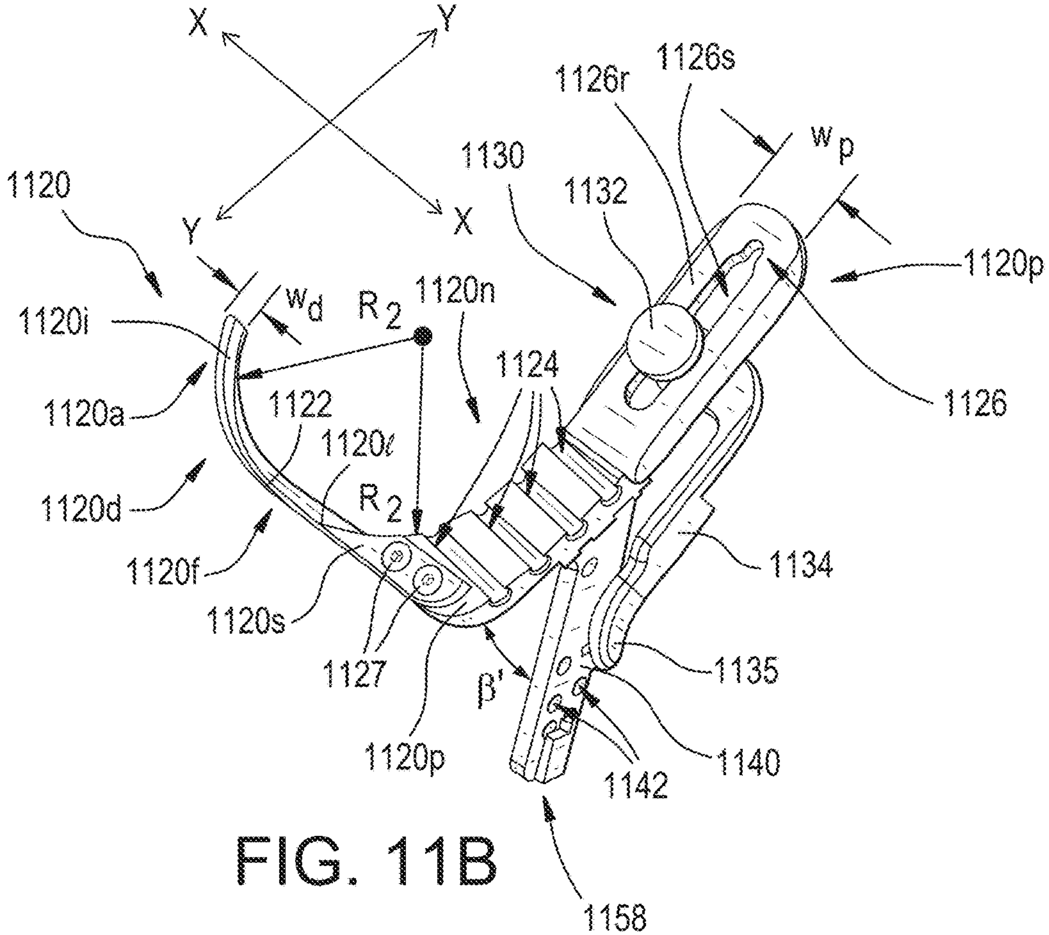
FIG. 11B is a front perspective view of the second arm, and associated locking mechanism and vertical alignment plate, of the humeral resection guide of FIG. 10.

FIGS. 11A and 11B provide for arms 1110', 1120 of a humeral resection guide, like the guide 1100. As shown, a first, superior arm 1110' of FIG. 11A is configured slightly different than the one illustrated in FIG. 10 because an elongated distal member **1110*d*' is longer than an equivalent elongated distal member 1110*d* of the arm 1110 of FIG. 10. The other aspects and features of the arm 1110' are akin to those in the arm 1110, even to the extent such features are not labeled and/or described with respect to the arm 1110 of FIG. 10. The second inferior arm 1120 of FIG. 11B is the same inferior arm 1120 illustrated in FIG. 10**.

The first, superior arm 1110', shown in FIG. 11A, includes a proximal portion **1110*p*' and an elongated distal portion 1110*d*', sometimes referred to as a distal member (equivalent proximal and distal portions 1110*p* and 1110*d* of first arm 1110 are provided for in FIG. 10). The proximal portion 1110*p*' is configured for coupling to or otherwise mating with the second, inferior arm 1120. As shown, a connection feature 1116' is formed as part of the proximal portion 1110*p*' to aid in the mating, the connection feature 1116' including a ledge 1116*a*' that defines a horizontal slot 1116*s*', the ledge 1116*a*' and the slot 1116*s*' being able to receive the screw 1132 of the adjustable connection mechanism 1130 (see FIG. 10 for equivalent ledge 1116*a* and slot 1116*s* of a connection feature 1116 receiving the screw 1132). The slot 1116*s*' can be bound on one end by a closed terminal end 1116*e*', and an opposed, open terminal end 1116*t*'**.

Also formed in the proximal portion **1110*p*' can be one or more bone or guide pin receiving slots 1114'. The slots 1114' can be grooves formed in the proximal portion 1110*p*' for the purpose of receiving one or more bone pins, drill bits, or other similar structures (e.g., a drill bit 1125 disposed in an equivalent slot 1114 in FIG. 10) that can engage the humeral head and/or humerus to help hold the arm 1110', and thus the guide 1100, at a location or position with respect to the humeral head. The location of the slots 1114' can be such that pin placement occurs above or below the subscapularis tendon (within the bicipital groove location), thus preventing any pin(s) disposed therein from passing through the tendon. More particularly, one or more of the slots 1114' can be disposed in a manner such that a drill bit or bone pin that passes therethrough can be tangent to a superior portion of the cutting plane defined by the arms 1110', 1120. This can, in turn, extend a cutting surface along which a cutting tool (e.g., cutting tool 102, or cutting tool 1102, discussed below) that is used to cut and/or resect the humeral head passes to an opposite side of the bone being cut. In the illustrated embodiment of FIG. 10 the received structure is a drill bit 1125 disposed in an equivalent slot 1114, although in other instances the pin can be a pin having a substantially smooth outer surface rather than a grooved outer surface like the drill bit 1125 has. The drill bit 1125 can be positioned tangent to the cutting plane defined by the arms 1110', 1120. As shown in FIG. 11A, the two slots 1114' are parallel, or substantially parallel, to each other, disposed at a slight angle with respect to the Y axis (as shown, approximately 10° from the Y axis, although other configurations are possible). The angular positions of these slots 1114' can be variable as a user can swing the superior arm 1110 to be at any angle with respect to the Y axis. Further, any number of slots 1114', including one or more than two, can be used, and when multiple slots 1114' are used, they do not have to be parallel, or substantially parallel, to each other. The foregoing notwithstanding, it can be beneficial for the slots 1114' to align with the cutting plane such that longitudinal axes extending through a length of the slots 1114', and a length of pins disposed therein, can be aligned or substantially aligned with, or parallel or substantially parallel to, the cutting plane. Still further, additional slots or grooves 1114*a*' can be formed on the arm 1110' to provide for rigidity to resist bending. The grooves 1114*a*', can also help receive pins or the like (e.g., the drill bit 1125**) to grasp other areas of the humeral head and/or humerus at other angles and/or to act as a guide for a cutting blade to help protect tissue.

The distal portion **1110*d*' of the first, superior arm 1110' can be configured to engage the humeral head and/or humerus to help set a location of the resection guide 1100 with respect to the humeral head in conjunction with defining the cutting plane. More particularly, the distal portion 1110*d*' can have a generally arcuate shape with an inner, contoured surface 1110*i*' configured to help grip or otherwise engage bone. The distal portion 1110*d*' can have a general radius of curvature $R_1'$ designed to fit a natural (or considered normal amongst a designated population for that particular arm 1110') curvature around the humeral head. The distal portion 1110*d*' can include one or more gripping protrusions or teeth 1112' disposed on the inner surface 1110*i*', which can help to better grasp and hold the surface of the humeral head and/or humerus. Gripping protrusions or teeth can likewise be placed along any portion of the inner surface 1110*i*' of the first arm 1110', as well as any portion of an inner surface of the second arm 1120**.

A superior surface **1110*s*' of the first arm 1110', as illustrated on the distal portion 1110*d*' but also with respect to the proximal portion 1110*p*', can be substantially flat, thus allowing a cutting tool to pass smoothly along a cutting plane/surface defined by the resection guide 1100. The substantially flat planar surface defined across the superior surface 1110*s*' of the first arm 1110' also helps reduce possible trauma to soft tissue as the arm 1110' is inserted to a surgical site. As shown, a width $w_d'$ of the distal portion 1110*d*' of the arm 1110' is typically substantially smaller than a width $w_p'$ of the proximal portion 1110*p*' of the arm 1110' at least because it is the distal portion 1110*d*'** that is primarily inserted into the surgical site and is the portion that has to extend furthest into the body, thus likely having to navigate through the most tissue.

The second, inferior arm 1120, shown in FIGS. 10 and 11B, includes a proximal portion **1120*p*, an intermediate portion 1120*n*, and an elongated distal portion 1120*d*, sometimes referred to as a distal member. The proximal portion 1120*p* is configured for coupling to or otherwise mating with the first, superior arm 1110 (in FIG. 10) and 110' (of FIG. 11A). As shown, a connection feature 1126 is formed as part of the proximal portion 1120*p* to aid in the mating, the connection feature 1126 including a receiving surface 1126*r* that defines a vertical slot 1126*s*, the receiving surface 1126*r* and the slot 1126*s* being able to receive the screw 1132 of the adjustable connection mechanism 1130. The intermediate portion 1120*n* can have one or more bone or guide pin receiving slots 1124. Similar to the slots 1114 of the first arm 1110, and the slots 1114' of the first arm 1110', the slots 1124 can be grooves formed in the intermediate portion 1120*n* for the purpose of receiving one or more bone pins, drill bits, or other similar structures that can engage the humeral head and/or humerus to help hold the arm 1120, and thus the guide 1100, at a location or position with respect to the humeral head. Also similar to the slots', the location of the slots 1124 can be such that pin placement occurs above or below the subscapularis tendon, thus preventing any pin(s) disposed therein from passing through the tendon. As shown the four slots 1124 are parallel, or substantially parallel, to each other, and are also disposed approximately along or parallel to the X axis (although other configurations, including fewer slots, e.g. one slot, are possible). Further, any number of slots 1124, including one, two, three, or more than four, can be used, and when multiple slots 1124 are used, they do not have to be parallel, or substantially parallel, to each other. The foregoing notwithstanding, it can be beneficial for the slots 1124 to align with the cutting plane such that longitudinal axes extending through a length of the slots 1124**, and a length of pins disposed therein, can be aligned or substantially aligned with, or parallel or substantially parallel to, the cutting plane.

The distal portion 1120*d* of the second, inferior arm 1120 can be configured to engage the humeral head and/or humerus (typically at least a portion of the bone that is different than the distal portion 1110*d* of the first, superior arm 1110 engages) to help set a location of the resection guide 1100 with respect to the humeral head in conjunction with defining the cutting plane. More particularly, the distal portion 1120*d* can have a generally flat portion 1120*f* in an intermediate section of the distal portion 1120*d* and a generally arcuate portion 1120*a* in a tip section of the distal portion 1120*d*. Further, the generally flat portion 1120*f* can include a ledge 11201 upon which a bone surface (e.g., the humeral head or surrounding bone) can sit while being grasped by the second arm 1120. The generally arcuate portion 1120*a* can include an inner, contoured surface 1120*i* configured to help grip or otherwise engage bone, similar to the inner, contoured surface 1110*i*'. Further, the generally arcuate portion 1120*a* can have a general radius of curvature $R_2$ designed to fit a natural (or considered normal amongst a designated population for that particular arm 1120) curvature around the humeral head. As shown, this same radius of curvature $R_2$ can also be formed with the intermediate portion 1120*n* of the arm 1120, while in other embodiments a different radius of curvature can exist for the generally arcuate portion 1120*a* and the intermediate portion 1120*n*. Although not illustrated, similar to the protrusion or tooth 1112', one or more gripping protrusions or teeth can also be disposed on the inner surface 1120*i* of the arm 1120. Further, as shown, the distal portion 1120*d* can include an elevated ridge 1122, the ridge 1122 being raised above an intended cutting plane to serve as a stop for a cutting tool that performs the resection or cut. Although illustrated on the distal portion 1120*d* of the second arm 1120, an equivalent ridge can be formed on the first arm 1110'.

In the illustrated embodiment, the distal portion 1120*d* is mated to the intermediate portion 1120*n* by way of a pair of screws 1127, meaning the distal portion 1120*d* can be separable from the remaining portion of the arm 1120. This optional separation allows the surgeon to optionally replace the distal portion 1120*d* of the arm with an alternative distal portion better sized and/or shaped to fit the patient anatomy. For example, a distal portion can be swapped in that provides for a better fit, better securement, and/or better shielding during cutting, among other benefits appreciable by those skilled in the art in view of the present disclosures. Any coupling mechanism known to those skilled in the art can be use in lieu of, or in addition to, the screws 1127. Further, in other embodiments, the second arm 1120 can be monolithically formed such that the distal portion 1120*d* and the intermediate portion 1120*n* are a single unit, similar to how the proximal and distal portions 1110*p*', 1110*d*' of the first arm are monolithically formed. A person skilled in the art will appreciate that for both the first arms 1110, 1110' and the second arm 1120, portions of such arms can be monolithically formed or they can be formed in various parts akin to the distal portion 120*d* being coupled to the intermediate portion 1120*n*.

Similar to the first arms 1110, 1110', a superior surface 1120*s* of the second arm 1120, as illustrated on the distal portion 1120*d* but also with respect to the proximal and intermediate portions 1120*p*, 1120*n*, can be substantially flat, thus allowing a cutting tool to pass smoothly along a cutting plane/surface defined by the resection guide 1100. The substantially flat planar surface defined across the superior surface 1120*s* of the second arm 1120 also helps reduce possible trauma to soft tissue as the arm 1120 is inserted to a surgical site. As shown, and again similar to the first arms 1110, 1110', a width $w_d$ of the distal portion 1120*d* of the arm 1120 is typically substantially smaller than a width $w_p$ of the proximal portion 1120*p* of the arm 1120 at least because it is the distal portion 1120*d* that is primarily inserted into the surgical site and is the portion that has to extend furthest into the body, thus likely having to navigate through the most tissue. In the illustrated embodiment a width of the intermediate portion 1120*n* is similar to that of the width $w_p$ of the proximal portion 1120*p*, though it does not have to be the same and can, for example, transition to a smaller width as it extends towards the distal portion 1120*d*.

The shapes and sizes of the first arms 1110, 1110' and second arms 1120 can vary on a variety of factors, including but not limited to the anatomy of the patient, the size and shape of the components with which the arms 1110, 1110', 1120, and the guide 1100 more generally, are being used, the type of procedure being performed, and/or the preferences of the surgeon, among other factors. For examples, arms 1110, 1110', 1120 of different lengths can be used for various patient anatomies. Further, different sized arms, and other components of a guide(s) and/or used in conjunction with the guides of the present disclosure can be provided together as a kit.

The connection feature 1116' of the proximal portion 1110*p*' of the first arm 1110' and the connection feature 1126 of the proximal portion 1120*p* of the second arm 1120 are both configured to operate with the adjustable connection mechanism 1130 to selectively mate the first and second arms 1110', 1120 together, and to allow for adjustment of the cutting plane as defined by the first and second arms 1110', 1120 in at least three degrees: (a) sliding of the first arm 1110' in the X direction that is in a direction of travel commensurate with the X axis; (b) sliding of the first arm 1110' in the Y direction that is a in direction of travel commensurate with the Y axis; and (c) rotating the first arm 1110' about the screw 1132 of the X-Y plane defined by the X and Y axes. The coupling between the two arms 1110' and 1120 can be described as a handcuff configuration, the configuration allowing for adjustment across at least these three degrees of freedom to provide a secure fit of the humeral resection guide 1100 to most any size and shape humeral head.

More particularly, and with reference to the equivalent feature 1116 of FIG. 10, the screw 1132 can engage the ledge 1116*a* and pass through the slot 1116*s* of the first arm 1110, as well as pass into, and often through, the slot 1126*s* of the second arm 1120, thus coupling the first arm 1110 and the second arm 1120. The screw 1132 can be moved between an unlocked configuration, in which movement of the first arm 1110 with respect to the second arm 1120 and/or the screw 1132 can occur, and a locked configuration, in which movement of the first arm 1110 with respect to the second arm 1120 and the screw 1132 is constrained or otherwise prevented.

In the unlocked configuration, a first degree of freedom made possible between the two arms 1110, 1120 is the first arm 1110 sliding in the aforementioned X direction. The first arm 1110 slides relative to the second arm 1120 and the screw 1132, with the screw 1132 sliding along the ledge 1116_a_ as the first arm 1110 moves in the X direction. Travel of the first arm 1110 can be limited in one direction by a closed terminal end 1116_e_ of the slot 1116, the closed terminal end 1116_e_ forming a barrier to prevent further travel in that direction. Travel of the first arm 1110 in the opposite direction can end by the first arm 1110 becoming disengaged with the screw 1132 because the screw 1132 has passed out of an opposed, open terminal end 1116_t_ on the opposite side of the slot 1116. When the first arm 1110 becomes disengaged with the screw 1132, the first and second arms 1110, 1120 may no longer be mated, with the first arm 1110 being able to be moved separate and apart from the second arm 1120. In embodiments in which multiple first arms are provided as options for use with the second arm, another first arm can be swapped in for the first arm 1110 and repair procedures performed using the swapped-in first arm.

A second degree of freedom that is possible in the unlocked configuration is the first arm 1110 sliding in the aforementioned Y direction. The first arm 1110 and the screw 1132 slide relative to the second arm 1120, with the screw 1132 sliding within the slot 1126_s_. Travel in the Y direction can be constrained by closed ends on both terminal ends of the slot 1126_s_. As the screw 1132 slides within the slot 1126, the first arm 1110 can travel with the screw, thus causing the first arm 1110 to move in the Y direction.

Still another degree of freedom that is possible in the unlocked configuration is the first arm 1110 rotating about the screw 1132, causing the first arm 1110 to rotate in the X-Y plane defined by the X and Y axes, and thus rotate relative to the second arm 1120 with the screw 1132 serving as a pivot point. While rotation can be a full 360° if desired, in the illustrated embodiment of FIG. 10, rotation of the first arm 1110 is constrained by a portion of the intermediate portion 1120_n_ of the second arm 1120, as shown a wall 1120_t_ that helps define the groove 1124. As shown, the wall 1120_t_ can make contact with a terminal end 1110_te_ of the proximal portion 1110_p_ of the first arm 1110, as well as a second portion 1110_ce_ of the proximal portion 1110_p_ of the first arm 1110, to prevent full 360° rotation of the first arm 1110 in both a clockwise and counterclockwise direction. The three degrees of freedom can be operated independent of each other, or two or all three can occur simultaneously. Manipulation in the X direction, Y direction, and/or rotation about the screw 1132 can be performed manually by an operator's hands, and/or one or more instruments can be connected to the first arm 1110 to allow the first arm 1110 to be manipulated in these three different ways. Alternatively, or additionally, one or more tools can be connected to the second arm 1120 to assist in movement of one arm with respect to the other arm. Examples of this are described with respect to another embodiment, illustrated at least in FIG. 13, although other manipulation tools are possible. By way of non-limiting example, a tool (e.g., tool 2150) can be engaged in one or more of the slots 1114 to help move the first arm 1110 in the X direction, Y direction, and/or rotate about the screw 1132.

As provided for herein, two additional rotational degrees of freedom are made possible by the current configuration: (1) an angle of inclination degree of freedom with respect to the longitudinal axis L, described above as it relates to the use of the vertical alignment plate 1140 for aligning that degree of freedom, and an alternative configuration of an adjustable vertical alignment plate 2140 described below with respect to FIG. 13; and (2) a version degree of freedom in the transverse plane related to adjusting an alignment of the guide 1100 with respect to a forearm or handle. As described above with respect to FIG. 2, the version angle is defined as the angle of rotation in the transverse plane. The natural degree of retroversion in a human shoulder is approximately in the range of about 0° to about 30°. As described, a manipulation tool (e.g., tool 2150) can be inserted into holes formed at a 300 angle in the vertical alignment plate. Once inserted the handle of the tool extends out a 300 retroversion angle and can be aligned with the forearm to set the resection guide at the appropriate 300 retroversion angle.

Figure 12:
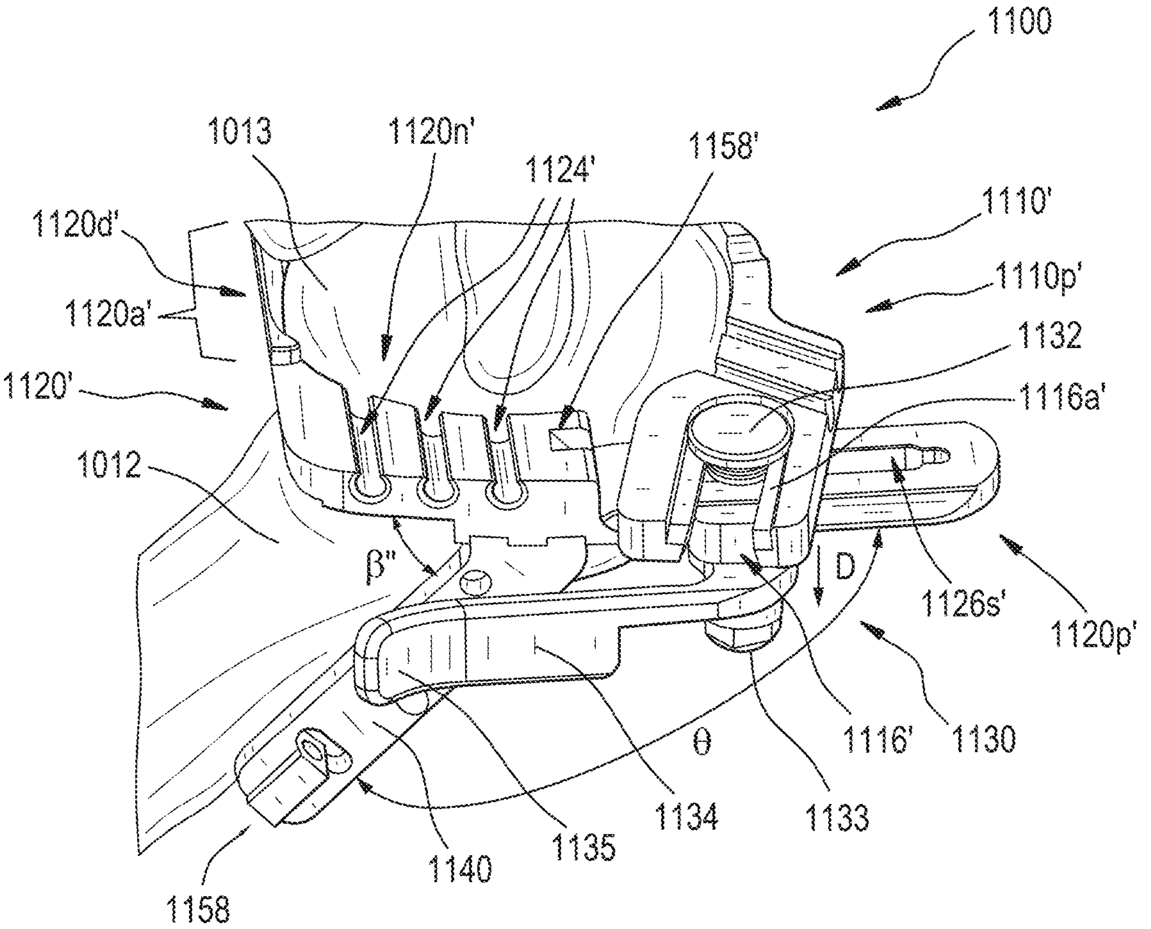
FIG. 12 is a side perspective view of a humeral resection guide that combines the alternative first arm of FIG. 11A with an alternative second arm that is similar to the second arm of FIG. 11B, as well as the locking mechanism and the vertical alignment plate of FIG. 11B, the humeral resection guide being coupled to the humerus of FIG. 2.

Control of the guide 100 to move the adjustable connection mechanism 1130 between the unlocked configuration, in which at least the above described, three degrees of freedom movements are possible, and a locked configuration in which one or more of those degrees of freedom, up to all three degrees of freedom, is prevented, can be controlled by the latch 1134. More particularly, the latch 1134 can engage with a distal end of the screw 1132, for example by way of a tightening receiver 1133 to help move the screw 1132 between the unlocked and locked configurations, this configuration of which his better illustrated in FIG. 12. FIG. 12 combines the first, superior arm 1110' of FIG. 11A with a second, inferior arm 120' that is similar to the second, inferior arm 120 of FIGS. 10 and 11B, but has slight variations, such as only including three bone or guide pin-receiving slots 1124' and a slightly differently shaped distal portion or member 1120_d'_. As shown, the resulting humeral resecting guide 1100 that includes the superior arm 1110' and the inferior arm 1120' is coupled to the humerus 1012, surrounding the humeral head 1013. In particular, rather than the distal portion 1120_d'_ being arcuate like the distal portion 1120_d_, the distal portion 1120_d'_ includes a substantially straight portion 1120_a'_. Further, as shown, the second arm 1120' can include a pin-receiving bore or threaded slot 1158' for receiving a vertical alignment rod, such as the rod 160' described above or a rod 2160_b_ illustrated with respect to FIG. 16. Similar to the second arm 1120, the second arm 1120' can include a slot 1126' formed in a proximal portion 1120_p'_ of the second arm 1120'.

For example, in the embodiments illustrated in FIGS. 10 and 12, the latch 1134 is a locked position, which in turn puts the screw 1132 in the locked configuration. In the locked position, the latch 1134 pulls down and/or tightens the screw 1132 by way of the tightening receiver 1133, which causes the screw 1132 to put a force on the first arm 1110' in a direction D as shown in FIG. 12, towards the distal end of the screw 1132 (as shown, into the page in FIG. 10) sufficient to prevent the first arm 1110' from sliding in the aforementioned X direction. This is at least because the screw 1132 is unable to slide along the ledge 1116_a'_ of the connection feature 1116' due to the force imparted by the latch 1134. Likewise, the force caused by the latch 1134 pulling down in the direction D and/or tightening the screw 1132 in the direction D towards the distal end of the screw 1132 when the latch 1134 is in the locked position can be sufficient to prevent the screw 1132, and thus the first arm 1110' coupled to it, from sliding in the aforementioned Y direction, within the slot 1126_s'_. This is at least because the screw 1132 is locked relative to the second arm 1120, 1120'. Still further, in the locked position, the latch 1134 pulls down and/or tightens the screw 1132 sufficient for the force in the direction D towards the distal end of the screw 1132 to prevent rotation of the first arm 1110' about the screw 1132 itself. In some embodiments, the latch 1134 can be spring loaded, including features such as Bellville washers or a designed flat leaf spring.

As shown, the latch 1134 can include a thumb handle 1135 configured to allow for a user to engage the handle 1135 with a thumb or the like and push the latch 1134 in a direction T as shown in FIG. 10 to move the latch 1134 from the illustrated locked position to an unlocked position. In the unlocked position, the latch 1134 can swing away from the vertical alignment plate 1140, in an approximate path U as shown in FIG. 10. While the latch 1134 is in the unlocked position, the above-described three degrees of freedom are possible. A person skilled in the art will appreciate that the latch 1134 is one of a variety of locking mechanisms that can be used to set positions of the first and second arms 1110, 1110' and 1120, 1120' with respect to each other.

Figure 14:
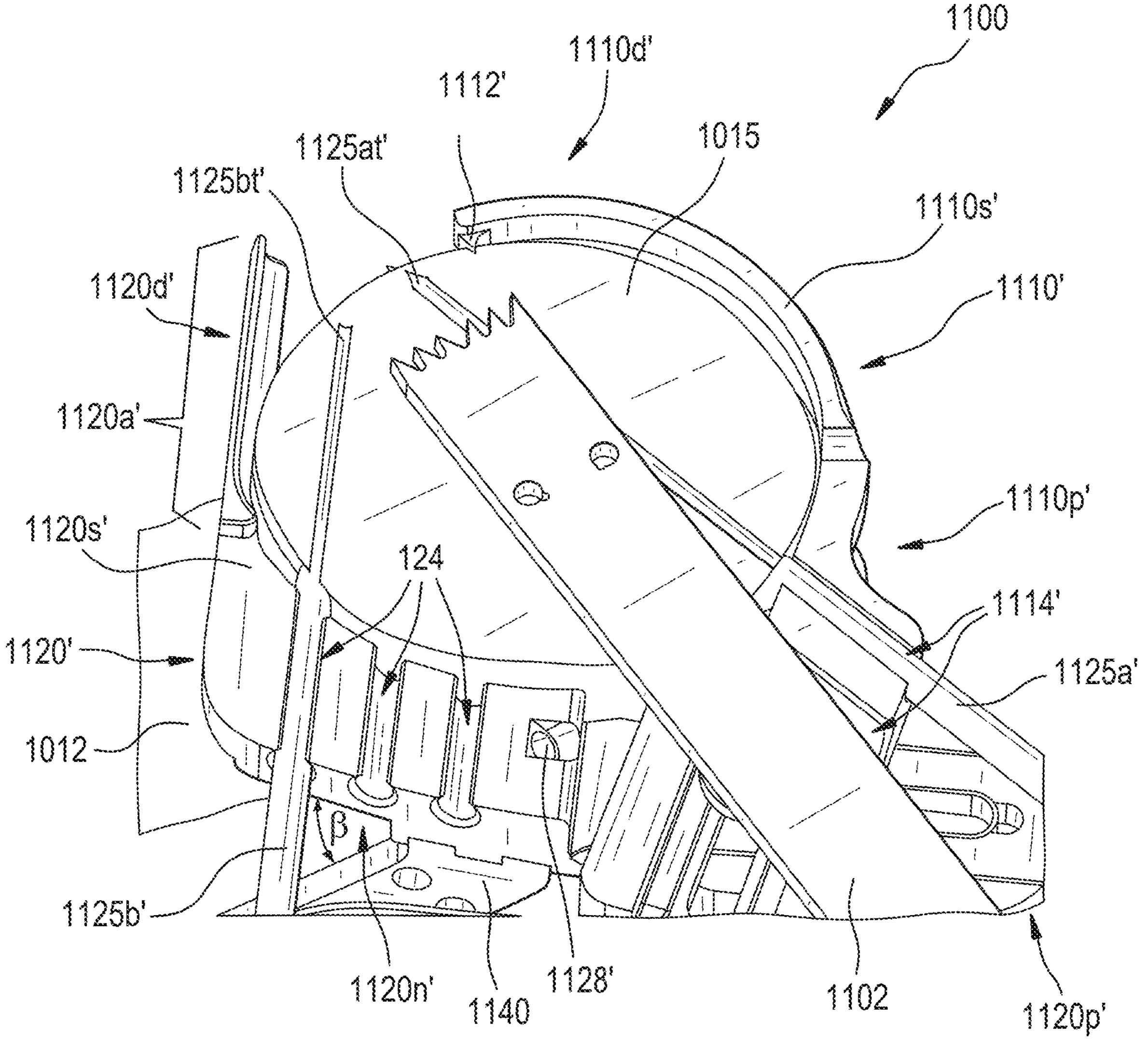
FIG. 14 is a front perspective view of the humeral resection guide of FIG. 12 secured to the humerus of FIG. 2 and having a cutting tool being operated therewith.
Figure 15:
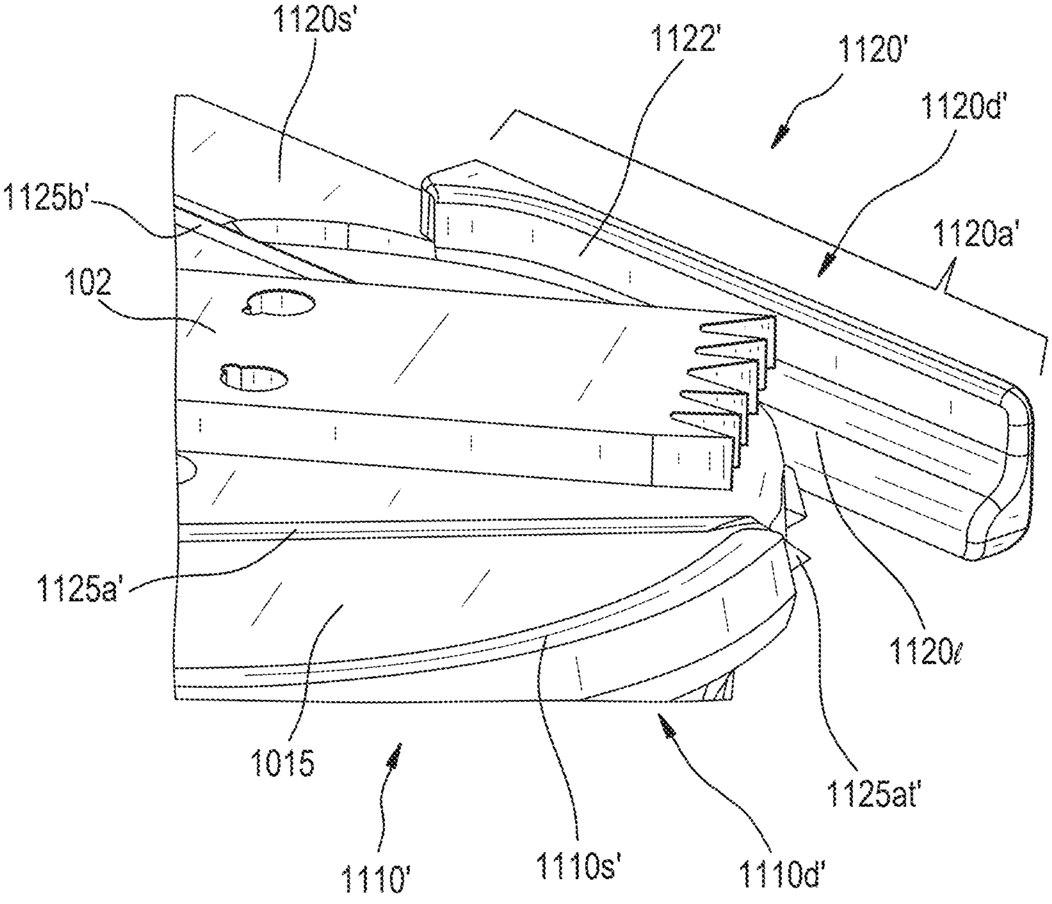
FIG. 15 is a front, detailed perspective view of distal portions of the first and second arms of the humeral resection guide of FIG. 14.

FIGS. 14 and 15 illustrate the use of the humeral cutting guide 1100 in conjunction with a resecting or cutting tool 1102, as shown a sagittal saw, and in particular a humeral resection surface 1015 that results from completion of the resection. The saw 1102 in the illustrated embodiment is a flat bone saw, which can have in at last some instances an approximately 13 mm width, although a variety of other cutting or resection tools having similar or different widths than the illustrated cutting tool can be used. The guide 1100 uses the first and second arms 1110', 1120' to engage the humeral head and/or the humerus 1012. More particularly, the arms 1110', 1120' can grasp the humeral head around its outer surface, for example specifically by aligning along the articular margin (e.g., the articular margin 1009 as illustrated in FIG. 2) or other anatomical landmark. The first, superior arm 1110' can be adapted to grasp an outer surface of the humeral head using an inner, contoured surface, and the second, inferior arm 1120' also can grasp the humeral head, as shown by allowing it to be seated on a ledge 11201" formed as part f the substantially straight portion **1120*a*' of the arm 1120'**.

As shown in FIGS. 14 and 15, the arms 110' and 120' form a humeral guide circumference or perimeter that can provide coverage around a majority of a circumference or perimeter of the humeral head. The circumference of the humeral head, or a bone more generally around which the arms 1110' and 1120' can be disposed, can also be referred to as a perimeter, as the present disclosure is not limited to use with bones having circular or elliptical cross-sectional areas. This coverage by the two arms 1110' and 1120', also referred to as a grasping circumference or grasping perimeter of the arms 1110' and 1120', can be at least about 50% coverage of a circumference of the humeral head or more at the humeral resection surface 1015, including but not limited to at least about 60% coverage, at least about 65% coverage, at least about 70% coverage, at least about 75% coverage, at least about 80% coverage, at least about 85% coverage, at least about 90% coverage, at least about 95% coverage, and 100% coverage of a circumference of the humeral resection surface 1015. In the illustrated embodiment the arms 1110' and 1120' provide approximately 80% coverage of the humeral resection surface 1015. Unlike some other humeral cutting guides, in which coverage of a circumference of the humeral head is 100% because it is in a ring configuration, the guides of the present disclosure enable grasping circumferences that do not extend around an entirety of the circumference or perimeter. Rather, the grasping circumferences of the guide 1100 can be approximately in the range of about 50% to about 95% of the circumference of the bone being cut, or about 50% to about 90%, or about 50% to about 85%, or about 50% to about 80%, or about 50% to about 75%, or about 50% to about 70% of the circumference of the bone being cut, etc.

In some instances, one of the superior arm 1110' or the inferior arm 1120' can be removed, allowing the other arm to be used alone. For example, the inferior arm 1120' can be separated from the superior arm 1110' and removed from the surgical site, allowing the superior arm 1110' to act as the cutting plane. Removing one of the arms can increase visibility, as the guide 1100 with only one arm covers less of the surgical site (e.g., covering some amount less than about 50%). Whether an arm is removed or not, the coverage by opposed arms is more versatile than configurations that may use an entire ring to wrap around a circumference of the humeral head 1013. One embodiment of a guide that covers less than even 50% of the humeral head, and does not include a second arm (though it can, optionally, include an extender 120 as described above) is the guide 100, the guide 100 essentially having just a superior arm, the superior radial arm 110.

Once the arms 1110', 1120' are positioned or otherwise oriented around the humeral head 1013, with around not necessarily requiring 100% circumferential coverage as described above (e.g., it can be greater than 50% circumferential), one or more bone or guide pins **1125*a*', 1125*b*' (which can also be drill bits, by way of non-example of other suitable features) or the like can be passed into and through at least a portion of the humeral head and/or humerus 1012 to help fixate a desired position of the guide 1100 at the desired location with respect to the humeral head. In the illustrated embodiment, a first, superior pin 1125*a*' passes through one of the slots 1114' formed in the first arm 1110' and a second, inferior pin 1125*b*' passes through one of the slots 1124' formed in the second arm 1120'. Both pins 1125*a*', 1125*b*' can extend substantially through most of a cross-sectional area of the humerus 1012, although other dispositions, and/or additional or fewer pins, can be used. The superior pin 1125*a*', by virtue of the configuration of the slot 1114', can be disposed tangent to a superior portion of the cutting plane defined by the arms 1110', 1120' to extend a cutting surface along which a cutting tool (e.g., cutting tool 1102) performing the cutting and/or resecting of the humeral head passes to an opposite side of the bone being cut. Accordingly, as cutting is performed, and at some point a view may of the surgeon may be obstructed, the superior pin 1125*a*' allows the cutting tool to ride the surface of the resection guide 100' and plunge into bone while also riding over the guide pin 1125*a*'. It can thus be important to have an outer surface of the pin 125*a*' tangent to the cutting plane defined by the arms 1110', 1120', a positioning made possible by the slot(s) 1114' configuration. In the illustrated embodiment, the pin 1125*a*' includes a terminal drill tip end 1125*at*' that is pointed, enabling it to cut through the humeral head and/or the humerus 1012 to assist in coupling the humeral resection guide 1100 to the humeral head and/or the humerus 1012. The flat superior surfaces 1110*s*', 1120*s*'** can define a cutting plane around the humeral head.

The guide 1100 can then be used to guide a cutting tool to make the resection or cut, for instance by running the cutting tool 1102 along the flat superior surfaces **1110*s*', 1120*s*'. The guide defines an extended cutting plane along which the cutting tool 1102 can pass, the extended cutting plane being a predicted or designed trajectory, such as matching the plane defined by the articular margin 1009, and pins 1125*a*', 1125*b*' can also help provide or otherwise define the extended cutting plane by being positioned tangent to the cutting plane. The pins 1125*a*', 1125*b*' can also help prevent a cutting tool 102 from passing below the cut plane. Further, the guide 100 is designed in a manner that enables the cutting tool 1102 to approach the surgical site through the rotator interval 1020 (see FIG. 2), the same location through which the superior arm 1110' can enter in at least some embodiments, and which is a different approach that typical procedures used for resecting or cutting the humeral head. Further, the guide 1100 as designed enables accurate humeral head resection and/or cutting. An elevated ridge 1122' can serve as a backstop, preventing the cutting tool 1102 from going further into a body and accidentally cutting tissue or the like proximate to the humeral head. The elevated ridge 1122' allows surgeons to forego having to make partial cuts to avoid the cutting tool 1102** traveling too far and causing trauma to surrounding tissue and the like. Partial cuts in these types of procedures is common in prior art techniques at least for this reason.

Third Embodiment of a Humeral Resection Guide and Related Components

A third embodiment of a humeral resection guide 2100 coupled to the humerus 1012 is illustrated in FIG. 16. A number of components of the resection guide 2100 are similar to those of resection guides 100, 1100, and thus repetitive explanations of the same are not necessary in at least some instances. The foregoing notwithstanding, a person skilled in the art, in view of the descriptions and illustrations provided, will understand some mechanical and/or otherwise operational differences between some of the like-numbered components, such explanation(s) of differences not always being necessary because of the knowledge of the skilled person. For example, as discussed in greater detail below, there is a mechanical difference in how the adjustable connection mechanism 2130 operates to couple first and second arms 2110, 2120 of the resection guide 2100 as compared to the adjustable connection mechanism 1130 operates to couple the first and second arms 1110 (or 1110'), 1120 of the resection guide 1100. This is at least because a horizontal slot 2116*s* of a connection feature 2116 does not include an open end like the open terminal end 1116*t* (or 1116*t'*). Nevertheless, a person skilled in the art will appreciate that at least some of the same purposes of the connection mechanism 1130 are carried out by the connection mechanism 2130, such as selectively coupling the two arms 2110, 2120 together and enabling degree(s) of freedom adjustment between the two arm 2110, 2120, and will further understand now the mechanical components of the connection mechanism 2130, and related components (e.g., the connection feature 2116), operate without requiring a full explanation of the same.

Similar to the humeral resection guide 1100, the humeral resection guide 2100 can include a first, superior arm 2110 and a second, inferior arm 2120, the arms 2110, 2120 being the portion of the guide 2100 designed to enter a joint space and engage the humeral head 1013 extending from the elongate shaft 1014 of the humerus 1012. The first, superior arm 2110 can have many similar features as the first, superior arm 1110, and the superior radial arm 110 in at least some instances, with the first, superior arm 2110 including a proximal portion 2110*p* and an elongated distal portion or member 2110*d*. The proximal portion 2110*p* can include, for example, a connection feature 2116, as well as bone pin receiving slots 2114, and/or additional slots or grooves 2114*a*. The connection feature 2116 in the first arm 2110 includes both a ledge 2116*a* and a slot 2116*s* formed in the superior arm 2110, but in the slot 2116*s* differs from the slot 1116*s* in that it is closed at both ends 2116*e*, 2116*t* preventing separation of the first and second arms 2110, 2120. Additionally, at least in the illustrated embodiment, given how close a terminal end 2110*te* and a second portion 2110*ce* of the first arm 2110 is to a wall 2120*t* that helps define a groove 2124 of the second arm 2120, rotation of the first arm 2110 with respect to the second arm 2120 can be more limited for the guide 2100 as compared to the guide 1100. A person skilled in the art, however, will appreciate configuration changes that can be made to permit more rotation, up to full 360° rotation of the first arm 2110. The distal portion 2110*d* can include many of the same features described above with respect to the distal portion 1110*d* that enable it to engage the humeral head 1013 and/or the humerus 1012 and help set a location of the resection guide 2100 with respect to the humeral head 1013 in conjunction with defining the cutting plane.

The second, inferior arm 2120 can likewise have many similar features as the second, inferior arm 1120. This includes, for example, a proximal portion 2120*p* and an elongated distal portion or member 2120*d*. While the second arm 1120 also includes the intermediate portion 1120*n*, features from the intermediate portion 1120*n*, such as the bone pin receiving slots 1124, are provided for in the proximal portion 2120*p*, as shown bone pin receiving slots 2124 being part of the proximal portion 2120*p*. This helps illustrate that various features of proximal, intermediate, and distal portions can be separate portions of the various guides provided for herein can be interchangeable across portions and that the portions themselves can be separate or combined. The second arm 2120 is coupled to the first arm 2110, for example by way of an adjustable control or connection mechanism 2130, which can include a screw 2132 disposed within a slot in the inferior arm (not shown) equivalent to the slot 2116*s* of the superior arm 2110. The illustrated first arm 2110 can rotate about the Z axis, translate in the X direction, at least due to the slot 2116*s*, and translate in the Y direction, at least due to a slot (not visible, but can be akin to the slot 1126*s*) formed in the second arm 2120. The distal portion 2120*d* can include many of the same features described above with respect to the distal portion 1120*d* that enable it to engage the humeral head 1013 and/or the humerus 1012 and help set a location of the resection guide 2100 with respect to the humeral head 1013 in conjunction with defining the cutting plane. In the illustrated embodiment, the distal portion 2120*d* is monolithically formed with the proximal portion 2120*p*, as opposed to using a coupling mechanism like screw 1127 for coupling the distal portion 1120*d* to the intermediate portion 1120*n*. In other instances, the distal portion 2120*d* can be separately formed from the proximal portion 2120*p*, and coupling mechanisms like screws or other known coupling features can be used to couple the distal portion 2120*d* to the proximal portion 2120*p*.

The adjustable control or connection mechanism 2130 can be used to mate the first and second arms 2110, 2120 together, and to allow for adjustment of the cutting plane as defined by the first and second arms 2110, 2120 in at least three degrees: (a) sliding of the first arm 2110 in the X direction that is in a direction of travel commensurate with the X axis; (b) sliding of the first arm 2110 in the Y direction that is in a direction of travel commensurate with the Y axis; and (c) rotating the first arm 2110 about the screw 2132 of the X-Y plane defined by the X and Y axes. Similar to the connection mechanism 1130, in at least some instances the connection between the two arms 2110, 2120 can allow for infinite movement options across the two degrees of freedom (three degrees of freedom with respect to the connection mechanism 1130), although in at least some instances that infinite travel can be limited by various stops or other designs formed in features of the first and second arms 2110, 2120 (e.g., the wall 2120*t*).

Similar to the adjustable connection mechanism 1130, the screw 2132 of the adjustable connection mechanism 1130 can engage the ledge 2116*a* and pass through the slot 2116*s* of the first arm 2110, as well as pass into, and sometimes through, a slot or other aspect of the second arm 2120, as shown a receiving block 2123 adapted to receive the screw 2132, that enables the screw 2132 to engage and selectively couple the first and second arms 2110, 2120 together. The screw 2132 can be moved between an unlocked configuration, in which movement of the first arm 2110 with respect to the second arm 2120 and/or the screw 2132 can occur, and a locked configuration, in which movement of the first arm 2110 with respect to the second arm 2120 and the screw 2132 is constrained or otherwise prevented. The operation of the screw 2132 to move it between unlocked and locked configurations can be accomplished, for example, by rotating a locking handle or tool 2134 to loosen or tighten the screw 2132, respectively. Other operations are generally understood by a person skilled in the art, in view of the present disclosures, and thus a more detailed explanation of how the screw 2132 is placed into these two configurations is unnecessary.

In some embodiments, the locking tool 2134 can be provided. The locking tool 2134 in the illustrated embodiment includes a distal end 2134*d* configured to engage with some portion of the connection mechanism 2130. As shown the distal end 2134*d* comprises an expandable male mating feature 2134*e* adapted for engaging a complementary female mating feature (not shown) associated with the receiving block 2123 coupled to or otherwise associated with the second arm 2120. The distal end 2134*d* can be configured such that its expandable male mating feature 2134*e* is biased in an expanded configuration such that it defaults to engaging the complementary female mating feature when disposed in the receiving block 2123. Pushing a button 2134*b* on the first arm-adjusting tool 2134 can cause the expandable male mating feature 2134*e* to contract so that the tool 2134 can be detached from the receiving block 2123. The tool 2134 can also include a handle 2134*h* to permit easy handling and manipulation of the tool 2134. For example, when the tool 2134 is coupled to the receiving block 2123, the handle 2134*h* can be grasped by an operator and one or more features of the humeral resection guide 2100 can be moved through one or more degrees of freedom. Further, while coupled to the guide, the locking tool 2134 can be used to unlock the connection 2130 between the superior and inferior arms 2110, 2120 so that the second arm 2120 can pivot relative to the first arm 2110 in a direction along the X axis. Locking and unlocking the pivot connection between the arms 2110, 2120 can allow for sizing adjustment. When the screw 2132 is locked, the handle 2134*h* can be used as a handle.

A manipulation tool, as shown a version handle 2150, can also be provided. The manipulation tool 2150 in the illustrated embodiment includes a distal end 2150*d* configured to engage with slots 2114 formed in the first arm 2110 and/or slots 2124 formed in the second arm 2120. Accordingly, as shown, the distal end 2150*d* includes a pitchfork style configuration with opposed first and second posts 2150*p* sized and shaped to pass into the slots 2114. The posts 2150*p* can be similarly sized and shaped, or alternatively, one post may be longer than the other post. Other numbers of posts are also possible, including a single post or more than two posts. The tool 2150 can also include a handle 2150*h* to permit easy handling and manipulation of the tool 2150. For example, when the tool 2150 is coupled to the first arm 2110, it can be operated to provide at least two degrees of freedom for the first arm 2110: (a) moving it in a direction commensurate with the X axis such that the first arm 2110 moves relative to the screw 2132 and the second arm 2120; and (b) rotating the first arm 2110 about the screw 2132 such that the screw 2132 provides a pivot point. Further, when other components are in unlocked configurations as provided for herein, such as when a vertical alignment plate 2140 is able to move relative to the second arm 2120, the tool 2150 coupled to the first arm 2110 can assist in adjusting an angle β' (as described in greater detailed below with respect to the vertical alignment plate 2140). Still further, although the tool 2150 is illustrated to couple with the first arm 2110 to manipulate the same, the tool 2150 can likewise be disposed in the slots 2124 of the second arm 2120 to provide a way to manipulate the second arm 2120 relative to various components of the guide 2100 and/or otherwise associated with the guide 2100, such as the first arm 2110 and the vertical alignment plate 2140. More generally, a person skilled in the art, in view of the present disclosures, will appreciate that the tool 2150 can be easily and quickly inserted into and removed from the slots 2114 and/or the slots 2124, providing for a quick and easy way to manipulate aspects of the humeral resection guide 2100 while adjusting it to set the desired cutting plane, among other features of the guide 2100. In fact, both the tool 2134 and the tool 2150 are designed to be quick-release tools for efficient manipulation of the various components of the guide 2100 during use.

The humeral resection guide 2100 also can include, or otherwise be associated with, a vertical alignment plate 2140. The vertical alignment plate 2140 of the present disclosure differs from the vertical alignment plate 1140 at least because the vertical alignment plate 2140 includes features, and/or is used in conjunction with features, not illustrated with respect to the vertical alignment plate 1140 for purposes of adjusting an orientation of the plate 2140 with respect to the second arm 2120. For example, a link arm 2141 is coupled to the vertical alignment plate 2140 by way of a screw 2148, and the link arm 2141 is also mechanically engaged with a bottom surface 2120*b* of the second arm 2120. The bottom surface 2120*b* can include a plurality of protrusions 2120*c* that are designed to be engaged by the link arm 2141, with the link arm 2141 being able to be moved between the protrusions 2120*c*. Depending on which protrusions 2120*c* are engaged by the link arm 2141, an angle β' formed between the inferior arm 2120 and the vertical alignment plate 2140 can be adjusted. As described above with respect to the angle α', adjusting the angle α" can adjust a cutting plane angle of inclination with respect to a longitudinal axis L". The screw 2148 can be tightened to set an angle β" between a bottom surface of the inferior arm 2120 and the vertical alignment plate 2140, and in turn the angle α", by locking a position of the link arm 2141 with respect to the second arm 2120, the link arm 2141 typically sitting flush with the protrusions 2120*c* at various, predesignated angles associated with the protrusions 2120*c*. The values of the angles α" and β" can be akin to their counterpart angles α' and ρ' described above. Specifically, each protrusion 2120*c* can be formed to set angles β" of about 45°, about 55°, and about 62°, which provides angles of inclination α" of about 145°, 135°, and 128°, respectively. A person skilled in the art will appreciate these three angles are typical humeral cut angles surgeons often target. Further, a person skilled in the art will appreciate other angles can be designed to be achieved, for example by moving and/or providing other protrusions 2120*c*. The screw 2148 can be loosened to allow for the link arm 2141 to be movable with respect to the second arm 2120, moving the link arm 2141 to the various locations at which it can be locked to set the angle β". A person skilled in the art will appreciate other mechanical component that can be used in lieu of or in addition to the screw 2148 without departing from the spirit of the present disclosure.

Another feature associated with the vertical alignment plate 2140 for adjusting an orientation of the plate 2140 with respect to the second arm 2120 comprises a vertical alignment adjustment mechanism 2146. As shown, the vertical alignment adjustment mechanism 2146 can include a spring-loaded screw 2147 bias in a direction towards the vertical adjustment plate 2140. A spring 2145 can provide the bias such that pulling on the screw 2147 in a direction P places the vertical alignment adjustment mechanism 2146 in a unlocked configuration, allowing the vertical alignment plate 2140 to rotate with respect to the first and second arms 2110, 2120, while releasing the screw 2147 such that a force in the direction P is no longer being placed on the screw 2147 places the vertical alignment adjustment mechanism 2146 in a locked configuration, setting a position of the vertical alignment plate 2140 relative to the first and second arms 2110, 2120.

In at least some embodiments, one or more vertical extension or alignment rods 2160*a*, 2160*b* can be coupled to or otherwise associated with the humeral resection guide 2100. This can occur prior to securing the guide 2100 to the humerus 1012, although it is possible such coupling or otherwise association can occur after securing the guide 2100 to the humerus 1012. In the illustrated embodiment, a first rod 2160*a* is coupled to the vertical alignment plate 2140, and a second rod 2160*b* is coupled to the second arm 2120. In other embodiments, a rod like the rods 2160*a*, 2160*b* can be coupled to the first arm 2110. The rods 2160*a*, 2160*b* can assist in providing visualization of the orientation of various features of the resection guide 2100 when the guide 2100 is disposed at the surgical site, as well as providing a way to manipulate aspects of the guide 2100 and/or associated with the guide 2100 from a location remote of the surgical site, including outside of a patient's body. For example, the rod 2160*a* coupled to the vertical alignment plate 2140 can extend a length of the plate 2140 to help make it easier to align the same with, for example, the elongate shaft 1014 of the humerus 1012. The rod 2160*a* can also be used to help manipulate vertical alignment plate 2140 from a location a distance away from the surgical site, including outside of the body. Similarly, the rod 2160*b* coupled to the second arm 2120 can provide visualization and manipulation benefits. Movement afforded by the rods 2160*a*, 2160*b* can be across any number of the degrees of freedom afforded by the configuration of the guide 2100. Further, the rods 2160*a*, 2160*b* can be used to align with other anatomical features beyond just the elongate shaft 1014 of the humerus 1012.

Fourth Embodiment of a Humeral Resection Guide and Related Components

Figure 17A:
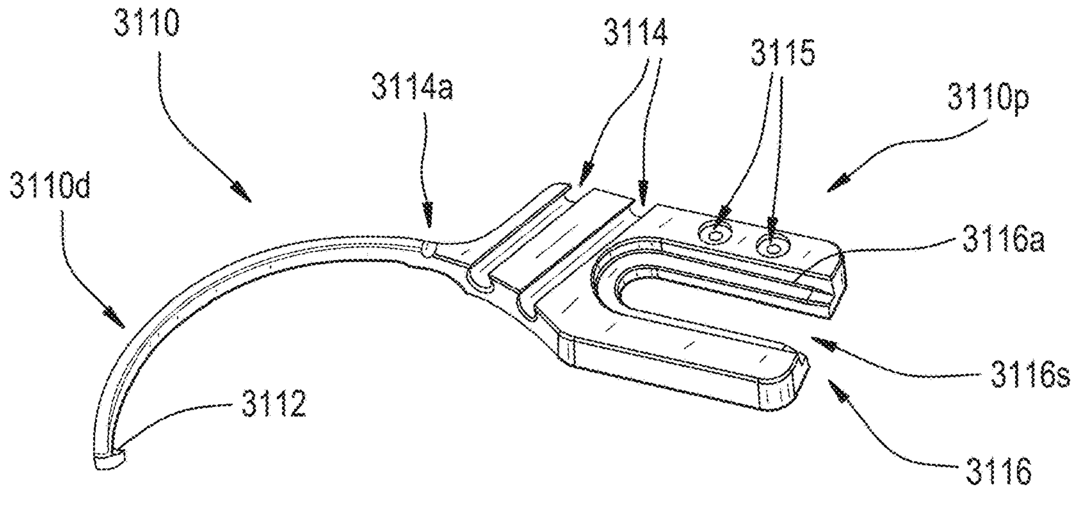
FIG. 17A is a front perspective view of another alternative first arm that can be used in place of the first arm of the humeral resection guide of FIG. 10.
Figure 17B:
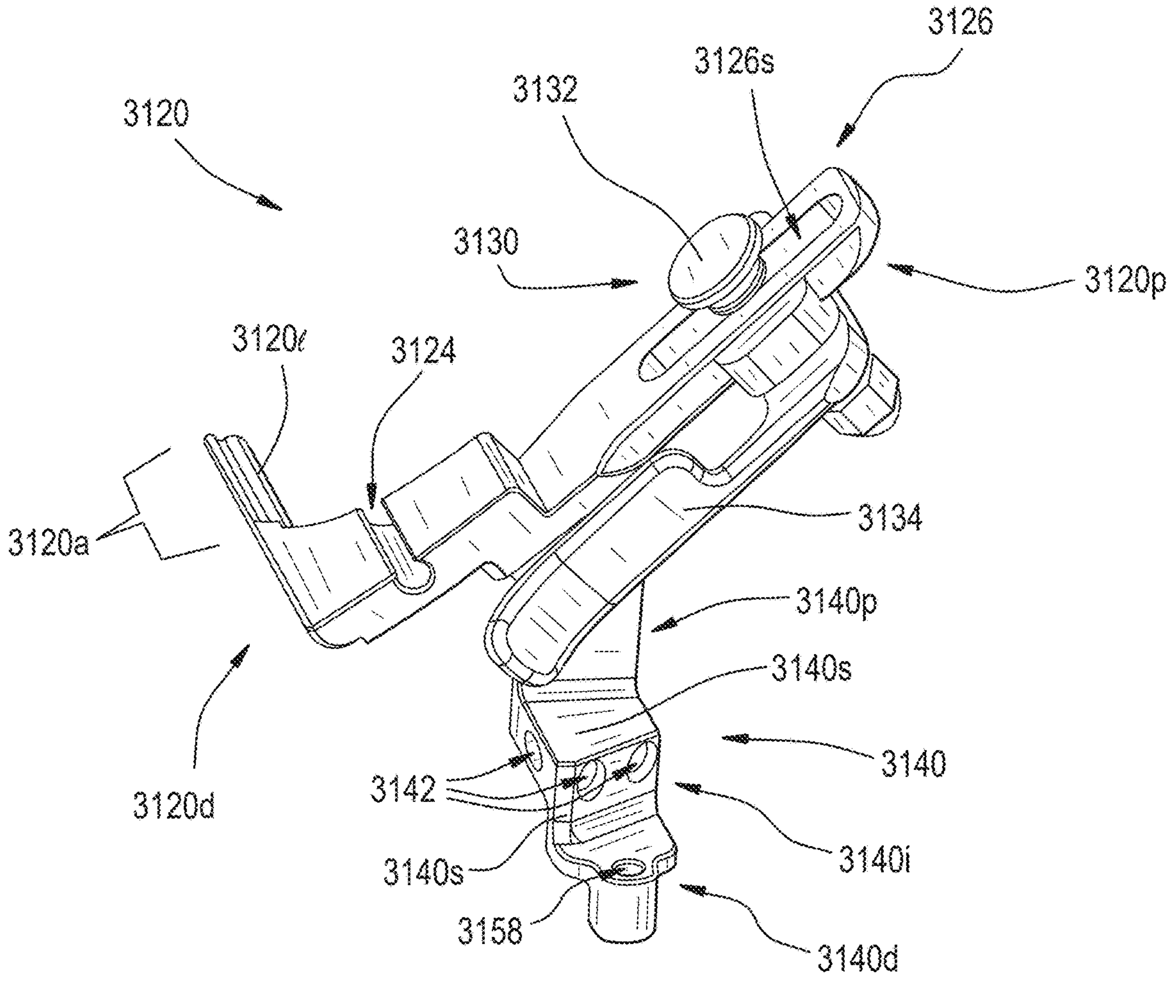
FIG. 17B is a front perspective view of an alternative second arm, and associated alternative locking mechanism and alternative vertical alignment plate, that can be used in place of the second arm, locking mechanism, and vertical alignment plate of the humeral resection guide of FIG. 10.
Figure 18A:
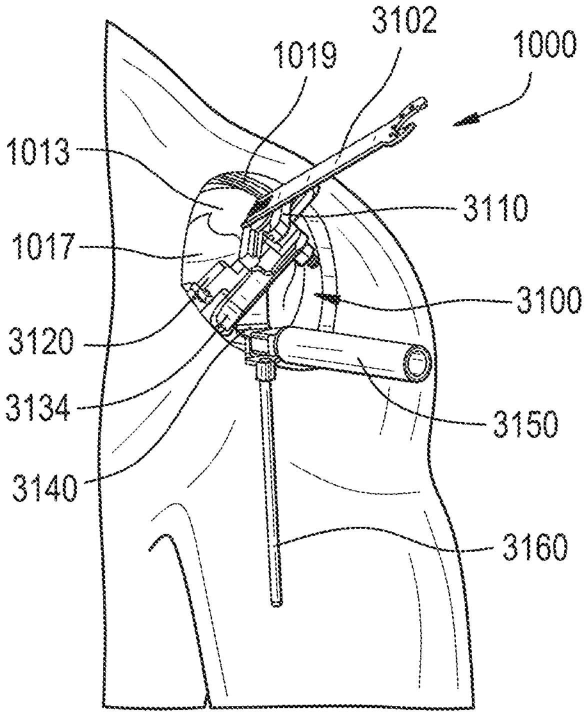
FIG. 18A is a schematic side perspective view of still another embodiment of a humeral resection guide, cutting tool, and related components disposed at the human glenohumeral joint space of FIG. 2 illustrated at a surgical site within a human shoulder.
Figure 18B:
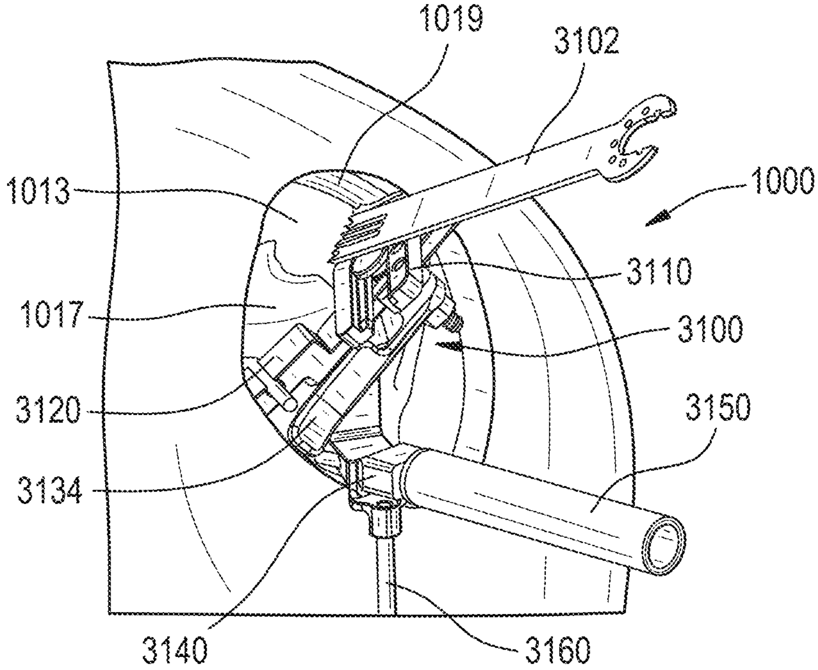
FIG. 18B is a zoomed in view of the schematic side perspective view of FIG. 18A.
Figure 18C:
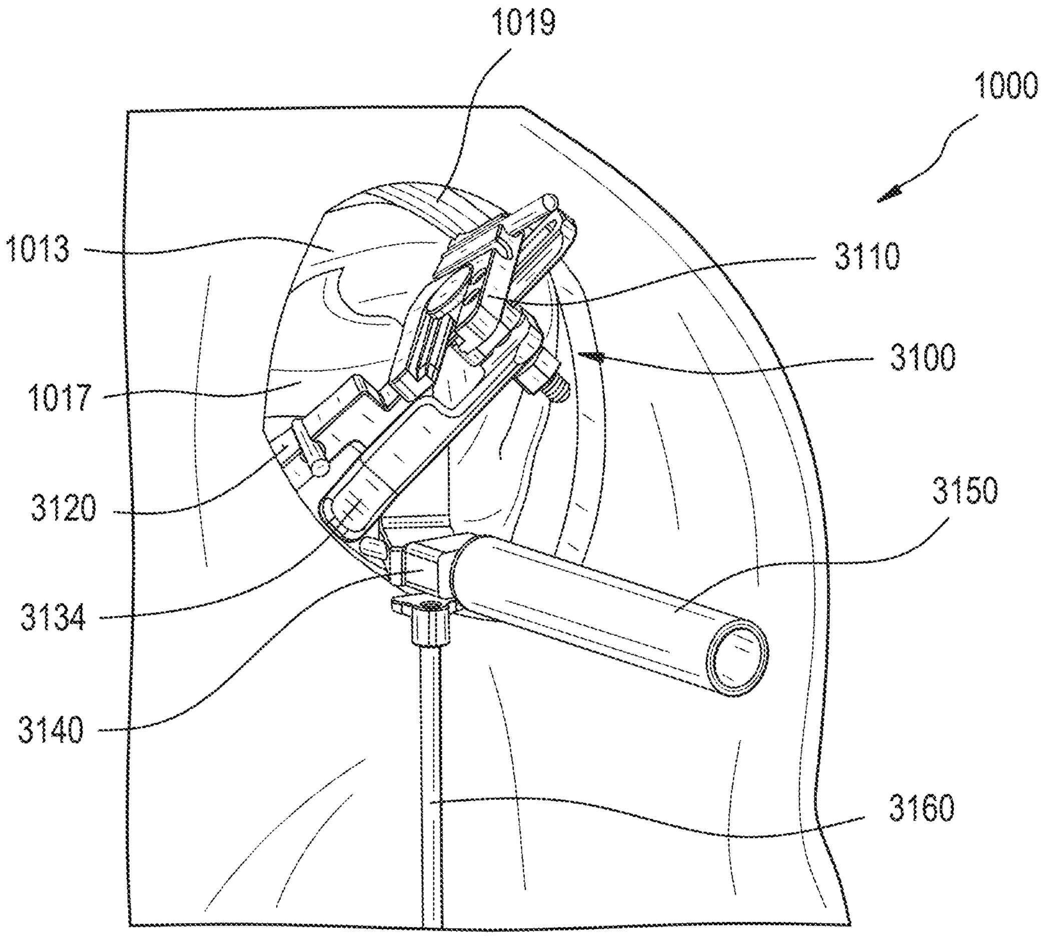
FIG. 18C is the zoomed in view of the schematic side perspective view of FIG. 18B with the cutting tool removed.

FIGS. 17A and 17B illustrate alternative embodiments of first, superior and second, inferior arms 3110, 3120, respectively. The first, superior arm 3110 has many similar features and configurations as the other first, superior arms 110, 1110, 1110', 2110 disclosed herein, and is most akin, in at least some respects, to the superior arm 1110'. Accordingly, for the sake of brevity, each and every feature of the first, superior arm 3110 is not illustrated and/or labeled, though a person skilled in the art, reviewing the entirety of the application and all figures will understand the common and/or illustrated features of the first, superior arm 3110. Some such common features include a proximal portion 3110*p* configured for coupling or otherwise mating with the second arm 3120 and an elongated distal portion 3110*d* configured to engage the humeral head, and/or bone proximate to the humeral head, to help set a location of a humeral resection guide 3100—the humeral resection guide 3100 including the combination of the first and second arms 3110, 3120 as illustrated in FIGS. 18A-18C—with respect to the humeral head in conjunction with defining the cutting plane. The proximal portion 3110*p* can include a connection feature 3116 to aid in mating with the second arm 3120, the connection feature 3116 including a ledge 3116*a* that defines a horizontal slot 3116*s* to receive a screw 3132 or other component of an adjustable connection mechanism 3130. Similar at least to the first arm 1110', the first arm 3110 can include one or more bone or guide pin receiving slots 3114 formed in the proximal portion 3110*p*. A further feature not provided for in the first arm 1110', however, is the inclusion of one or more adjustment holes 3115, as shown two holes, formed through the proximal portion 3110*p* of the arm 3110, proximate to the slot 3116*s*. These holes 3115 can be configured to receive a manipulation tool (e.g., version handle), the manipulation tool being able to be disposed in one or more of the holes 3115 to in turn manipulate or otherwise move the arm 3110 with respect to the second arm 3120, such as by sliding the first arm 3110 with respect to the second arm 3120 and/or rotate the first arm 3110 with respect to a pivot point formed by the screw 3132, as well as verify version as provided for herein with respect to other similar tools, such as the tools 150, 1150, and 2150.

The second, inferior arm 3120 has many similar features and configurations as the other second, inferior arms 1120, 1120', 2120 disclosed herein, and is most akin, in at least some respects, to the inferior arm 1120'. Accordingly, for the sake of brevity, each and every feature of the second, inferior arm 3120 is not illustrated and/or labeled, though a person skilled in the art, reviewing the entirety of the application and all figures will understand the common and/or illustrated features of the second, inferior arm 3120. Some such common features include a proximal portion 3120*p* having a slot 3126*s* that serves as a connection feature 3126 and a distal portion 3120*d* that includes a substantially straight portion 3120*d* with a ledge 31201, the proximal and distal portions 3120*p*, 3120*d* being configured similar to the proximal and distal portions 1120*p*', 1120*d*' unless otherwise noted or understood to be different by a person skilled in the art. As shown, the second arm 3120 only includes a single pin-receiving slot 3124, and it is formed in the distal portion 3120*d*, rather than, for example, the three pin-receiving slots 1124 illustrated with respect to the proximal portion 1120*p* of the second arm 1120. Similar to other embodiments, a locking feature, as shown a latch 3134, can be used to move the adjustable connection mechanism 3130 between unlocked and locked configurations to unlock and lock the ability of the first and second arms 3110, 3120 to move with respect to each other.

In the illustrated embodiment, a vertical alignment plate 3140 has a different configuration than previously described vertical alignment plates 1140, 2140, with the design being conducive to providing clearance to patient tissue and muscle by coming down and then moving anterior. More particularly, as shown, a proximal portion 3140*p* of the vertical alignment plate 3140 couples to the second arm 3120, while an intermediate portion 3140*i* extends substantially at a right angle with respect to the proximal portion 340*p* such that the intermediate portion 3140*i* extends outward from the second arm 3120, and thus outward from a bone with which the vertical alignment plate 3140 is intended to be aligned during use. The intermediate portion 3140*i* is defined as a block or square or rectangular prism, although other shapes and configurations are possible. One or more holes, as shown three, though at least a fourth can be disposed in a surface that is opposed to the surface in which a single hole 3142 is formed, can be formed in the intermediate portion 3140*i*. The holes 3142 can be used in conjunction with providing alignment, such as for receiving tools used in checking and/or adjusting the version alignment of the resection guide 3100, similar to the holes 1142 of the vertical alignment plate 1140. Unlike other embodiments, because the intermediate portion 3140*i* is more thickness, the holes 3142 can be disposed across multiple axes, thus allowing for more varied manipulation approaches. Further, in the illustrated embodiment, a top surface 3140*s* of the intermediate portion 3140*i* has a trapezoidal shape, although other configurations are possible.

As shown, a distal portion 3140*d* of the vertical alignment plate 3140 also extends substantially at a right angle with respect to the intermediate portion 3140*i* such that the distal portion 3140*d* extends outward from the second arm 3120 even further than the intermediate portion 3140*i*. A rod-receiving threaded bore 358 can be formed in the distal portion 3140*d*, and can be configured to receive a rod 3160 (see FIGS. 18A-18C), the rod 3160 being akin to the rods 160, 160', 1160, 2160*a*, 2160*b* such that it can be used to align with the elongate shaft 1014 of the humerus 1012. More particularly, in at least some embodiments, the rod 3160 can be aligned in a manner such that the guide 3100 is positioned at a desired retroversion angle, in turn defining the cut plane at the desired retroversion angle.

FIGS. 18A-18C are schematic illustrations to provide further context of how a humeral resection guide, as shown the humeral resection guide 3100, and other components with which it can be used can be positioned with respect to a body, as shown a human shoulder 1000. The other illustrated components include the rod 3160, a manipulator tool 3150, such as a version handle akin to the tools 150, 1150, 2150, and a cutting tool 3102, akin to the cutting tools 102, 1102. In FIG. 18C, the cutting tool 3102 is removed to provide better visualization of the first arm 3110 and other components and/or aspects that are hidden from view by the cutting tool in FIGS. 18A and 18B.

Figure 19:
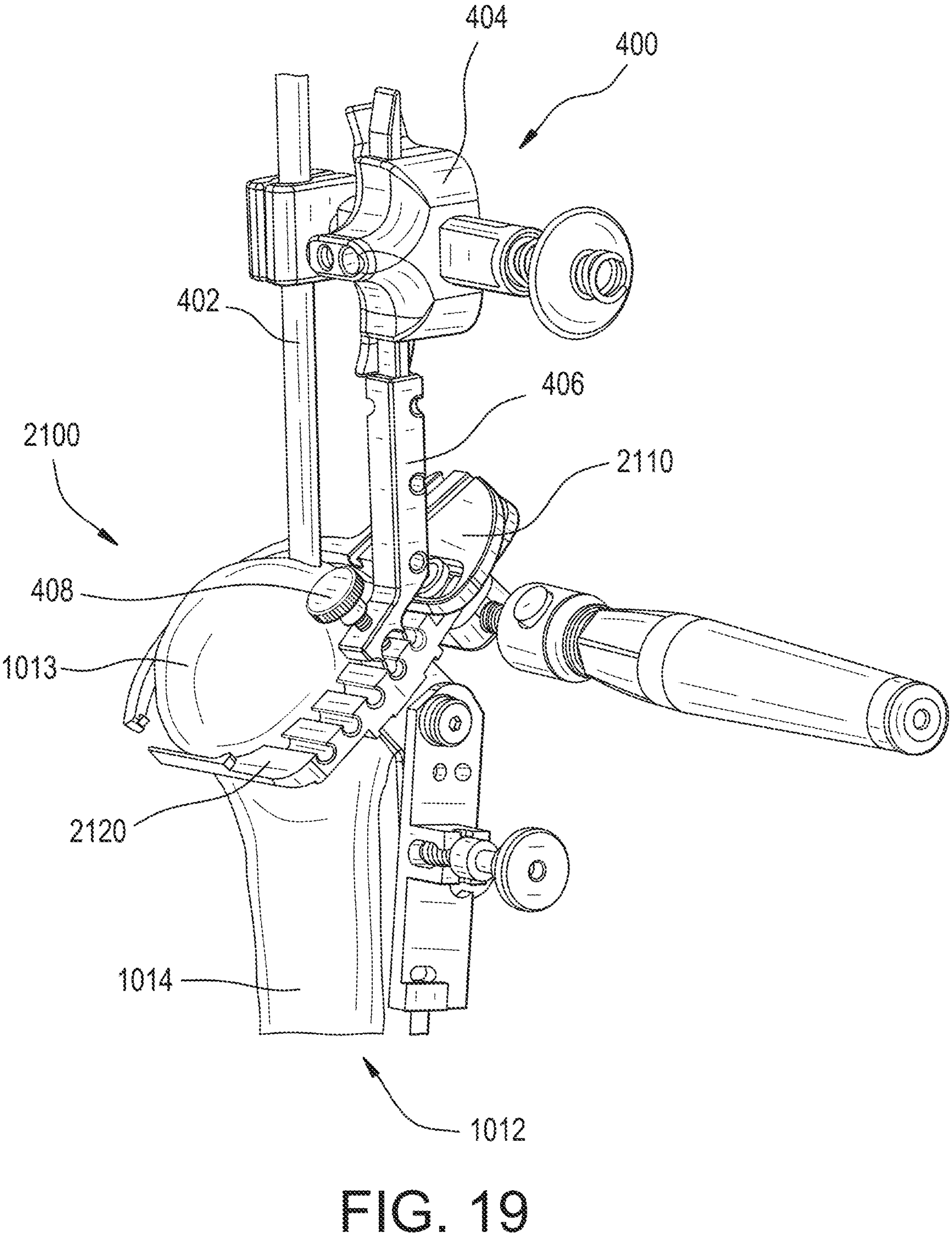
FIG. 19 is a perspective view of the humeral resection guide and humerus of FIG. 16 having an intramedullary guide associated therewith.

The humeral resection guides 100, 1100, 2100, 3100 disclosed herein can be used in conjunction with surgical tools beyond a cutting or resection tool, like the cutting tools 102, 1102. A non-limiting illustration of the humeral resection guide 2100 having the first and second arms 2110, 2120 used in conjunction with an intramedullary guide 400 for use in a surgical procedure on the humerus 1012 is illustrated in FIG. 19. The intramedullary guide 400 allows for some existing technologies that are currently used in shoulder procedures to be used in conjunction with the humeral resection guide 2100, and/or other humeral resection guides disclosed herein or otherwise derivable from the present disclosures. As shown, a surgeon can place a shaft 402 in a humeral canal, which can create a vertical alignment. A clamp 404 can be attached to the shaft 402 providing the vertical alignment and then back to the first, inferior arm 2110, for example via an arm 406 coupled to the arm 2110 by way of a securing mechanism, as shown a screw 408. This can, at least while the screw 408 is in a locked configuration to secure the arm 406 to the first arm 2110, set the angle of the guide 2100 with respect to the elongate shaft 1014 of the humerus 1012. This can eliminate some variability and setting guide that can occur, for example, due to patient anatomy. Additional features of an intramedullary guide 400 illustrated but not necessarily described herein will be understood by a person skilled in the art, in view of FIG. 19, the knowledge of the skilled person, and the present disclosures.

Kits

Different sized and configured arms for use with different patient and patient anatomies, and other components of a guide(s) and/or used in conjunction with the guides of the present disclosure, can be provided together as a kit. This humeral resection guide kit can include, for example, any combination of superior arms 110, 1110, 1110', 2110, 3110, inferior arms 1120, 1120', 2120, 3120, guide extenders 120, vertical alignment plates 140, 1140, 2140, 3140, version handles 150, 1150, 2150, 3150, vertical guide rods 160, 160', 2160*a*, 2160*b*, 3160, cutting tools 102, 1102, 3102 all of various sizes, and/or intramedullary guides 400, among other components and features provided for herein. A person skilled in the art will appreciate that such kits are not limited to only the embodiments disclosed and explicitly illustrated herein, but rather, includes various configuration and iterations accounted for in the text and/or otherwise understood to achieve similar purposes as provided for herein. The various components can be sized and/or shaped for different patient anatomies (e.g., adult, child, patient having certain bone formations due to various ailments or diseases, etc.).

Other Considerations

The devices, tools, components, and the like described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the devices, tools, components, and the like due to the materials utilized, the presence of electrical components, etc.

Examples of the above-described embodiments can include the following:

1. A resection guide, comprising:

a superior radial arm having a proximal portion with at least one bone pin receiving opening formed therein and a distal portion configured to engage a humeral head of a humerus, a superior surface of the proximal portion of the superior radial arm defining a resecting plane of the resection guide;

a guide slot formed on the superior radial arm, the guide slot being defined by a ledge of the distal portion of the superior radial arm extending over the superior surface of the proximal portion of the superior radial arm, and the guide slot being configured to receive a cutting instrument therethrough and guide the cutting instrument along the resecting plane while cutting the humeral head, keeping the cutting instrument one of parallel or substantially parallel to the resecting plane.

2. The resection guide of example 1, further comprising a vertical alignment plate extending distally from the superior radial arm, a length of the vertical alignment plate and the superior surface of the proximal portion of the superior radial arm forming an angle therebetween, the angle defining a resecting angle of the resection guide, and thus an angle of the resecting plane of the resection guide.

3. The resection guide of example 2, wherein the angle formed by the length of the vertical alignment plate and the superior surface of the proximal portion of the superior radial arm is congruent with the resecting angle of the resection guide, and thus the angle of the resecting plane of the resection guide.

4. The resection guide of example 2 or 3, further comprising at least one handle-receiving opening formed in the vertical alignment plate, the opening being configured to receive a version handle for at least one of manipulating a location of the superior radial arm with respect to the humerus or checking for version alignment between the resection guide and the humerus.

5. The resection guide of example 4, further comprising a version handle configured to be coupled to the vertical alignment plate and configured to at least one of manipulate a location of the superior radial arm with respect to the humerus or check for version alignment between the resection guide and the humerus.

6. The resection guide of example 5, wherein the version handle further comprises a locking mechanism configured to selectively unlock and lock a location of the version handle with respect to the vertical alignment plate.

7. The resection guide of example 6, wherein the locking mechanism comprises a latch.

8. The resection guide of any of examples 5 to 7, wherein a distal portion of the version handle forms an angle with the proximal portion of the version handle to define a retroversion angle.

9. The resection guide of example 8, wherein the angle formed by the distal and proximal portions of the version handle, and thus the retroversion angle, is approximately 30°.

10. The resection guide of any of examples 5 to 9, wherein the version handle further comprises at least one opening formed therein for receiving a vertical guide rod, the at least one opening being configured to receive a vertical guide rod such that the vertical guide rod can extend substantially along a length or axis defined by a shaft of the humerus.

11. The resection guide of example 10, wherein the at least one opening comprises:

a first opening configured to receive a vertical guide rod such that the vertical guide rod can extend distally, proximate to the shaft of the humerus; and a second opening configured to receive a vertical guide rod such that the vertical guide rod can extend proximally, away from the shaft of the humerus.

12. The resection guide of example 10 or 11, further comprising at least one vertical guide rod configured to be coupled to the vertical alignment plate by way of the at least one opening, the vertical guide rod being configured to extend substantially along a length or axis defined by the shaft of the humerus.

13. The resection guide of any of examples 1 to 12, wherein the at least one bone pin receiving opening includes a longitudinal axis extending through a length thereof that is substantially parallel to the resecting plane.

14. The resection guide of any of examples 1 to 13, wherein the at least one bone pin receiving opening formed in the proximal portion of the superior radial arm further comprises a plurality of bone pin receiving openings formed in the proximal portion of the superior radial arm, with at least two openings of the plurality of bone pin receiving openings being non-parallel.

15. The resection guide of any of examples 1 to 14, wherein an inner surface of the distal portion of the superior radial arm comprises one or more gripping protrusions configured to help secure the superior radial arm to the humerus.

16. The resection guide of any of examples 1 to 15, further comprising a removable extender coupled to the proximal portion of the superior radial arm and configured to extend the resecting plane inferiorly, the removable extender including at least one inferior bone pin receiving opening.

17. The resection guide of example 16, wherein the removable extender further comprises a lever configured to selectively lock and unlock the removable extender from the superior radial arm.

18. A method for resecting a humeral head, comprising:

coupling a superior arm of a resection guide to at least one of a humeral head or a humerus such that the superior arm engages the humeral head;

passing at least one bone pin through a portion of the resection guide and into at least one of the humeral head or the humerus; and resecting the humeral head using the resection guide to guide a cutting instrument and create a humeral resection surface.

19. The method of example 18, wherein resecting the humeral head using the resection guide further comprises passing the cutting instrument through a guide slot formed on the superior arm, the guide slot serving to guide the cutting instrument.

20. The method of example 18 or 19, wherein engaging the humeral head with a superior arm of a resection guide further comprises engaging the humeral head at a location that is at least one of at or proximate to a supraspinatus attachment point on the humeral head.

21. The method of any of examples 18 to 20, further comprising aligning the guide slot to a bicipital groove of the humerus.

22. The method of any of examples 18 to 21, further comprising aligning a vertical alignment plate of the resection guide with an elongate shaft of the humerus to set a location of the superior arm.

23. The method of example 22, wherein a vertical guide rod is coupled to at least one of the vertical alignment plate or a handle coupled to the vertical alignment plate, the vertical guide rod extending along the elongate shaft of the humerus in conjunction with aligning the vertical alignment plate of the resection guide with the elongate shaft of the humerus.

24. The method of example 22 or 23, further comprising moving the vertical alignment plate to change an angle of inclination of a resecting plane defined by the resection guide.

25. The method of any of examples 18 to 24, wherein passing at least one bone pin through a portion of the resection guide and into the humeral head occurs such that the at least one bone pin does not pass through soft tissue in the glenohumeral joint space.

26. The method of any of examples 18 to 25, further comprising:

mating a handle to the resection guide; and checking angular alignment with a forearm using the handle.

27. The method of example 26, further comprising manipulating the handle to adjust a location of the superior arm of the resection guide.

28. The method of any of examples 18 to 27, wherein a subscapularis tendon proximate to the humeral head is intact during each of the coupling, passing, and resecting actions.

29. The method of example 28, wherein coupling a superior arm of a resection guide to at least one of a humeral head or a humerus such that the superior arm engages the humeral head further comprises passing the superior arm through a rotator interval proximate to the humeral head.

30. The method of any of examples 18 to 29, further comprising:

mating an extender to the superior arm; and passing at least one inferior bone pin through a portion of the extender and into the humeral head such that the at least one inferior bone pin does not pass through soft tissue in the glenohumeral joint space.

31. The method of example 30, further comprising passing the extender inferior to a subscapularis tendon proximate to the humeral head.

32. A resection guide, comprising:

a first arm having a proximal portion and a distal portion, the distal portion being configured to engage a first portion of a bone to be cut;

a second arm having a proximal portion and a distal portion, the distal portion being configured to engage a second portion of the bone to be cut, the first and second arms being configured to define a resecting plane for the resection guide; and a connection pivot disposed at the proximal portions of both the first and second arms such that the first arm pivots with respect to the second arm, the connection pivot being configured to selectively, pivotally couple the proximal portion of the first arm to the proximal portion of the second arm, wherein the resection guide is configured to permit movement of one or both of the first or second arms across at least two degrees of freedom.

33. The resection guide of example 32, wherein the resection guide is configured to permit each of the first arm and the second arm to be separately delivered to a surgical site and be subsequently coupled by way of the connection pivot while the first and second arms are located at the surgical site.

34. The resection guide of example 32 or 33, wherein the first and second arms are configured to form a grasping perimeter that extends around at least a majority of a cross-sectional area of a perimeter of the bone to be cut.

35. The resection guide of example 34, wherein the grasping perimeter extends around at least a majority, but not an entirety, of the cross-sectional area of the perimeter of the bone to be cut.

36. The resection guide of example 35, wherein the grasping perimeter is approximately in the range of about 50% to about 95% of the cross-sectional area of the perimeter of the bone to be cut.

37. The resection guide of any of examples 32 to 36, wherein the resection guide is configured for use in a shoulder region such that the resecting plane defined by the first and second arms is defined in a rotator interval of the shoulder region.

38. The resection guide of any of examples 32 to 37, wherein the resection guide is configured for use in a shoulder region such the first arm defines a height of a resection plane when it is placed against a supraspinatus attachment.

39. The resection guide of any of examples 32 to 38, further comprising:

a horizontal slot formed in the proximal portion of the first arm, wherein the connection pivot is disposed in the horizontal slot when the proximal portions of the first and second arms are pivotally coupled by the connection pivot, and wherein the first arm is configured to move relative to the connection pivot such that a location of the connection pivot with respect to the horizontal slot changes, in turn changing a location of the first arm with respect to the second arm.

40. The resection guide of example 39, wherein the horizontal slot comprises an open terminal end, and wherein the first arm is configured to be detached from the second arm by moving the first arm relative to the connection pivot such that the connection pivot passes out of the slot through the open terminal end.

41. The resection guide of any of examples 32 to 40, further comprising at least one slot formed in a surface of at least one of the first and second arms, the at least one slot being configured to receive a pin therein for setting a position of the resection guide with respect to the bone to be cut.

42. The resection guide of example 41, wherein the at least one slot comprises:

a first slot formed in a surface of the first arm; and a second slot formed in a surface of the second arm.

43. The resection guide of example 41 or 42, wherein the at least one slot is disposed at an angle with respect to the respective first or second arm such that it is aligned with the resecting plane defined by the first and second arms.

44. The resection guide of any of examples 41 to 43, wherein the at least one slot is configured to receive a bone pin therein and position the bone pin such that it is tangent to a superior portion of the resecting plane to extend a resecting surface of the resection guide, the resecting surface being a surface along which a cutting tool is configured to pass to perform a cut.

45. The resection guide of any of examples 32 to 44, wherein the second arm comprises an elevated ridge on the distal portion thereof, the elevated ridge extending above a defined resecting plane by the first and second arms.

46. The resection guide of any of examples 32 to 45, wherein the resection guide is configured for resecting to be performed with the first arm disconnected from the second arm such that the second arm remains at a surgical site while the first arm is removed from the surgical site.

47. The resection guide of any of examples 32 to 46, further comprising:

a vertical alignment plate coupled to the second arm and configured to be aligned with an elongate shaft of the bone to be cut, wherein an angle formed between the vertical alignment plate and a bottom surface of the second arm is configured to help define a location of the defined resecting plane.

48. The resection guide of example 47, wherein the angle formed between the vertical alignment plate and the bottom surface of the second arm is adjustable by moving a location of the vertical alignment plate with respect to the second arm.

49. The resection guide of any of examples 32 to 48, further comprising a locking mechanism configured to engage the connection pivot to selectively place the connection pivot, and thus the first and second arms coupled thereto, in each of an unlocked configuration and a locked configuration.

50. The resection guide of example 49, wherein the locking mechanism is configured to be moved between the unlocked configuration and the locked configuration with a single digit.

51. The resection guide of any of examples 32 to 50, further comprising:

a vertical slot formed in the proximal portion of the second arm, wherein the connection pivot is disposed in the vertical slot when the proximal portions of the first and second arms are pivotally coupled by the connection pivot, and wherein the connection pivot is configured to move through the vertical slot to change a location of the first arm with respect to the second arm.

52. The resection guide of any of examples 32 to 51, wherein the resection guide is configured to permit movement of one or both of the first or second arms, and thus the resecting plane defined by the first and second arms, across at least three degrees of freedom.

53. The resection guide of example 52, wherein the resection guide is configured to permit movement of the resecting plane across at least four degrees of freedom.

54. The resection guide of example 53, wherein the resection guide is configured to permit movement of the resecting plane across at least five degrees of freedom.

55. The resection guide of any of examples 32 to 54, wherein the bone to be cut comprises a humeral head, and wherein the resection guide is configured such that the connection pivot allows for movement of the first arm with respect to the second arm to accommodate at least one of different humeral head sizes or different humeral head shapes.

56. The resection guide of any of examples 32 to 55, wherein the bone to be cut comprises a humeral head, and wherein the resection guide is configured to be used to cut the humeral head while a subscapularis tendon proximate to the humeral head is intact.

57. The resection guide of example 56, wherein the resection guide is configured to be inserted to a surgical site that includes the humeral head at least one of superior to the intact subscapularis tendon or inferior to the intact subscapularis tendon.

58. A method for resecting a humeral head, comprising:

disposing a first arm of a resection guide proximate to a first portion of a perimeter of a humeral head of a humerus;

disposing a second arm of the resection guide proximate to a second portion of the perimeter of the humeral head;

after the first and second arms are proximate to the humeral head, pivotally coupling the first arm to the second arm;

engaging at least one of the humeral head or the humerus with first and second arms of the resection guide, the first and second arms defining a resecting plane;

resecting the humeral head.

59. The method of example 58, wherein disposing a first arm of a resection guide proximate to a first portion of a perimeter of a humeral head comprises passing the first arm though a rotator interval and to a posterior portion of a humeral articular margin of the humeral head.

60. The method of example 58 or 59, wherein disposing a second arm of the resection guide proximate to a second portion of the perimeter of the humeral head comprises passing the second arm through an inferior access point to an inferior articular margin of the humeral head.

61. The method of any of examples 58 to 60, wherein pivotally coupling the first arm to the second arm comprises disposing a pivot through proximal portions of each of the first and second arms to permit movement of one or both of the first or second arms across at least two degrees of freedom.

62. The method of any of examples 58 to 61, wherein engaging the humeral head with the first and second arms of the resection guide comprises rotating the first arm with respect to at least one of the pivot and the second arm.

63. The method of any of examples 58 to 62, wherein resecting the humeral head comprises resecting the humeral head along the resecting plane, using at least one of the first or second arms as a guide.

64. The method of any of examples 58 to 63, wherein resecting the humeral head comprises engaging an elevated ridge formed on at least one of the first and second arms with a cutting tool performing the resecting the humeral head, the elevated ridge preventing the cutting tool from extending beyond a desired surgical site.

65. The method of any of examples 58 to 64, wherein a combination of the first portion of the perimeter of the humeral head and the second portion of the humeral head are engaged by the first and second arms at a cross-section thereof such that at least a majority of a perimeter of the humeral head as defined at the cross-section is engaged by the first and second arms.

66. The method of example 65, wherein the perimeter of the humeral head as defined at the cross-section that is engaged by the first and second arms is not an entirety of the perimeter of the humeral head as defined at the cross-section.

67. The method of example 66, wherein the perimeter of the humeral head as defined at the cross-section that is engaged by the first and second arms is approximately in the range of about 50% to about 95% of the cross-sectional area of the perimeter of the humeral head.

68. The method of any of examples 58 to 67, wherein the resecting plane defined by the first and second arms is defined in a rotator interval proximate to the humeral head.

69. The method of any of examples 58 to 68, wherein the first arm defines a height of a resecting plane when it is placed against a supraspinatus attachment.

70. The method of any of examples 58 to 69, further comprising sliding the first arm with respect to the second arm approximately along an X-axis of the resecting plane to adjust a distance between a distal tip of the first arm and a proximal portion of the second arm.

71. The method of any of examples 58 to 70, further comprising sliding the first arm with respect to the second arm approximately along a Y-axis of the resecting plane to adjust a distance between a proximal portion of the first arm and at least one of a proximal portion, an intermediate portion, or a distal portion of the second arm.

72. The method of any of examples 58 to 71, further comprising rotating the resecting plane with respect to a vertical alignment plate that is one of coupled to or part of the second arm.

73. The method of any of examples 58 to 72, further comprising rotating a vertical alignment plate that is one of coupled to or part of the second arm.

74. The method of any of examples 58 to 73, further comprising:

coupling at least one vertical extension rod to at least one of the first arm, the second arm, or, when provided, a vertical alignment plate that is one of coupled to or part of the second arm; and aligning the at least one vertical extension rod with an anatomical location to place the resection guide at a desired position.

75. The method of any of examples 58 to 74, further comprising sliding the first arm with respect to the second arm to decouple the first arm from the second arm.

76. The method of any of examples 58 to 75, further comprising:

disengaging the first arm from the humeral head; and decoupling the first arm from the second arm, wherein resecting the humeral head is performed with the second arm engaged with at least one of the humeral head or humerus while the first arm is not engaged with either the humeral head or the humerus and is decoupled from the second arm.

77. The method of any of examples 58 to 76, further comprising locking movement of the first arm with respect to the second arm to place the first and second arms in a locked configuration in which the first and second arms are engaged with the humeral head.

78. The method of example 77, further comprising unlocking the first arm with respect to the second arm to permit adjustment of a position of the first arm with respect to the second arm, thus placing at least one of the first or second arms in an unlocked configuration.

79. The method of example 77 or 78, wherein at least one of locking or unlocking is performed with a single digit.

80. The method of any of examples 58 to 79, further comprising inserting at least one bone pin into at least one of the humeral head or humerus to help fixate a location of the resection guide with respect to the humeral head.

81. The method of example 80, wherein inserting at least one bone pin into at least one of the humeral head or the humerus comprises inserting an inferior bone pin below a subscapularis tendon proximate to the humeral head and through a slot formed in the second arm.

82. The method of example 80 or 81, wherein inserting at least one bone pin into at least one of the humeral head or the humerus comprises inserting a superior bone pin through a rotator interval proximate to the humeral head and through a slot formed in the first arm.

83. The method of example 82, wherein the superior bone pin is tangent to a superior portion of the resecting plane to extend a resecting surface along which a cutting tool performing the resecting the humeral head passes to an opposite side of the bone being resected.

84. The method of any of examples 58 to 83, wherein a subscapularis tendon is intact during an entirety of the method.

85. The method of example 84, wherein each of the first arm and the second arm are inserted to the perimeter of the humeral head at least one of superior to the intact subscapularis tendon or inferior to the intact subscapularis tendon.

86. The method of example 84 or 85, further comprising manipulating the subscapularis tendon to increase visibility by moving it away from its natural location while keeping it intact.

One skilled in the art will appreciate further features and advantages of the disclosure based on the above-described embodiments and techniques. Accordingly, the disclosure is not to be limited by what has been particularly shown and described, except as indicated by the appended claims. By way of example, while the present disclosure primarily focuses on the use of humeral resection guides and related components in conjunction with shoulder arthroplasty procedures, the disclosed guides can be used and/or adapted for use with other shoulder procedures and/or for use in surgical procedures in other locations in the body. Accordingly, references to shoulder anatomy and/or resection guides herein being "humeral" are not limiting to such use, and the disclosures herein can be used in procedures and resection guides for other anatomies (e.g., boney anatomies), whether human or other animals. A person skilled in the art, in view of the present disclosures, will be able to adapt some or all of the various systems, instruments, tools, and techniques disclosed herein for use in surgical procedures in other locations and/or for use with non-humans.

Further, a person skilled in the art will appreciate that various features or other disclosures associated with one embodiment of a device, system, component, and/or surgical technique can be used in other devices, systems, components, and/or surgical techniques disclosed herein or otherwise derivable therefrom. It is within the skill of a person skilled in the art to be able to apply teachings, or part of teachings, from one such device, system, component, and/or surgical technique to one or more other devices, systems, components, and/or surgical techniques. For example, to the extent one or more embodiments describes a certain number and/or ability as it relates to degrees of freedom, a person having skill in the art, in view of the present disclosures, will understand that those degrees of freedom are applicable to other embodiments as well even where the other embodiments do not describe them This is true unless explicitly stated or otherwise understood by a person skilled in the art that a certain embodiment is incapable of operating in a particular fashion that would permit that degree(s) of freedom.

To the extent the present disclosure does not describe materials that can be used to manufacture the resection guides and associated components and/or does not identify particular dimensions and the like for the resection guides and associated components, a person skilled in the art will appreciate typical materials and dimensions that are appropriate. All publications and references cited herein are expressly incorporated herein by reference in their entirety. Further, U.S. Provisional Patent Application No. 63/689,631, entitled "Smart Shoulder Tissue Sparing Approach Techniques and Related Instrumentation," is incorporated by reference herein in its entirety.

What is claimed is:

1. A resection guide, comprising:

a superior radial arm having a proximal portion with at least one bone pin receiving opening formed therein and a distal portion configured to contact a humeral head of a humerus with the distal portion extending from the proximal portion in a direction towards a posterior portion of the humeral head, and a superior surface of the proximal portion of the superior radial arm defining a resecting plane of the resection guide;

a guide slot formed on the superior radial arm, the guide slot being defined by a ledge of the distal portion of the superior radial arm extending over the superior surface of the proximal portion of the superior radial arm, and the guide slot being configured to receive a cutting instrument therethrough and guide the cutting instrument along the resecting plane while cutting the humeral head, keeping the cutting instrument one of parallel or substantially parallel to the resecting plane; and a vertical alignment plate extending distally from the superior radial arm, a length of the vertical alignment plate and the superior surface of the proximal portion of the superior radial arm forming an angle therebetween that is approximately in a range of about 125° to about 145°, the angle defining a resecting angle of the resection guide, and thus an angle of the resecting plane of the resection guide.

2. The resection guide of claim 1, wherein the angle formed by the length of the vertical alignment plate and the superior surface of the proximal portion of the superior radial arm is congruent with the resecting angle of the resection guide, and thus the angle of the resecting plane of the resection guide.

3. The resection guide of claim 1, further comprising at least one handle-receiving opening formed in the vertical alignment plate, the opening being configured to receive a version handle for at least one of manipulating a location of the superior radial arm with respect to the humerus or checking for version alignment between the resection guide and the humerus.

4. The resection guide of claim 3, further comprising a version handle configured to be coupled to the vertical alignment plate and configured to at least one of manipulate a location of the superior radial arm with respect to the humerus or check for version alignment between the resection guide and the humerus.

5. The resection guide of claim 4, wherein a distal portion of the version handle forms an angle with a proximal portion of the version handle to define a retroversion angle.

6. The resection guide of claim 4, wherein the version handle further comprises at least one opening formed therein for receiving a vertical guide rod, the at least one opening being configured to receive a vertical guide rod such that the vertical guide rod can extend substantially along a length or axis defined by a shaft of the humerus.

7. The resection guide claim 1, wherein the at least one bone pin receiving opening includes a longitudinal axis extending through a length thereof that is substantially parallel to the resecting plane.

8. The resection guide of claim 1, wherein the at least one bone pin receiving opening formed in the proximal portion of the superior radial arm further comprises a plurality of bone pin receiving openings formed in the proximal portion of the superior radial arm, with at least two openings of the plurality of bone pin receiving openings being non-parallel.

9. The resection guide of claim 1, further comprising a removable extender coupled to a proximal end of the proximal portion of the superior radial arm and configured to extend the resecting plane inferiorly, the removable extender including at least one inferior bone pin receiving opening.

10. The resection guide of claim 9, wherein the removable extender further comprises a lever configured to selectively lock and unlock the removable extender from the superior radial arm.

11. A resection guide, comprising:

a superior radial arm having a proximal portion with at least one bone pin receiving opening formed therein and a distal portion configured to contact a humeral head of a humerus with the distal portion extending from the proximal portion in a direction towards a posterior portion of the humeral head, and a superior surface of the proximal portion of the superior radial arm defining a resecting plane of the resection guide;

a guide slot formed on the superior radial arm, the guide slot being defined by a ledge of the distal portion of the superior radial arm extending over the superior surface of the proximal portion of the superior radial arm, and the guide slot being configured to receive a cutting instrument therethrough and guide the cutting instrument along the resecting plane while cutting the humeral head, keeping the cutting instrument one of parallel or substantially parallel to the resecting plane; and a removable extender coupled to a proximal end of the proximal portion of the superior radial arm and configured to extend the resecting plane inferiorly, the removable extender including at least one inferior bone pin receiving opening.

12. The resection guide of claim 11, wherein the removable extender further comprises a lever configured to selectively lock and unlock the removable extender from the superior radial arm.

13. The resection guide of claim 11, further comprising a vertical alignment plate extending distally from the superior radial arm, a length of the vertical alignment plate and the superior surface of the proximal portion of the superior radial arm forming an angle therebetween that is approximately in a range of about 125° to about 145°, the angle defining a resecting angle of the resection guide, and thus an angle of the resecting plane of the resection guide.

14. The resection guide of claim 13, wherein the angle formed by the length of the vertical alignment plate and the superior surface of the proximal portion of the superior radial arm is congruent with the resecting angle of the resection guide, and thus the angle of the resecting plane of the resection guide.

15. The resection guide of claim 13, further comprising at least one handle-receiving opening formed in the vertical alignment plate, the opening being configured to receive a version handle for at least one of manipulating a location of the superior radial arm with respect to the humerus or checking for version alignment between the resection guide and the humerus.

16. The resection guide of claim 15, further comprising a version handle configured to be coupled to the vertical alignment plate and configured to at least one of manipulate a location of the superior radial arm with respect to the humerus or check for version alignment between the resection guide and the humerus.

17. The resection guide of claim 16, wherein a distal portion of the version handle forms an angle with a proximal portion of the version handle to define a retroversion angle.

18. The resection guide of claim 16, wherein the version handle further comprises at least one opening formed therein for receiving a vertical guide rod, the at least one opening being configured to receive a vertical guide rod such that the vertical guide rod can extend substantially along a length or axis defined by a shaft of the humerus.

19. The resection guide claim 11, wherein the at least one bone pin receiving opening includes a longitudinal axis extending through a length thereof that is substantially parallel to the resecting plane.

20. The resection guide of claim 11, wherein the at least one bone pin receiving opening formed in the proximal portion of the superior radial arm further comprises a plurality of bone pin receiving openings formed in the proximal portion of the superior radial arm, with at least two openings of the plurality of bone pin receiving openings being non-parallel.

* * * * *